United States Patent
Fahmy et al.

(10) Patent No.: US 11,517,628 B2
(45) Date of Patent: Dec. 6, 2022

(54) PARTICLES FOR SPATIOTEMPORAL RELEASE OF AGENTS

(71) Applicant: Yale University, New Haven, CT (US)

(72) Inventors: Tarek Fahmy, Middlefield, CT (US); Philip Kong, New Haven, CT (US); Sean Bickerton, Hamden, CT (US); Michael D. McHugh, Braintree, MA (US); Jung Seok Lee, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 17/054,119

(22) PCT Filed: May 8, 2019

(86) PCT No.: PCT/US2019/031314
§ 371 (c)(1),
(2) Date: Nov. 9, 2020

(87) PCT Pub. No.: WO2019/217552
PCT Pub. Date: Nov. 14, 2019

(65) Prior Publication Data
US 2021/0113713 A1 Apr. 22, 2021

Related U.S. Application Data

(60) Provisional application No. 62/669,242, filed on May 9, 2018.

(51) Int. Cl.
| | |
|---|---|
| A61K 31/426 | (2006.01) |
| A61K 47/69 | (2017.01) |
| A61K 39/00 | (2006.01) |
| B82Y 5/00 | (2011.01) |

(52) U.S. Cl.
CPC ...... *A61K 47/6939* (2017.08); *A61K 39/0008* (2013.01); *A61K 47/6951* (2017.08); *A61K 2039/55555* (2013.01); *A61K 2300/00* (2013.01); *B82Y 5/00* (2013.01)

(58) Field of Classification Search
CPC combination set(s) only.
See application file for complete search history.

(56) References Cited

U.S. PATENT DOCUMENTS

| | | | |
|---|---|---|---|
| 5,120,727 A | 6/1992 | Kao | |
| 5,162,333 A | 11/1992 | Failli | |
| 5,202,332 A | 4/1993 | Hughes | |
| 5,385,908 A | 1/1995 | Nelson | |
| 5,484,790 A | 1/1996 | Failli | |
| 5,530,006 A | 6/1996 | Waranis | |
| 5,559,112 A | 9/1996 | Skotnicki | |
| 5,567,709 A | 10/1996 | Skotnicki | |
| 5,780,462 A | 7/1998 | Lee | |
| 5,989,591 A | 11/1999 | Nagi | |
| 6,015,809 A | 1/2000 | Zhu | |
| 6,960,356 B1 | 11/2005 | Talwar | |
| 2010/0158979 A1 | 6/2010 | Russell | |
| 2013/0150952 A1 | 6/2013 | Su | |
| 2014/0037708 A1 | 2/2014 | Wei | |
| 2015/0118318 A1* | 4/2015 | Fahmy | A61K 47/6951 424/498 |
| 2015/0125384 A1 | 5/2015 | Mellman | |
| 2016/0220501 A1 | 8/2016 | Fraser | |
| 2016/0303052 A1* | 10/2016 | Fahmy | A61K 9/5153 |
| 2016/0317455 A1 | 11/2016 | Blanco | |

FOREIGN PATENT DOCUMENTS

| | | |
|---|---|---|
| WO | 9504738 | 2/1995 |
| WO | 9516691 | 6/1995 |
| WO | 9522972 | 8/1995 |
| WO | 2009046446 | 4/2009 |

OTHER PUBLICATIONS

Zhang, et al., "Amelioration of experimental autoimmune encephalomyelitis by beta-elemene treatment is associated with Th17 and Treg cell balance", J. Mol. Neurosci., 44(1): 31-40 (2011).
Adair, et al., "Human Tregs Made Antigen Specific by Gene Modification: The Power to Treat Autoimmunity and Antidrug Antibodies with Precision", Front. Immunol., 8:1117 (2017).
Akdis, et al., "Mechanisms of allergen-specific immunotherapy and immune tolerance to allergens", World Allergy Organ J., 8:17 (2015).
Alloatti, et al., "Dendritic cell maturation and cross-presentation: timing matters!", Immunol. Rev., 272:97-108 (2016).
Annamalai, et al, "Harnessing Macrophage-Mediated Degradation of Gelatin Microspheres for Spatiotemporal Control of BMP2 Release", Biomaterials, 161:216-227 (2018).
Araki, et al., "mTOR regulates memory CD8 T-cell differentiation", Nature, 460(7251):108-112 (2009).
Bailey, et al., "A simple whole blood bioassay detects cytokine responses to anti-CD28SA and anti-CD52 antibodies", J. Pharmacol. Toxicol. Methods, 68(2):231-239 (2013).
Balthasar, et al., "Antigen Presentation to B Cells", Trends in Immunology, 37(12):844-854 (2016).

(Continued)

*Primary Examiner* — James W Rogers
(74) *Attorney, Agent, or Firm* — Pabst Patent Group LLP

(57) ABSTRACT

Particles with a spatial and/or temporal release profile for delivery of different agents at different times to the same cells of a subject have been developed. The particles include a core polymeric particle containing a polymer and a first agent, a tethering moiety, covalent linker or covalent linkage attached to the core particle, and a tethered particle attached to the particle via the tethering moiety, covalent linker or covalent linkage and containing a second agent, where the agents are released at different times within or to the same cells. The first and second agents may be a therapeutic or prophylactic agent, such as an antigen, an immunomodulator, an anti-neoplastic agent, a hormone, an inhibitor, etc. The particles may form compositions for treating diseases with a spatial and/or temporal treatment regimen.

20 Claims, 42 Drawing Sheets

(56) References Cited

OTHER PUBLICATIONS

Bandyopadhyay, et al., "The impact of nanoparticle ligand density on dendritic-cell targeted vaccines", Biomaterials, 32(11):3094-3105 (2011).
Baum, et al., "Theranostics: From Molecular Imaging Using Ga-68 Labeled Tracers and PET/CT to Personalized Radionuclide Therapy—The Bad Berka Experience", Theranostics, 2(5):437-447 (2012).
Belz, et al., "The CD8alpha(+) dendritic cell is responsible for inducing peripheral self-tolerance to tissue-associated antigens", J. Exp. Med., 196(8):1099-1104 (2002).
Bhardwaj, et al., "PLGA nanoparticles stabilized with cationic surfactant: safety studies and application in oral delivery of paclitaxel to treat chemical-induced breast cancer in rat", Pharm. Res., 26(11):2495-2503 (2009).
Bilate, et al., "Induced CD4+Foxp3+ regulatory T cells in immune tolerance", Annu. Rev. Immunol., 30:733-758 (2012).
Blank, et al., "Interaction of PD-L1 on tumor cells with PD-1 on tumor-specific T cells as a mechanism of immune evasion: implications for tumor immunotherapy", Cancer Immunology, Immunotherapy, 54:307-314 (2005).
Boks, et al., "IL-10-generated tolerogenic dendritic cells are optimal for functional regulatory T cell induction—a comparative study of human clinical-applicable DC", Clinical Immunology, 142(3):332-42 (2012).
Bonifaz, et al., "Efficient targeting of protein antigen to the dendritic cell receptor DEC-205 in the steady state leads to antigen presentation on major histocompatibility complex class I products and peripheral CD8+ T cell tolerance", J Exp Med, 196(12):1627-38 (2002).
Buttel, et al., "Taking immunogenicity assessment of therapeutic proteins to the next level", Biologicals, 39:100-109 (2011).
Cadwell, et al., "Crosstalk between autophagy and inflammatory signalling pathways: balancing defence and homeostasis", Nature Reviews Immunology, 16:661-675 (2011).
Capini, et al., "Antigen-Specific Suppression of Inflammatory Arthritis Using Liposomes", J. Immunol. 182(6):3556-65 (2009).
Celli, et al., "Real-Time Manipulation of T Cell-Dendritic Cell Interactions In Vivo Reveals the Importance of Prolonged Contacts for CD4+ T Cell Activation", Immunity, 27:625-634 (2007).
Chen, et al., "Evaluation of Ion-exchange Microspheres as Carriers for the Anticancer Drug Doxorubicin: In-vitro Studies", J. Pharm. Pharmacol., 44(3):211-215 (1992).
Choi, et al., "Structure of the FKBP12-rapamycin complex interacting with the binding domain of human FRAP", Science, 273(5272):239-242 (1996).
Collison, et al., "In Vitro Treg Suppression Assays", Methods in Molecular Biology, 707:21-37 (2011).
Constantinescu, et al., "Experimental autoimmune encephalomyelitis (EAE) as a model for multiple sclerosis (MS)", Br. J. Pharmacol., 164:1079-1106 (2011).
Corthay, et al., "A three-cell model for activation of naive T helper cells", Scandinavian Journal of Immunology, 64: 93-6 (2006).
Croft, et al., "Kinetics of Antigen Expression and Epitope Presentation during Virus Infection", PLOS Pathogens, 9:e1003129 (2013).
Dai, et al., "The PD-1/PD-Ls pathway and autoimmune diseases", Cellular immunology, 290(1):72-79 (2014).
Demento, et al., "Inflammasome-activating nanoparticles as modular systems for optimizing vaccine efficacy", Vaccine, 27(23):3013-3021 (2009).
Domogalla, et al., "Tolerance through Education: How Tolerogenic Dendritic Cells Shape Immunity", Front. Immunol., 8:1764 (2017).
Dudek, et al., "Immature, Semi-Mature, and Fully Mature Dendritic Cells: Toward a DC-Cancer Cells Interface That Augments Anticancer Immunity", Frontiers in Immunology, 4:438 (2013).
Elkord, et al., "Helios expression in FoxP3(+) T regulatory cells", Expert Opin. Biol. Ther., 12:1423-1425 (2012).
Ezzelarab, et al., "Adoptive Cell Therapy with Tregs to Improve Transplant Outcomes: The Promise and the Stumbling Blocks", Curr. Transplant. Rep., 3:265-274 (2016).
Fahmy, et al., "Surface modification of biodegradable polyesters with fatty acid conjugates for improved drug targeting", Biomaterials, 26(28):5727-5736 (2005).
Faivre, et al., "Current development of mTOR inhibitors as anticancer agents", Nature Reviews, Drug Discovery, 5:671-688 (2006).
Farag, et al., "Rate of release of organic carboxylic acids from ion-exchange resins", J. Pharm. Sci., 77(10):872-875(1988).
Fischer, et al., "Use of rapamycin in the induction of tolerogenic dendritic cells", Handb. Exp. Pharmacol., 188:215-32 (2009).
Foley, et al., "Ex vivo rapamycin generates donor Th2 cells that potently inhibit graft-versus-host disease and graft-versus-tumor effects via an IL-4-dependent mechanism", J. Immunol., 175:5732-5743 (2005).
Francisco, et al., "PD-L1 regulates the development, maintenance, and function of induced regulatory T cells", J. Exp. Med., 206(13):3015-3029 (2009).
Fromen, et al., "Nanoparticle surface charge impacts distribution, uptake and lymph node trafficking by pulmonary antigen-presenting cells", Nanomedicine, 12:677-687 (2016).
Genard, et al., "Reprogramming of Tumor-Associated Macrophages with Anticancer Therapies: Radiotherapy versus Chemo- and Immunotherapies", Front. Immunol., 8:828 (2017).
Getts, et al., "Harnessing nanoparticles for immune modulation", Trends Immunol., 36(7):419-427 (2015).
Gliwinski, et al., "Cell-Based Therapies with T Regulatory Cells", BioDrugs 31:335-347 (2017).
Gomes, et al., "Harnessing Nanoparticies for Immunomodulation and Vaccines", Vaccines, 5(6):1-15 (2017).
Gregory, et al., "Vaccine delivery using nanoparticles", Frontiers in cellular and infection microbiology, 3(13):1-13 (2013).
Gross, et al., "Dendritic cell vaccination in autoimmune disease", Current opinion in Rheumatology, 25(2):268-74 (2013).
Harden, et al., "Indoleamine 2,3-dioxygenase and dendritic cell tolerogenicity", Immunological investigations 41(6-7):738-764 (2012).
Hey, et al., "Murine spleen contains a diversity of myeloid and dendritic cells distinct in antigen presenting function", J. Cell Mol. Med., 16(11):2611-2619 (2012).
Hosono, et al., "Increased expression of T cell activation markers (CD25, CD26, CD40L and CD69) in atherectomy specimens of patients with unstable angina and acute myocardial infarction", Atherosclerosis, 168:73-80 (2003).
International Search Report and Written Opinion for PCT/US2019/031314 dated Aug. 9, 2019.
Iwai, et al., "Involvement of PD-L1 on tumor cells in the escape from host immune system and tumor immunotherapy by PD-L1 blockade", Proceedings of the National Academy of Sciences of the United States of America, 99:12293-12297 (2002).
Jhunjhunwala, et al., "Controlled release formulations of IL-2, TGF-beta1 and rapamycin for the induction of regulatory T cells", J. Control Release, 159(1): 78-84 (2012).
Jia, et al., "Multifunctional nanoparticles for targeted delivery of immune activating and cancer therapeutic agents", J Control Release, 172(3):1020-1034 (2013).
Josefowicz, et al., "Regulatory T cells: mechanisms of differentiation and function", Annual Review of Immunology, 30:531-564 (2012).
Kapsenberg, "Dendritic-cell control of pathogen-driven T-cell polarization", Nature Reviews Immunology, 3(12):984-93 (2003).
Khodadust, et al., "Development of poly (I:C) modified doxorubicin loaded magnetic dendrimer nanoparticles for targeted combination therapy", Biomedicine and Pharmacotherapy, 68(8):979-987 (2014).
Kishimoto, et al., "Nanoparticles for the Induction of Antigen-Specific Immunological Tolerance", Front. Immunol., 9(230):1-13 (2018).
Kreutz, et al., "Antibody-antigen-adjuvant conjugates enable co-delivery of antigen and adjuvant to dendritic cells in cis but only have partial targeting specificity", PLoS One, 7:e40208 (2012).
Lamothe, et al., "Tolerogenic Nanoparticies Induce Antigen-Specific Regulatory T Cells and Provide Therapeutic Efficacy and Transferrable Tolerance against Experimental Autoimmune Encephalomyelitis", Front. Immunol., 9: 281 (2018).

(56) References Cited

OTHER PUBLICATIONS

Lass-Florl, et al., "Utility of PCR in diagnosis of invasive fungal infections: real-life data from a multicenter study", J. Clin. Microbiol., 51(3):863-868 (2013).

Li, et al., "Function of a Foxp3 cis-element in protecting regulatory T cell identity", Cell, 158:734-748 (2014b).

Li, et al., "Tolerogenic dendritic cells and their applications in transplantation", Cellular And Molecular Immunology, 12:24 (2014a).

Liechtenstein, et al., "PD-L1/PD-1 Co-Stimulatlon, a Brake for T cell Activation and a T cell Differentiation Signal", J. Clin. Cell Immunol., S12 (2012).

Lim, et al., "Mechanical interactions between dendritic cells and T cells correlate with T cell responsiveness", J. Immunol., 187:258-265 (2011).

Lin, et al., "Advances in distinguishing natural from induced Foxp3(+) regulatory T cells", Int. J. Clin. Exp. Pathol., 6(2):116-123 (2013).

Look, et al., "Nanogel-based delivery of mycophenolic acid ameliorates systemic lupus erythematosus in mice", The Journal of Clinical Investigation, 123(4): 1741-9 (2013).

Lutz, et al., "Immature, semi-mature and fully mature dendritic cells: which signals induce tolerance or immunity?", Trends Immunol., 23:445-449 (2002).

Makadia, et al., "Poly Lactic-co-Glycolic Acid (PLGA) as Biodegradable Controlled Drug Delivery Carrier", Polymers, 3:1377-1397 (2011).

Maldonado, et al., "How tolerogenic dendritic cells induce regulatory T cells", Advances in Immunology, 108:111-65 (2010).

Maldonado, et al., "Polymeric synthetic nanoparticies for the induction of antigen-specific immunological tolerance", Proceedings of the National Academy of Sciences, 112(2):E156-E165 (2015).

Mantegazza, et al., "Presentation of phagocytosed antigens by MHC class I and II", Traffic, 14:135-152 (2013).

Marcais, et al., "The metabolic checkpoint kinase mTOR is essential for IL-15 signaling during the development and activation of NK cells", Nat. Immunol., 15(8):749-757 (2014).

Martins, et al., "Adjuvant-enhanced CD4 T Cell Responses are Critical to Durable Vaccine Immunity", EBioMedicine, 3:67-78 (2016).

Matsue, et al., "Contrasting impacts of immunosuppressive agents (rapamycin, FK506, cyclosporin A, and dexamethasone) on bidirectional dendritic cell—T cell interaction during antigen presentation", J. Immunol., 169:3555-3564 (2002).

McHugh, et al., "Paracrine co-delivery of TGF-beta and IL-2 using CD4-targeted nanoparticles for induction and maintenance of regulatory T cells", Biomaterials, 59:172-181 (2015).

Merad, et al., "The dendritic cell lineage: ontogeny and function of dendritic cells and their subsets in the steady state and the inflamed setting", Annual review of Immunology, 31:563-604 (2013).

Mildner, et al., "Development and function of dendritic cell subsets", Immunity, 40(5):642-656 (2014).

Monneaux, et al., "Epitope spreading in systemic lupus erythematosus: identification of triggering peptide sequences", Arthritis & Rheumatism, 46(6):1430-1438 (2002).

Nierkens, et al., "Antigen cross-presentation by dendritic cell subsets: one general or all sergeants?", Trends Immunol., 34:361-370 (2013).

Palucka, et al., "Cancer immunotherapy via dendritic cells", Nature Reviews Cancer, 12(4):265-77 (2012).

Palucka, et al., "Dendritic cell-based cancer therapeutic vaccines", Immunity, 39(1): 38-48 (2013).

Platt, et al., "Mature dendritic cells use endocytic receptors to capture and present antigens", Proc. Natl. Acad. Sci. U.S.A., 107(9):4287-4292 (2010).

Powell, et al., "The mammalian target of rapamycin: linking T cell differentiation, function, and metabolism", Immunity, 33: 301-311 (2010).

Qi, et al., "Antitumor effects of PLGA nanoparticles encapsulating the human PNAS-4 gene combined with cisplatin in ovarian cancer", Oncol. Rep., 26: 703-710 (2011).

Qin, et al., "Regulation of Th1 and Th17 cell differentiation and amelioration of experimental autoimmune encephalomyelitis by natural product compound berberine", J. Immunol., 185:1855-1863 (2010).

Quintana, et al., "An endogenous aryl hydrocarbon receptor ligand acts on dendritic cells and T cells to suppress experimental autoimmune encephalomyelitis", Proceedings of the National Academy of Sciences, 107(48):20768-20773 (2010).

Raker, et al., "Tolerogenic Dendritic Cells for Regulatory T Cell Induction in Man", Frontiers in Immunology, 6:569 (2015).

Reichardt, et al., "Impact of mammalian target of rapamycin inhibition on lymphoid homing and tolerogenic function of nanoparticle-labeled dendritic cells following allogeneic hematopoietic cell transplantation", J. Immunol., 181:4770-4779 (2008).

Roncarolo, et al., "Regulatory T-cell immunotherapy for tolerance to self antigens and alloantigens in humans", Nature Reviews Immunology, 7(8):585-98 (2007).

Rosborough, et al., "Murine dendritic cell rapamycin-resistant and rictor-independent mTOR controls IL-10, B7-H1, and regulatory T-cell induction", Blood, 121(18):3619-3630 (2013).

Rubstov, et al., "Stability of the regulatory T cell lineage in vivo", Science, 329(5999):1667-1671 (2010).

Rui, et al., "Epigenetic silencing of CD8 genes by ThPOK-mediated deacetylation during CD4 T cell differentiation", J. Immunol., 189:1380-1390 (2012).

Sabatos-Peyton, et al., "Antigen-specific immunotherapy of autoimmune and allergic diseases", Curr. Opin. Immunol., 22(5):609-615 (2010).

Sallusto, et al., "The instructive role of dendritic cells on T-cell responses", Arthritis Research & Therapy, 4(Suppl3 ):S127-S132 (2002).

Shirali, et al., "Nanoparticle delivery of mycophenolic acid upregulates PD-L1 on dendritic cells to prolong murine allograft survival", Am. J. Transplant., 11(12):2582-2592 (2011).

Sojka, et al., "Mechanisms of regulatory T-ceii suppression—a diverse arsenal for a movina target", Immunology, 124(1):13-22 (2008).

Stenger, et al., "Dendritic cells and regulation of graft-versus-host disease and graft-versus-leukemia activity", Blood, 119(22):5088-103 (2012).

Sukhbaatar, et al., "mTOR-Mediated Regulation of Dendritic Cell Differentiation and Function", Trends Immunol., 37(11):778-769 (2016).

Suzuki, et al.. "Stent-based delivery of sirolimus reduces neointimal formation in a porcine coronary model", Circulation, 104(10):1188-1193 (2001).

Tang, et al., "Regulatory T-cell therapy in transplantation: moving to the clinic", Cold Spring Harb. Perspect. Med., 3:a015552 (2013).

Tanoue, et al., "Development and maintenance of intestinal regulatory T cells", Nat. Rev. Immunol., 16(5):295-309 (2016).

Thomson, et al., "New immunosuppressive drugs: mechanistic insights and potential therapeutic advances", Immunol. Rev., 136:71-98 (1993).

Turnquist, et al., "Rapamycin-Conditioned Dendritic Cells Are Poor Stimulators of Allogeneic CD4+ T Cells, but Enrich for Antigen-Specific Foxp3+ T Regulatory Cells and Promote Organ Transplant Tolerance", J. Immunol., 178(11):7018-31 (2007).

Vignali, et al., "How regulatory T cells work", Nature Reviews Immunology, 8(7):523-532 (2008).

Wang, et al., "Effect of preparation conditions on the size and encapsulation properties of mPEG-PLGA nanoparticies simultaneously loaded with vincristine sulfate and curcumin", Pharm. Dev. Technol., 18(3):694-700 (2013).

Wilson, et al., "Dendritic cells constitutively present self antigens in their immature state in vivo and regulate antigen presentation by controlling the rates of MHC class II synthesis and endocytosis", Blood, 103(6):2187-2195 (2004).

Workman, et al., "The development and function of regulatory T cells", Cell. Mol. Life. Sci., 66(16):2603-2622 (2009).

Yallapu, et al., "Fabrication of curcumin encapsulated PLGA nanoparticles for improved therapeutic effects in metastatic cancer cells", J. Colloid. Interface. Sci., 351(1): 19-29 (2010).

(56) References Cited

OTHER PUBLICATIONS

Yeste, et al., "Nanoparticle-mediated codelivery of myelin antigen and a tolerogenic small molecule suppresses experimental autoimmune encephalomyelitis", Proc. Natl. Acad. Sci. U.S.A., 109(28):11270-11275 (2012).

Zanoni, et al., "Generation of mouse bone marrow-derived dendritic cells (BM-DCs)" (2009).

Zheng, et al., "IL-2 is essential for TGF-beta to convert naive CD4+CD25− cells to CD25+Foxp3+ regulatory T cells and for expansion of these cells", Journal of Immunology, 178(4):2016-27 (2007).

Zhu, et al., "CD4+ T-cell differentiation regulated by networks of cytokines and transcription factors", Immunol. Rev., 238(1):247-262 (2010b).

Zhu, et al., "Differentiation of effector CD4 T cell populations (*)", Annu. Rev. Immunol., 26:445-489 (2010a).

\* cited by examiner

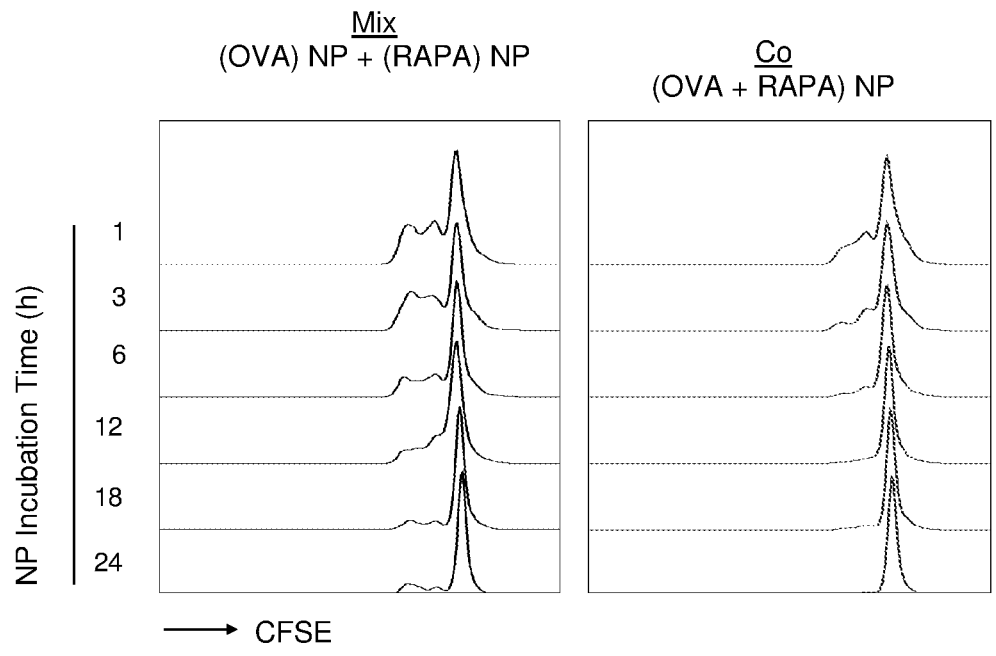
FIG. 7C FIG. 7D
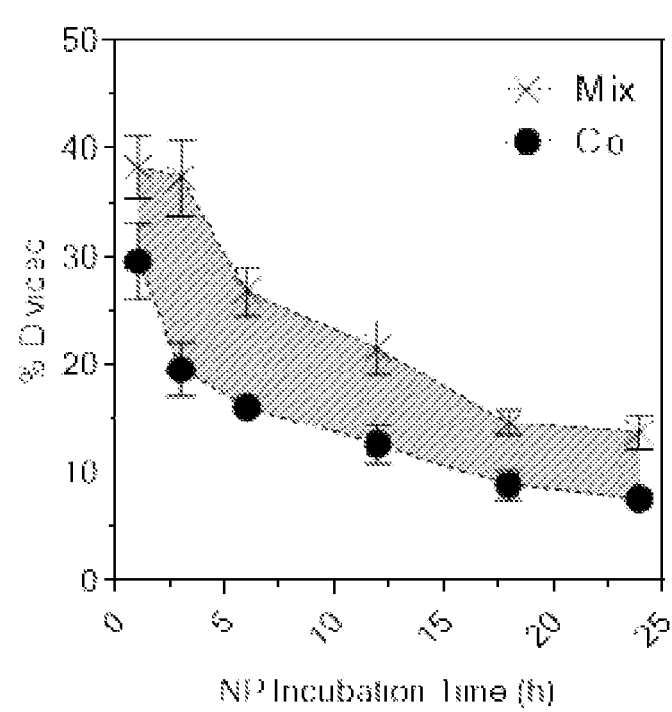
FIG. 7E

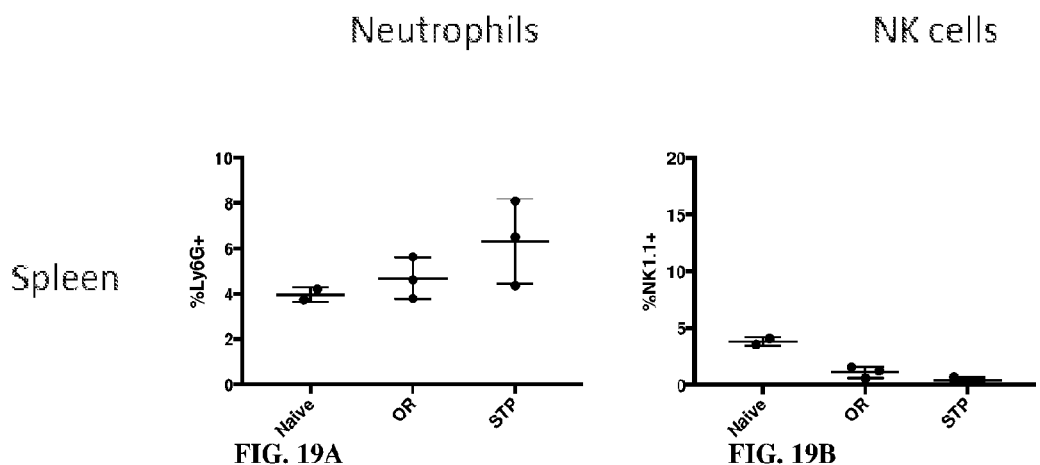
FIG. 19A  FIG. 19B
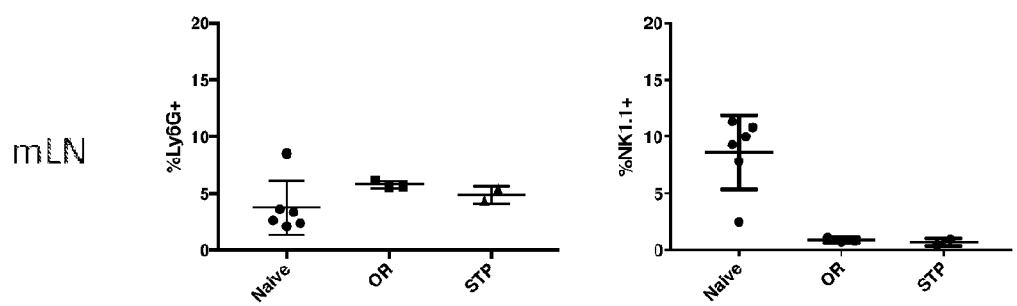
FIG. 19C  FIG. 19D
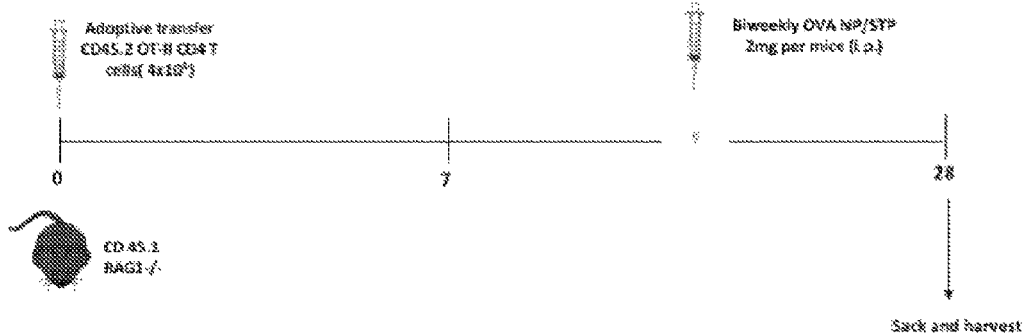
FIG. 20A

14 days 28 days

PARTICLES FOR SPATIOTEMPORAL RELEASE OF AGENTS

CROSS REFERENCE TO RELATED APPLICATIONS

This application is a National Phase application under 35 U.S.C. § 371 of PCT/US2019/031314, filed May 8, 2019, which claims priority to and the benefit of U.S. Provisional Application No. 62/669,242, filed May 9, 2018, which are hereby incorporated herein by reference in their entirety.

FIELD OF THE INVENTION

The invention is generally directed to nanoscale particles containing agents and providing spatial and/or temporal release of the agents, especially for optimal induction of tolerance.

BACKGROUND OF THE INVENTION

Controlled drug delivery technology represents one of the most rapidly advancing areas of science in which chemists and chemical engineers are contributing to human health care. Such delivery systems offer numerous advantages compared to conventional dosage forms including improved efficacy, reduced toxicity, and improved patient compliance and convenience. Such systems often use synthetic polymers as carriers for the drugs. By so doing, treatments that would not otherwise be possible are now in conventional use.

All controlled release systems aim to improve the effectiveness of drug therapy. This improvement can take the form of increasing therapeutic activity compared to the intensity of side effects, reducing the number of drug administrations required during treatment, or eliminating the need for specialized drug administration (e.g., repeated injections). Two types of control over drug release can be achieved, temporal and distribution control.

Bulk- and surface-eroding polymeric devices can serve as programmable biomolecule delivery systems to generate pulsatile release of one protein or sequential release of multiple biomolecules. Effective multi-pulse drug delivery system has been demonstrated using materials based on resorbable polyesters, polyanhydride-based laminates and crosslinked hydro gels. Microspheres have been developed for spatiotemporal bone morphogenic protein 2 (BMP2) release, which use macrophages to improve microsphere degradation and BMP2 release (Annamalai et al, Biomaterials. 161:216-227 (2018)).

Spatial control of drugs is typically achieved through the selection of the particle composition, the type, location and amount of loading, targeting and masking of delivery. Temporal control of release is typically obtained through many of the same mechanisms, including use of biodegradable polymers, inclusion of excipients, control of porosity, and exposure to stimuli such as pH, enzymes and external stimuli such as light or ultrasound.

There are few options to control the spatiotemporal release of agents, such as drugs, immunogenic agents, and immunomodulatory agents. There remains a need for controlled drug delivery systems tuned to release agents at times and locations at or within cells best suited to improve treatment efficacy.

Therefore, it is the object of the present invention to provide particles with spatial and/or temporal release of agents maximizing treatment efficacy in a subject.

It is another object of the present invention to provide compositions containing particles with spatial and/or temporal release of agents to maximize treatment efficacy in a subject.

It is yet another object of the present invention to provide methods of making and using the particles with precise spatial and/or temporal release of agents.

SUMMARY OF THE INVENTION

It has been discovered that it is possible to enhance the induction of tolerance to an antigen, such as a food, insect, drug or self-antigen, by exposing the targeted dendritic cells ("DCs") first with immunomodulatory agent such as rapamycin, then the antigen to which tolerance is to be induced. Conversely, a vaccine response can be enhanced by exposing the targeted dendritic cells first to the antigen to which the response is to be induced, then to an immunostimulatory agent. In both situations, it is critical to treat the same cells with both the antigen and the immunomodulatory agent, within a short time frame, and for a defined duration, to enhance the response compared to that which is obtained by simultaneous administration of antigen and immunomodulatory agent, whether administered and released together in a single particle or by systemic intravenous administration of one agent, antigen or immunomodulatory agent, in combination with administration of a particle containing the other agent.

Based on this discovery, which recognizes the need not only to deliver agent to specific targeted cells ("spatial criticality") as well as the timing of the delivery ("temporal criticality"), spatiotemporally tuned particles (STPs) have been developed to have targeted delivery and distinct release kinetics for at least two agents, which can enhance treatment in a subject, especially induction of tolerance or immunostimulation where it is critical the antigen and immunomodulatory agent be introduced to the same cell in a critical order and time. Specifically, it is critical to provide to the same cell the tolerance inducing agent prior to the antigen, in order to maximize the response. Conversely, it is critical to provide to the same cell the antigen prior to the immunostimulant/adjuvant.

These particles are not limited to delivery of antigen and immunomodulatory agent. Targeting of the particle, which agents are encapsulated/bound where, within or on the particles, and the kinetics of release, are determined based on the disease or disorder to be treated.

A single STP typically includes a core polymeric particle containing at least a first agent; a tethering moiety such as avidin-biotin or a covalent linker attached to the core particle and at least a second agent, which is encapsulated, dispersed or complexed within a carrier such as a polymer, dendrimer or dextran/cyclodextrin. The agents may be therapeutic or prophylactic, optionally also including imaging agents. In preferred embodiments for inducing tolerance, the agents are an antigen such as a food, insect, self-, or drug that induces undesirable responses in the individual and a tolerogenic agent such as rapamycin. In preferred embodiments for inducing an immune response, the agents are antigen(s) and an immunostimulatory agent. The STPs may be formulated with a physiologically acceptable excipient or carrier for administration, typically by injection.

Generally, the release of the first agent and the release of the second agent, are complete within a time period between about minutes and weeks. In some aspects, the release of the first agent and the release of the second agent are complete within a time period of a few minutes, a few hours, a day, a few days, a week, two weeks, a month, two months or three months.

Methods of making the STPs have also been developed. Typically, the core particle of STP is a polymeric particle with a natural or a synthetic polymer, preferably biodegradable, such as a polyhydroxy acid like polylactic acid, polyglycolic acid, or copolymer thereof. Typically, the STP has a tethering moiety such as avidin-biotin or covalent linkage, which may include an extender, which is cleaved or dissociates at the site of delivery, for example, by enzymes present at the site of delivery. Generally, the STPs have an average particle size between 10 nm and 1000 nm, more preferably between 60 and 500 nm, more preferably between 60 and 400 nm for delivery to dendritic cells.

The STPs may be administered directly or in a composition, to treat a disease, such as cancer, modulate epigenetic transcription, modulate an immune response, or deliver other agents to the subject.

An STP for immune modulation typically includes the core particle with a polymer and an antigen or an immunomodulator; and a tethered particle with an immunomodulator or an antigen. Typically, STPs for inducing immune tolerance to an antigen in a subject include STPs with the core particles containing an antigen and the tethered particles containing an immunomodulator. Typically, particles for inducing immune stimulation to an antigen in a subject include particles with the core particle containing an immunomodulator and the tethered particle containing an antigen. The antigen may be a B-cell antigen and/or a T cell antigen. The immunomodulator may be an immunosuppressant or an immunostimulant.

STP is a nanoparticle platform that can be used for application in many diseases, especially in cancer and autoimmune diseases. In cancer, combinatory delivery can be enhanced using STP. For example, delivering TL-2 (an immunostimulatory cytokine that stimulates growth, activation, and function of immune cells such as tumor infiltrating lymphocytes (TILs)) and checkpoint inhibitors, one would want to first mitigate the immunosuppressive tumor microenvironment and Tregs by delivering checkpoint inhibitors first, and then IL-2 so that IL-2s can be more effectively delivered to TILs rather than to the immunosuppressive Tregs. To do so requires the right spatiotemporal conditions (checkpoint inhibitors first, then IL-2) and to the same spatial location (same cells and environment). Given that STPs are designed to deliver multiple agents at a different rate to the same space, STPs can be very potent in cancer immunotherapy. An STP for reducing one or more symptoms of a disease such as cancer, may include a particle with the core particle containing a cytokine for stimulating an immune response, and the tethered particle containing an inhibitor, such as a checkpoint inhibitor (such as inhibitors of PD-1/PD-L1 and CTLA-4/B7-1/B7-2, including atezolizumab, avelumab, durvalumab, pembrolizumab, or nivolumab), anti-neoplastic agents (such as doxorubicin, or paclitaxel), and/or cancer antigens.

An STP particle for modulating epigenetic transcription may include, in the core particle, proteins that activate the transcription factors, and demethylating transferases, such as Aza-5-cytidine, in the tethered particle. The STP may maximize disease treatment efficacy by providing transcription factors, which can properly bind to the DNA sites of interest at maximal efficiency. With these STPs, the aza-5-cytidine and activating proteins are delivered in the most effective spatiotemporal manner.

Typically, the compositions are used to deliver to specific cells the first agent and the second agent at an amount and timing of release effective to treat a disease or reduce one or more symptoms of a disease. When the composition is formulated for inducing immune tolerance to an antigen, the STPs may be designed to release into the targeted cells an effective amount of the immunomodulator first (first release), and, later, the effective amount of the antigen (second release), to tolerize the immune system to the antigen.

BRIEF DESCRIPTION OF THE DRAWINGS

In FIG. 6A, antigen and rapamycin are delivered to the same immature DC at the same time (RAPA$_E$/OVA$_E$ or RAPA$_L$/OVA$_L$), resulting in the formation of semi-mature DC and effector T cells. When rapamycin and antigen are delivered to DCs at the same time, there is slight production of IL-10 and TGF-β. Effector T cells and Tregs are both generated as a result of presentation of antigen to antigen-specific T cells. In FIG. 6B, antigen is delivered prior to rapamycin (RAPA$_L$/OVA$_E$) to the same DC cell, resulting in the formation of semi-mature DC and effector T cells. When antigen is delivered earlier than rapamycin to DCs, there is slight production of IL-10 and TGF-β. Effector T cells and Tregs are both generated as a result of presentation of antigen to antigen-specific T cells. In FIG. 6C, rapamycin is delivered prior to the delivery of the antigen (RAPA$_E$/OVA$_L$) to the same DC, resulting in a tolerogenic DC and an expansion or de novo production of regulatory T cells. When rapamycin is delivered prior to antigen to DCs, PD-L1$^+$ tolerogenic DCs are generated and there is a higher production of IL-10 and TGF-β. In this scenario, there is a higher production of Tregs and a greater tolerance effect. FIGS. 6A-6C demonstrate one of the temporal aspect of directing the immune response with STPs.

FIGS. 7A-7E are graphs showing the differences in regulatory T cell expansion (FIG. 7A), IL-2 secretion (FIG. 7B), or T cell division (FIGS. 7C, 7D, and 7E) when DC and T cells in co-culture are incubated with a mix of nanoparticles (NP) containing either antigen ovalbumin (OVA) or rapamycin (RAPA) (Mix), or with NP containing both OVA and RAPA in the same NP (Co). FIG. 7A shows percent expansion of CD4+CD25+FoxP3+ regulatory T cells in the presence of soluble OVA+RAPA in solution, or Mix, or Co, over incubation time (h). FIG. 7B is a graph showing secretion of mouse IL-2 (mIL-2) by CD4 OT-II T cells over time (h) when the cells are incubated with OVA NP, Mix, or Co. FIGS. 7C and 7D show the cell division plots for CD4 OT-II T cells incubated with Mix or Co over incubation time (h), and FIG. 7E is a graph of the percent divided (% Divided) CD4 OT-II T cells from FIGS. 7C and 7D. FIGS. 7A-7E demonstrate one of the spatial aspects of directing the immune response with STP.

FIG. 14C shows the percent change in YFP+ cells from the CD4+ GFP+ T cells when the animals (genotype shown in FIG. 14A) received control or STP with TGF-beta/IL-2/Butyrate in the same NP (as shown in FIG. 14B), p=0.0248. FIG. 14D shows the change in the number (#) of YFP+ GFP+ CD4+ T cells when the animals (genotype shown in FIG. 14A) received control or STP with TGF-beta/IL-2/Butyrate in the same NP (as shown in FIG. 14B), p=0.1365. FIG. 14E shows the change in the percent (%) of YFP+ GFP+ CD4+ T cells when the animals (genotype shown in FIG. 14A) received control or STP with TGF-beta/IL-2/Butyrate in the same NP (as shown in FIG. 14B), p=0.0914. N>4; p-value was calculated by student t-test.

FIGS. 19A-19D are graphs showing percent population of neutrophils (Ly6G+) and NK cells (NK1.1+) from spleen (FIGS. 19A and 19B) and mesenteric lymph nodes (FIGS. 19C and 19D) (gated from Lin:–) (statistical significance was determined by student t-test). Cells were harvested as described for FIGS. 18A-18D.

FIG. 20A is a diagram showing the scheme of OVA NP or STP injection in adoptively transferred CD4 T cells in RAG1$^{-/-}$ mice.

DETAILED DESCRIPTION OF THE INVENTION

I. Definitions

Figure 1A:
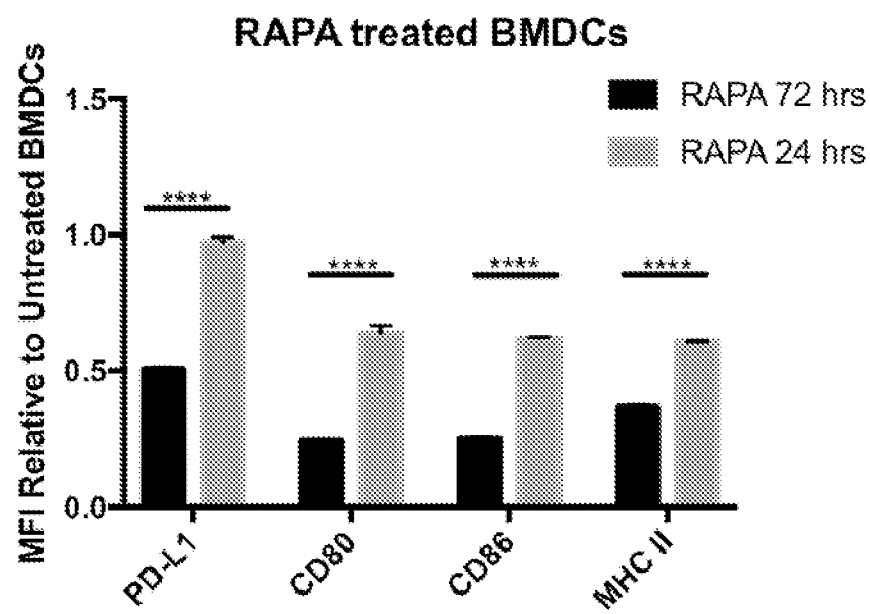
FIGS. 1A and 1B are graphs showing relative expression (Mean Fluorescent Intensity (MFI) Relative to Untreated BMDCs) of PD-L1, CD80, CD86, and MHCII in bone marrow-derived dendritic cells (BMDCs) treated with Rapamycin (RAPA, for 72 hours or 24 hours, FIG. 1A), Ovalbumin (OVA, for 72 hours or 24 hours, FIG. 1B). Isolated and cultured BMDCs were treated with either rapamycin (100 ng/ml) or whole OVA protein (10 μg/ml) for either 72 hours or 24 hours. Cells were then harvested and surface markers of DCs were analyzed by FACS. Graphs show the relative MFI of BMDC surface markers, normalized to MFI of untreated BMDCs. Untreated BMDCs or cells treated with Blank Nanoparticles show no change in the surface expression of PD-L1, CD80, CD86, and MHCII.

As used herein, the term "particle" generally refers to STP, which is a nanoscale particle, i.e., nanoparticle, having overall dimensions below one micrometer. The particle is typically a combination of a plurality of tethered particles tethered to, attached to, or associated with, a single core particle. The attachment may be through a tethering moiety.

As used herein, the term "spatial" in the context of release refers to spatially separated release of one, two, or more agents from the same particle. Spatially separated release of agents may be a release from two or more separate regions of a particle. Spatially separated release of agents may be a release at two or more anatomical regions in a subject. Spatially separated release of agents may be a release from two or more separate regions of a particle and a release at two or more anatomical regions in a subject from the same particle.

As used herein, the term "temporal" or "timing" in the context of release refers to a timing of release of one, two, or more agents from the same particle. The timing of release of the one, two, or more agents from the same particle may overlap with each other, may not overlap with each other, or may be separated from each other with a time gap, the time gap lasting seconds, minutes, hours, days, or weeks.

As used herein, the terms "biocompatible" and "biologically compatible" generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

As used herein, the term "biodegradable Polymer" generally refers to a polymer that will degrade or erode by enzymatic action and/or hydrolysis under physiologic conditions to smaller units or chemical species that are capable of being metabolized, eliminated, or excreted by the subject. The degradation time is a function of polymer composition, morphology, such as porosity, particle dimensions, and environment.

As used herein, the term "amphiphilic" refers to a property where a molecule has both a hydrophilic portion and a hydrophobic portion. Often, an amphiphilic compound has a hydrophilic portion covalently attached to a hydrophobic portion. In some forms, the hydrophilic portion is soluble in water, while the hydrophobic portion is insoluble in water. In addition, the hydrophilic and hydrophobic portions may have either a formal positive charge, or a formal negative charge. However, overall they will be either hydrophilic or hydrophobic. An amphiphilic compound can be an amphiphilic polymer, such that the hydrophilic portion can be a hydrophilic polymer, and the hydrophobic portion can be a hydrophobic polymer.

As used herein, the term "hydrophilic" refers to the property of having affinity for water. For example, hydrophilic polymers (or hydrophilic polymer segments) are polymers (or polymer segments) that are primarily soluble in aqueous solutions and/or have a tendency to absorb water. In general, the more hydrophilic a polymer is, the more that polymer tends to dissolve in, mix with, or be wetted by water. Hydrophilicity can be quantified by measuring its partition coefficient between water (or a buffered aqueous solution) and a water-immiscible organic solvent, such as octanol, methylene chloride, or methyl tert-butyl ether. If after equilibration a greater concentration of the compound is attained in water than in the organic solvent, then the compound is considered hydrophilic. For example, if the organic solvent is octanol, then a negative log P value indicates that the compound is hydrophilic. "Hydrophilic" may also refer to a material that when applied to a surface, such as glass, forms a contact angle with water, which is less than the contact angle of water on a surface of glass without the material.

As used herein, the term "hydrophobic" refers to the property of lacking affinity for or repelling water. For example, the more hydrophobic a polymer (or polymer segment), the more that polymer (or polymer segment) tends to not dissolve in, not mix with, or not be wetted by water. Hydrophobicity can be quantified by measuring its partition coefficient between water (or a buffered aqueous solution) and a water-immiscible organic solvent, such as octanol, methylene chloride, or methyl tert-butyl ether. If after equilibration a greater concentration of the compound is attained in the organic solvent than in water, the compound is considered hydrophobic. For example, if the organic solvent is octanol, then a positive log P value indicates that the compound is hydrophobic. "Hydrophobic" may also refer to a material that when applied to a surface, such as glass, forms a contact angle with water, which is greater than the contact angle of water on a surface of glass without the material.

Hydrophilicity and hydrophobicity can also be quantitated in relative terms, such as, but not limited to, a spectrum of hydrophilicity/hydrophobicity within a group of polymers or polymer segments. In some forms wherein two or more polymers are being discussed, the term "hydrophobic polymer" can be defined based on the polymer's relative hydrophobicity when compared to another, more hydrophilic polymer.

As used herein, the terms "average particle size" or "mean particle size," refer to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

As used herein, the term "pharmaceutically acceptable" refers to compounds, carriers, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the terms "encapsulated" and "incorporated" are art-recognized when used in reference to one or more agents, or other materials, into a polymeric composition. In certain embodiments, these terms include incorporating, formulating, or otherwise including such agent into a composition that allows for release, such as sustained release, of such agent in the desired application. The terms contemplate any manner by which an agent or other material is incorporated into a polymeric particle, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of more than one active agent or other material and at least one other agent or other material in a subject composition.

As used herein, the terms "inhibit" and "reduce" refer to reducing or decreasing activity, expression, or a symptom. This can be a complete inhibition or reduction of in activity, expression, or a symptom, or a partial inhibition or reduction. Inhibition or reduction can be compared to a control or to a standard level. Inhibition can be 1 to 100%, or any value therebetween, reduction in activity, expression, or a symptom relative to a control.

As used herein, the terms "treatment" or "treating" refer to administering a composition to a subject or a system to treat one or more symptoms of a disease. The effect of the administration of the composition to the subject can be, but is not limited to, the cessation of a particular symptom of a condition, a reduction or prevention of the symptoms of a condition, a reduction in the severity of the condition, the complete ablation of the condition, a stabilization or delay of the development or progression of a particular event or characteristic, or minimization of the chances that a particular event or characteristic will occur.

As used herein, the terms "prevent", "preventing", "prevention", and "prophylactic treatment" refer to the administration of an agent or composition to a clinically asymptomatic individual who is at risk of developing, susceptible, or predisposed to a particular adverse condition, disorder, or disease, and thus relates to the prevention of the occurrence of symptoms and/or their underlying cause.

As used herein, the term "agent" refers to a physiologically or pharmacologically active substance that acts locally and/or systemically in the body. An active agent is a substance that is administered to a patient for the treatment (e.g., therapeutic agent), prevention (e.g., prophylactic agent), nutrition supply (e.g., nutraceutical), or diagnosis (e.g., diagnostic agent) of a disease or disorder. The term also encompasses pharmaceutically acceptable, pharmacologically active derivatives of agents, including, but not limited to, salts, esters, amides, prodrugs, active metabolites, and analogs.

As used herein, the term "small molecule" generally refers to an organic molecule that is less than about 2000 g/mol in molecular weight, less than about 1500 g/mol, less than about 1000 g/mol, less than about 800 g/mol, or less than about 500 g/mol. In some forms, small molecules are non-polymeric and/or non-oligomeric.

As used herein, the terms "subject," "individual," and "patient" refer to any individual who is the target of treatment using the disclosed particles and compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

As used herein, the term "immunomodulator" refers to an agent that modulates an immune response to an antigen but is not the antigen or derived from the antigen. "Modulate", as used herein, refers to inducing, enhancing, suppressing, tolerizing, directing, or redirecting an immune response. Immunomodulator may be a therapeutic agent, a prophylactic agent, or a nutraceutical agent.

As used herein, the terms "effective amount" and "therapeutically effective amount," are used interchangeably, as applied to the nanoparticles, therapeutic agents, and pharmaceutical compositions described herein, and refer to the quantity necessary to render the desired therapeutic result. For example, an effective amount is a level effective to treat, cure, or alleviate the symptoms of a disease for which the composition and/or therapeutic agent, or pharmaceutical composition, is/are being administered. Amounts effective for the particular therapeutic goal sought will depend upon a variety of factors including the disease being treated and its severity and/or stage of development/progression; the bioavailability and activity of the specific compound and/or antineoplastic, or pharmaceutical composition, used; the route or method of administration and introduction site on the subject.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approximately +/−10%, +/−5%; +/−2%; or +/−1%.

II. Particles and Compositions

The spatiotemporally tuned particles (STPs) provide an efficient platform that can be applied in different settings with modifications to incorporate different agents, such as therapeutics, antigens, or immunomodulatory factors as needed.

The development of a single platform that delivers agents at a different rate could be universally used in any disease treatments. This would reduce the need to localize the therapeutics for the combined therapies to the same anatomical location, as well as frequency of administration of the therapeutics. The efficacy of the treatment may be enhanced because of the tuning of the STPs' spatiotemporal release profile with the required therapy.

As the Examples show, the technical advantages of the STPs include:

a. realization of the kinetics of delivery in antigen-specific tolerance induction and maintenance, b. realization that the spatial localization is important to achieve effective antigen-specific tolerance, c. the ability to stagger the release of multiple agents from a single nanoparticle platform, d. the ability to deliver a combination of factors to the same cell (e.g., APC), e. the ability to tune the temporal and spatial release, f. the ability to expand the use of STPs to all drugs, biologics, and macromolecules etc., and g. multi-valency: this factor highlights the importance of the platform. Typically, molecules that are guests in cyclodextrins have a low guest-host affinity on the order of K~µM or mM interactions, making it especially challenging for the drug to stay intact with the platform as it navigates though bodily fluids. However, because hundreds of cyclodextrins coat the biodegradable or non-biodegradable particle the affinity of the guest to its target is significantly increased due to avidity made possible by the many copies of the loaded cyclodextrin on the surface. Further cyclodextrins enhance the stability of other cyclodextrins through non-covalent interactions, making it possible to achieve higher stability of the host on particles versus individual hosts without particles. Because the affinity is high, a smaller dose of the drug is required for efficacy, such as a reduction by a factor of 10 to 1000 in the drug concentration needed to achieve efficacy compared to the soluble drug.

Preferably, the STPs have one or more agents in the core of the particle and one or more agents guest-hosted by complexes, such as cyclodextrin complexes, attached to the surface of the core particles. This allows the cyclodextrin complex guest to be delivered to the same space or cell but at a faster rate than the encapsulant in the core, which requires biodegradation or diffusion to release to the outside environment.

A. Spatiotemporally Tuned Particles

Figure 8A:
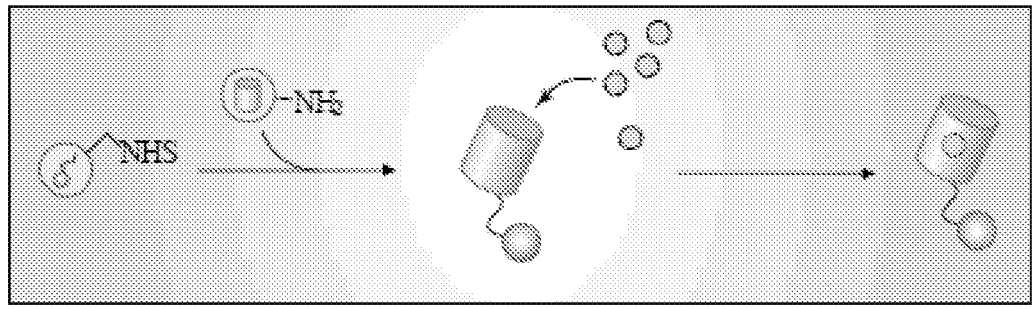
FIGS. 8A and 8B are diagrams showing the steps in forming the tethering moiety and the tethered particle of STP (FIG. 8A) and the structure of STP with the core particle 10, the tethering moiety 20, and the tethered particles 30 (FIG. 8B).
Figure 8B:
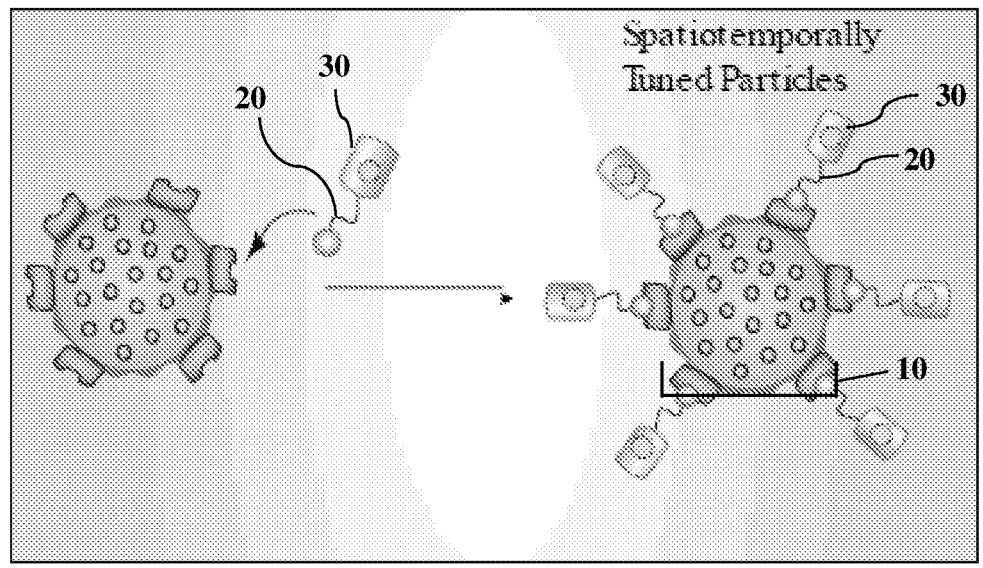

The particles for spatial and/or temporal release of agents include a core particle having a plurality of one or more agents bound thereto via a tethering moiety such as avidin-biotin, a covalent linkage or a covalent linker, where the agents are encapsulated in, dispersed within, bound to, or complexed within a carrier such as a polymeric particle, dendrimer, ionic complex such as a dextran or cyclodextrin, or agent such as carbon nanotubes (collectively referred to herein as "tethered particles"). A schematic of an exemplary particle is presented in FIG. 8B. The spatiotemporally tuned particles (STP) include a core particle 10, the tethering moiety 20, and the tethered particles 30 (FIG. 8B).

Generally, the particles including tethered agents have an average diameter between about 10 nm and about 1000 nm, such as between about 50 nm and about 950 nm, between about 100 nm and about 800 nm, between about 100 nm and about 850 nm, between about 100 nm and about 750 nm, between about 100 nm and about 700 nm, between about 100 nm and about 650, between about 100 nm and about 600 nm, between about 100 nm and about 550 nm, between about 100 nm and about 500 nm, between about 100 and about 450 nm, between about 100 nm and about 400 nm, between about 100 nm and about 350 nm, or between about 100 nm and about 300 nm. In some aspects, the particles have an average diameter between about 100 nm and about 500 nm, between about 100 and about 450 nm, between about 100 nm and about 400 nm, between about 100 nm and about 350 nm, or between about 100 nm and about 300 nm, such as about 150 nm, about 200 nm, about 250 nm, about 300 nm, or about 350 nm.

The particle size may be measured with any suitable method. Suitable methods include dynamic light scattering (DLS), cryogenic-transmission electron microscopy (cryo-TEM), small angle x-ray scattering (SAXS), or small angle neutron scattering (SANS).

1. Core Particle

Typically, the core particle is a polymeric particle containing at least one agent encapsulated and/or dispersed therein. The core particle may also include crosslinking moieties to link the core particle with the tethering moiety, or the core particle with the tethered particle. Generally, the core particle is a sphere, or any other regular or irregular three-dimensional nanoscale-shaped object with an overall average diameter between about 10 nm and about 900 nm, similar to the size of the particle including the tethered agent. The diameter may be a hydrodynamic diameter or a physical diameter.

The average diameter of a plurality of core particles may be between about 10 nm and about 900 nm, such as between about 100 nm and about 850 nm, between about 100 nm and about 750 nm, between about 100 nm and about 700 nm, between about 100 nm and about 650 nm, between about 100 nm and about 600 nm, between about 100 nm and about 550 nm, between about 100 nm and about 500 nm, between about 100 nm and about 450 nm, between about 100 nm and about 400 nm, between about 100 nm and about 350 nm, or between about 100 nm and about 300 nm. In some aspects, the particles have an average diameter between about 100 nm and about 450 nm, between about 100 nm and about 400 nm, between about 100 nm and about 350 nm, or between about 100 nm and about 300 nm, such as about 100 nm, about 150 nm, about 200 nm, about 250 nm, or about 300 nm.

The size of the core particle may be measured with any suitable method prior to attachment of the tethering moiety and/or the tethered particle. Suitable methods include dynamic light scattering (DLS), cryogenic-transmission electron microscopy (cryo-TEM), small angle x-ray scattering (SAXS), or small angle neutron scattering (SANS).

a. Polymers

The polymeric matrix of the core particle may be formed from one or more polymers, copolymers or blends. By varying the composition and morphology of the polymeric matrix, one can achieve a variety of controlled release characteristics, permitting the delivery of moderate constant doses of one or more active agents over prolonged periods of time. Preferably, the polymeric matrix is biodegradable. The polymeric matrix can be selected to degrade within a time period between one day and one year, more preferably between one day and 26 weeks, more preferably between one days and 20 weeks, most preferably between one day and 4 weeks. In some aspects, the polymeric matrix can be selected to degrade within a time period between few hours and 5 weeks, more preferably between one day and 3 weeks, more preferably between one day and 15 days, most preferably between one day and seven days.

In general, synthetic polymers are preferred, although natural polymers may be used. Representative polymers include polyhydroxy acids (poly(lactic acid), poly(glycolic acid), poly(lactic acid-co-glycolic acids)), polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); poly(glycolide-co-caprolactones); polycarbonates such as tyrosine polycarbonates; polyamides (including synthetic and natural polyamides), polyvinyl alcohols, polyvinylpyrrolidone; poly(alkylene oxides) such as polyethylene glycol (PEG) and pluronics (polyethylene oxide polypropylene glycol block copolymers), polyacrylic acids, as well as derivatives, copolymers, and blends thereof.

As used herein, "derivatives" include polymers having substitutions, additions of chemical groups and other modifications to the polymeric backbones described above routinely made by those skilled in the art. Natural polymers, including proteins such as albumin, collagen, gelatin, prolamines, such as zein, and polysaccharides such as alginate and pectin, may also be incorporated into the polymeric matrix. In certain cases, when the polymeric matrix contains a natural polymer, the natural polymer is a biopolymer which degrades by hydrolysis.

In some aspects, the polymeric matrix of the core particle may contain one or more crosslinkable polymers. The crosslinkable polymers may contain one or more photo-polymerizable groups, allowing for the crosslinking of the polymeric matrix following particle formation. Examples of suitable photo-polymerizable groups include vinyl groups, acrylate groups, methacrylate groups, and acrylamide groups. Photo-polymerizable groups, when present, may be incorporated within the backbone of the crosslinkable polymers, within one or more of the sidechains of the crosslinkable polymers, at one or more of the ends of the crosslinkable polymers, or combinations thereof.

The polymeric matrix of the core particle may be formed from polymers having a variety of molecular weights, so as to form particles having properties, including drug release rates, effective for specific applications.

In some embodiments, the polymeric matrix is formed from an aliphatic polyester or a block copolymer containing one or more aliphatic polyester segments. Preferably the polyester or polyester segments are poly(lactic acid) (PLA), poly(glycolic acid) PGA, or poly(lactide-co-glycolide) (PLGA). The degradation rate of the polyester segments, and often the corresponding drug release rate, can be varied from days (in the case of pure PGA) to months (in the case of pure PLA), and may be readily manipulated by varying the ratio of PLA to PGA in the polyester segments. In addition, PGA, PLA, and PLGA have been established as safe for use in humans; these materials have been used in human clinical applications, including drug delivery system, for more than 30 years.

Examples of preferred natural polymers include proteins such as albumin, collagen, gelatin and prolamines, for example, zein, and polysaccharides such as alginate, chitosan, cellulose, carboxymethyl cellulose (CMC), cellulose derivatives, and polyhydroxyalkanoates, for example, polyhydroxybutyrate. The in vivo stability of the particles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

Examples of preferred non-biodegradable polymers include ethylene vinyl acetate, poly(meth)acrylic acid, polyamides, copolymers and mixtures thereof. Examples of preferred biodegradable polymers include polyester or polyester segments poly(lactic acid) (PLA), poly(glycolic acid) PGA, or poly(lactide-co-glycolide) (PLGA).

2. Tethering Moieties, Covalent Linkages and Linkers a. First Agent and Second Agent The core particles and the tethered particle may include one or more pharmaceutical agents listed above in any combination.

The amount of each agent in the particle may be between 0.00001% by weight and 50% by weight, between 0.0001% by weight and 50% by weight, between 0.001% by weight and 50% by weight, or between 0.01% by weight and 50% by weight of the particle.

Any agent, or any combination of the agents may be included in the core particle, in the tethered particle, or both in the core particle and in the tethered particle.

For example, particles suitable for inducing antigen-specific tolerance may incorporate one or more immunomodulators, such as one or more immunosuppressants, in the tethered particle, and one or more antigens, self-antigens, xenoantigens, allergens, etc., against which an immune tolerance is desired, in the core particle. In particles for cancer treatment, the particles may be for combinatorial delivery of agents (such as checkpoint inhibitors) and cytokine (such as IL-2) in cancer immunotherapy. The particles may be used to deliver checkpoint inhibitors first and IL-2 at a later time to the same spatial location. The earlier release of checkpoint inhibitors would inhibit suppressive Tregs in the tumor microenvironment and increase IL-2 availability specifically to tumor-infiltrating lymphocytes (TILs).

3. Linking Moieties

The core particle may include one or more linking moieties for linking the tethered particle, the tethering moiety, or linking the tethering moiety attached to the tethered particle to the core particle.

Examples of linking moieties include avidin, neutravidin, streptavidin, biotin, and any one of the crosslinking molecules described in Tables 1 and 2.

Suitable crosslinking agents on the tethering moieties are disclosed in Tables 1 and 2 below. Other suitable crosslinking agents include avidin, neutravidin, streptavidin, and biotin.

The particles may be functionalized using any suitable chemical modifications of the additives in the continuous matrix. An example is a copper-free click chemistry that can be used to functionalize the surface of the particles to bind any ligand or moiety of interest, including linkers, peptides, antibodies, and fluorescent or radiolabeled reporter molecules.

In preferred embodiments, particles containing a tethering moiety and/or a tethered particle, may have linking moieties on the surface to link the tethering moiety to the core particle, the tethered particle to the core particle, the tethering moiety to the tethered particle, or the tethering moiety and the tethered particle to the core particle. The linking moieties may be proteins, peptides, or small molecules or short polymers. The linking moieties may be crosslinking agents. Crosslinking agents are categorized by their chemical reactivity, spacer length, and materials.

TABLE 1

Reactive groups of crosslinking agents

| Reactivity Class (Reactive group) | Chemical Group of Crosslinking Agent |
|---|---|
| Carboxyl-to-amine Amine | Carbodiimide (e.g. EDC) NHS ester, Imidoester, Pentafluorophenyl ester, Hydroxymethyl phosphine |
| Sulfhydryl | Maleimide, Haloacetyl (Bromo- or Iodo-) Pyridyldisulfide, Thiosulfonate, Vinylsulfone |
| Aldehyde (i.e. oxidized sugars, carbonyls) | Hydrazide, Alkoxyamine |
| Photoreactive groups (i.e. nonselective, random insertion) | Diazine, Aryl Azide |
| Hydroxyl (non-aqueous) | Isocyanate |

TABLE 2

Hetero-bi-functional cross-linkers

| Linker | Reactive Toward | Advantages |
|---|---|---|
| SMPT | Primary amines Sulfhydryls | Great stability |
| SPDP | Primary amines Sulfhydryls | Thiolation Cleavable cross-linker |
| LC-SPDP | Primary amines Sulfhydryls | Extended spacer arm |
| Sulfo-LC-SPDP | Primary amines Sulfhydrylss | Extended spacer arm; water soluble |
| SMCC | Primary amines Sulfhydryls | Stable maleimide reactive group; |
| Sulfo-SMCC | Primary amines Sulfhydryls | Stable maleimide reactive group; water soluble |
| MBS | Primary amines Sulfhydryls | |
| Sulfo-MBS | Primary amines Sulfhydryls | Water soluble |
| SIAB | Primary amines Sulfhydryls | |
| Sulfo-SIAB | Primary amines Sulfhydryls | Water soluble |
| SMPB | Primary amines Sulfhydryls | Extended spacer arm |
| Sulfo-SMPB | Primary amines Sulfhydryls | Extended spacer arm; water soluble |
| EDC/Sulfo-NHS | Primary amines Carboxyl groups | |
| ABH | Carbohydrates Nonselective | Reactive with sugar groups |

4. Tethered Particle

The particle typically includes a tethered particle for initial release of agent, with the core particle being used for later release of a different agent.

The tethered particle typically includes an agent in association with a compound that readily dissolves or dissociates in an aqueous environment, releasing the agent. The association of the agent with the compound in the tethered particle may be a guest-host relationship.

Typically, the tethered particle has a size between about 0.1 nm and about 200 nm, such as between about 0.1 nm and about 175 nm, between about 0.1 nm and about 150 nm, between about 0.1 nm and about 125 nm, between about 0.1 nm and about 100 nm, between about 0.1 nm and about 75 nm, or between about 0.1 nm and about 50 nm. Suitable smaller ranges include between about 10 nm and about 200 nm, between about 10 nm and about 175 nm, between about 10 nm and about 150 nm, between about 10 nm and about 125 nm, between about 10 nm and about 100 nm, between about 10 nm and about 75 nm, between about 1 nm and about 50 nm, between about 5 nm and about 50 nm, or between about 10 nm and about 50 nm.

Generally, the tethered particle may have an irregular globular or spherical shape, or may be presented as an aggregate of a plurality of globular or spherical shapes.

The size of the tethered particle may be measured with any suitable method. Suitable methods include dynamic light scattering (DLS), cryogenic-transmission electron microscopy (cryo-TEM), small angle x-ray scattering (SAXS), or small angle neutron scattering (SANS).

The particles may be polymeric particles, complexes of materials such as cyclodextrin and dendrimers, or carbon nanotubes.

a. Polymeric Particles

Polymeric particles can be used for delivery of the initial agent. These may be made with the same or different polymers as the polymer core, preferably with high loading of the agent for rapid release, either on the surface or within a porous particle. The particles may also be formed of the agent for initial delivery.

b. Cyclodextrins and Guest-Host Complexes and Carbon Nanotubes

In certain embodiments, the host molecule is a cyclodextrin. Cyclodextrins are cyclic oligosaccharides containing six (α-cyclodextrin), seven (β-cyclodextrin), eight (γ-cyclodextrin), or more α-(1,4)-linked glucose residues. The hydroxyl groups of the cyclodextrins are oriented to the outside of the ring while the glucosidic oxygen and two rings of the non-exchangeable hydrogen atoms are directed towards the interior of the cavity. As a result, cyclodextrins possess a hydrophobic inner cavity combined with a hydrophilic exterior. Upon combination with a hydrophobic active agent, the active agent (i.e., the guest) inserts into the hydrophobic interior of the cyclodextrin (i.e., the host).

The cyclodextrin may be chemically modified such that some or all of the primary or secondary hydroxyl groups of the macrocycle, or both, are functionalized with one or more pendant groups. The pendant groups may be reactive functional groups that can react with the polymeric matrix, such as methacrylates, acrylates, vinyl groups, epoxides, thiiranes, azides, alkynes, and combinations thereof. The pendant groups may also serve to modify the solubility of the cyclodextrin. Exemplary groups of this type include sulfinyl, sulfonyl, phosphate, acyl, and $C_1$-$C_{12}$ alkyl groups optionally substituted with one or more (e.g., 1, 2, 3, or 4) hydroxy, carboxy, carbonyl, acyl, oxy, and oxo groups. Methods of modifying these alcohol residues are known in the art, and many cyclodextrin derivatives are commercially available.

Examples of suitable cyclodextrins include α-cyclodextrin; β-cyclodextrin; γ-cyclodextrin; methyl α-cyclodextrin; methyl β-cyclodextrin; methyl γ-cyclodextrin; ethyl β-cyclodextrin; butyl α-cyclodextrin; butyl β-cyclodextrin; butyl γ-cyclodextrin; pentyl γ-cyclodextrin; hydroxy ethyl β-cyclodextrin; hydroxyethyl γ-cyclodextrin; 2-hydroxypropyl α-cyclodextrin; 2-hydroxypropyl β-cyclodextrin; 2-hydroxypropyl γ-cyclodextrin; 2-hydroxybutyl β-cyclodextrin; acetyl α-cyclodextrin; acetyl β-cyclodextrin; acetyl γ-cyclodextrin; propionyl β-cyclodextrin; butyryl β-cyclodextrin; succinyl α-cyclodextrin; succinyl β-cyclodextrin; succinyl γ-cyclodextrin; benzoyl β-cyclodextrin; palmityl β-cyclodextrin; toluenesulfonyl β-cyclodextrin; acetyl methyl β-cyclodextrin; acetyl butyl β-cyclodextrin; glucosyl α-cyclodextrin; glucosyl β-cyclodextrin; glucosyl γ-cyclodextrin; maltosyl α-cyclodextrin; maltosyl β-cyclodextrin; maltosyl γ-cyclodextrin; α-cyclodextrin carboxymethylether, β-cyclodextrin carboxymethylether, γ-cyclodextrin carboxymethylether, carboxymethylethyl β-cyclodextrin; phosphate ester α-cyclodextrin; phosphate ester β-cyclodextrin; phosphate ester γ-cyclodextrin; 3-trimethylammonium-2-hydroxypropyl β-cyclodextrin; sulfobutyl ether β-cyclodextrin; carboxymethyl α-cyclodextrin; carboxymethyl β-cyclodextrin; carboxymethyl γ-cyclodextrin, and combinations thereof.

Preferred cyclodextrins include α-cyclodextrins, β-cyclodextrins, and γ-cyclodextrins functionalized with one or more pendant acrylate or methacrylate groups. In a particular embodiment, the host molecule is a β-cyclodextrin functionalized with multiple methacrylate groups. An exemplary host molecule of this type is illustrated below, wherein R represents a $C_1$-$C_6$ alkyl group.

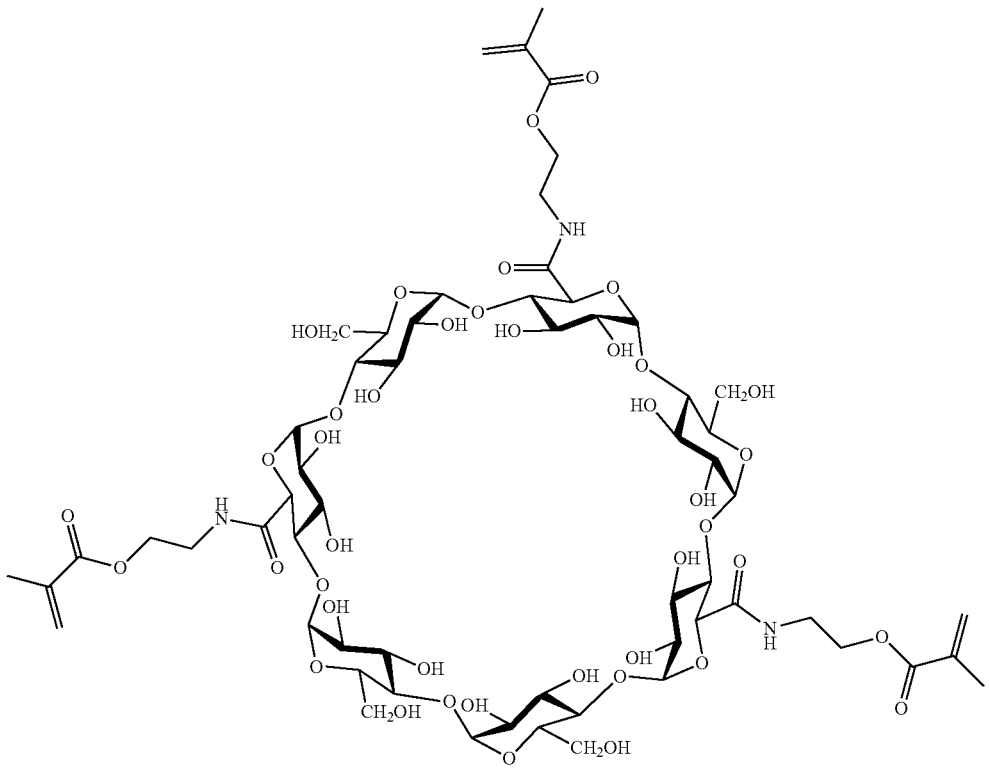 [SMILES: C=C(C)C(=O)OCCNC(=O)C1OC2O[C@@H]3C(CO)O[C@H](O[C@@H]4C(C(=O)NCCOC(=O)C(=C)C)O[C@H](O[C@@H]5C(CO)O[C@H](O[C@@H]6C(CO)O[C@H](O[C@@H]7C(C(=O)NCCOC(=O)C(=C)C)OC(O[C@@H]8C(CO)O[C@H](O[C@H]1[C@H](O)[C@@H]2O)C(O)[C@H]8O)[C@@H](O)[C@H]7O)C(O)[C@H]6O)C(O)[C@H]5O)C(O)[C@H]4O)C(O)[C@H]3O]

As a further example, the host molecule may also be a material that temporarily associates with an active agent via ionic interactions. For example, conventional ion exchange resins known in the art for use in controlled drug release may serve as host molecules. See, for example, Chen, et al., *J. Pharm. Pharmacol.* 44(3):21 1-215 (1992) and Farag, et al., *J. Pharm. Sci.* 77(10):872-875(1988).

When the active agent being delivered is a cationic species, suitable ion exchange resins may include a sulfonic acid group (or modified sulfonic acid group) or an optionally modified carboxylic acid group on a physiologically acceptable scaffold. Similarly, where the active agent is an anionic species, suitable ion exchange resins may include amine-based groups (e.g., trimethylamine for a strong interaction, or dimethylethanolamine for a weaker interaction).

In some cases, the host molecule is a molecule that forms an inclusion complex with an agent. Inclusion complexes are formed when an active agent (i.e., the guest), or portion of an active agent, inserts into a cavity of another molecule, group of molecules, or material (i.e., the host). Typically, the guest molecule associates with the host molecule without affecting the framework or structure of the host. For example, in the case of inclusion complexes, the size and shape of the available cavity in the host molecule remain substantially unaltered as a consequence of complex formation.

The host molecule may be a small molecule, an oligomer, a polymer, or combinations thereof. Exemplary hosts include polysaccharides such as amyloses, cyclodextrins, and other cyclic or helical compounds containing a plurality of aldose rings, for example, compounds formed through 1,4 and 1,6 bonding of monosaccharides (such as glucose, fructose, and galactose) and disaccharides (such as sucrose, maltose, and lactose). Other exemplary host compounds include cryptands, cryptophanes, cavitands, crown ethers, dendrimers, ion-exchange resins, calixarenes, valinomycins, nigericins, catenanes, polycatenanes, carcerands, cucurbiturils, and spherands.

In other embodiments, organic host compounds or materials include carbon nanotubes, fullerenes, and/or graphene-based host materials. Carbon nanotubes (CNTs) are allotropes of carbon with a cylindrical nanostructure. Nanotubes are members of the fullerene structural family, which also includes the spherical buckyballs, and the ends of a nanotube may be capped with a hemisphere of the buckyball structure. Their name is derived from their long, hollow structure with the walls formed by one-atom-thick sheets of carbon, called graphene. These sheets are rolled at specific and discrete ("chiral") angles, and the combination of the rolling angle and radius decides the nanotube properties. Nanotubes can be categorized as single-walled nanotubes (SWNTs) and multi-walled nanotubes (MWNTs). Nanotubes and/or fullerenes can serve as hosts, for example, by encapsulating or entrapping the material to be delivered (i.e., the guest) within the tubes or fullerenes. Alternatively, the exterior and/or interior of the tubes and/or fullerenes can be functionalized with functional groups which can complex to the guest to be delivered. Complexations include, but are not limited to, ionic interactions, hydrogen bonding, Van der Waals interactions, and pi-pi interactions, such as pi-stacking.

Graphenes are also an allotrope of carbon. The structure of graphene is a one-atom-thick planar sheet of $sp^2$-bonded carbon atoms that are densely packed in a honeycomb crystal lattice. Graphene is the basic structural element of some carbon allotropes including graphite, charcoal, carbon nanotubes and fullerenes. The guest to be delivered can associate with and/or complex to graphene or functionalized graphene as described above for nanotubes and fullerenes.

The host material can also be an inorganic material, including but not limited to, inorganic phosphates and silica.

In order to form a complex with the active agent being delivered, the host molecule is generally selected to be complimentary to the active agent both in terms of sterics (size) and electronics (charge and polarity). For example, in the case of host molecules that form inclusion complexes with the active agent to be delivered, the host molecule will typically possess an appropriately-sized cavity to incorporate the active agent. In addition, the host molecule typically possesses a cavity of appropriate hydrophobicity/hydrophilicity to promote complex formation with the active agent. The strength of the guest-host interaction will influence the release profile of the agent from the tethered particle, with stronger guest-host interactions generally producing more prolonged drug release.

Cationic polymers, such as polyethyleneimine (PEI), can function as host molecules for complex oligonucleotides such as siRNA. In some embodiments the host molecule is a dendrimer conjugated to a cyclodextrin. In some embodiments, the cyclodextrin(s) shields primary amines of dendrimer.

c. Dendrimers

The term "dendrimer" as used herein includes, but is not limited to, a molecular architecture with an interior core, interior layers (or "generations") of repeating units regularly attached to this initiator core, and an exterior surface of terminal groups attached to the outermost generation. Examples of dendrimers include, but are not limited to, PAMAM, polyester, polylysinc, and PPI. The PAMAM dendrimers can have carboxylic, amine and hydroxyl terminations and can be any generation of dendrimers including, but not limited to, generation 1 PAMAM dendrimers, generation 2 PAMAM dendrimers, generation 3 PAMAM dendrimers, generation 4 PAMAM dendrimers, generation 5 PAMAM dendrimers, generation 6 PAMAM dendrimers, generation 7 PAMAM dendrimers, generation 8 PAMAM dendrimers, generation 9 PAMAM dendrimers, or generation 10 PAMAM dendrimers. Dendrimers suitable for use include, but are not limited to, polyamidoamine (PAMAM), polypropylamine (POPAM), polyethylenimine, polylysine, polyester, iptycene, aliphatic poly(ether), and/or aromatic polyether dendrimers. Each dendrimer of the dendrimer complex may be of similar or different chemical nature than the other dendrimers (e.g., the first dendrimer may include a PAMAM dendrimer, while the second dendrimer may comprise a POPAM dendrimer). In some embodiments, the first or second dendrimer may further include an additional agent. The multi-arm PEG polymer includes a polyethylene glycol having at least two branches bearing sulfhydryl or thiopyridine terminal groups; however, embodiments are not limited to this class and PEG polymers bearing other terminal groups such as succinimidyl or maleimide terminations can be used. The PEG polymers in the molecular weight 10 kDa to 80 kDa can be used.

A dendrimer complex includes multiple dendrimers. For example, the dendrimer complex can include a third dendrimer; wherein the third-dendrimer is complexed with at least one other dendrimer. Further, a third agent can be complexed with the third dendrimer. In another embodiment, the first and second dendrimers are each complexed to a third dendrimer, wherein the first and second dendrimers are PAMAM dendrimers and the third dendrimer is a POPAM dendrimer. Additional dendrimers can be incorporated without departing from the spirit of the invention. When multiple dendrimers are utilized, multiple agents can also be incorporated. This is not limited by the number of dendrimers complexed to one another.

As used herein, the term "PAMAM dendrimer" means poly(amidoamine) dendrimer, which may contain different cores, with amidoamine building blocks. The method for making them is known to those of skill in the art and generally, involves a two-step iterative reaction sequence that produces concentric shells (generations) of dendritic β-alanine units around a central initiator core. This PAMAM core-shell architecture grows linearly in diameter as a function of added shells (generations). Meanwhile, the surface groups amplify exponentially at each generation according to dendritic-branching mathematics. They are available in generations G0-10 with 5 different core types and 10 functional surface groups. The dendrimer-branched polymer may consist of polyamidoamine (PAMAM), polyglycerol, polyester, polyether, polylysine, or polyethylene glycol (PEG), polypeptide dendrimers.

In some embodiments, the dendrimers are in nanoparticle form and are described in detail in international patent publication No. WO2009/046446.

5. Agents

The agents are generally suitable as first agent(s) as well as second agent(s). The agents may be included in the core particle, in the tethered particles, or in both the core particle and in tethered particles.

The core particles typically include at least one agent, such as a first agent. The particle typically includes at least one rust agent and at least one second agent. The first agent and the second agent may be the same agent, different agents, or combinations of different agents. The agent may be a therapeutic and prophylactic, optionally further including diagnostic and imaging agent. These agents are pharmaceutical agents useful in preventing, treating, or diagnosing a disease or condition.

Therapeutic agents include synthetic and natural proteins (including enzymes, peptide-hormones, receptors, growth factors, antibodies, signaling molecules), and synthetic and natural nucleic acids (including RNA, DNA, anti-sense RNA, triplex DNA, inhibitory RNA (RNAi), and oligonucleotides), and biologically active portions thereof. Suitable agents include small molecule agents with molecular weight less than 1000 g/mol. Suitable protein agents have a size greater than about 1,000 Da for small peptides and polypeptides, more typically at least about 5,000 Da and often 10,000 Da or more for proteins. Nucleic acids are more typically listed in terms of base pairs or bases (collectively "bp"). Nucleic acids with lengths above about 10 bp, such as in the range from about 20 bp (probes; inhibitory RNAs, etc.) to tens of thousands of bp for genes and vectors, may be included as agents. The agents may also be hydrophilic molecules, preferably having a low molecular weight.

General classes of agents include those to induce tolerance or stimulate immunity to an antigen, and those for treatment of a disease or disorder such as cancer.

a. Antigens

Antigens include antigenic materials, such as infectious agents, pathogenic bacterial, viral, fungal, or self-antigens, or allergens. The antigens may be delivered to antigen presenting cells to induce immunological responses to, or suppress or tolerize an immunological response towards, the antigen in a subject in need thereof.

The antigens may be B-cell or T-cell antigens. Unlike T cells that recognize digested peptides, B cells recognize their cognate antigen in its native form. The B cell receptor used in recognition can also be secreted to bind to antigens and initiate multiple effector functions such as phagocytosis, complement activation, or neutralization of receptors. While B cells can interact with soluble antigens, the presentation of membrane-bound antigen plays an important role in B cell activation, and in particular during affinity-maturation, the process during which high-affinity B cells are selected (Balthasar et al., *Trends in Immunology*, 37(12):844-854 (2016)).

T cell antigens are usually peptides, with four to seven amino acid epitopes. B cell antigens can be proteins, peptides, or other molecules including metal, sugars and drugs, usually bound to a protein hapten.

Antigens to Induce Tolerance to

Autoimmune disease antigens include, but are not limited to, degenerative disease antigen, atopic disease antigen, autoimmune disease antigen, alloantigen, xenoantigen, allergens, drugs include addictive substances such as nicotine, metabolic disease enzymes, enzymatic products, anti-drug antibody, and vector antigens. Self-antigens include Rh blood group antigens, I antigen, Platelet integrin GpIIb:IIIa, noncollagenous domain of basement membrane collagen type IV, epidermal cadherin, streptococcal cell-wall antigens, antibodies cross-reacting with cardiac muscle, Rheumatoid factor IgG complexes with or without Hep C antigens, DNA, histones, ribosomes, snRNP, scRNP, pancreatic beta-cell antigen, synovial joint antigen, myelin basic protein, proteolipid protein, myelin oligodendrocyte glycoprotein, and thyroid peroxidase.

Anti-drug antibodies (ADA) may be generated against therapeutic monoclonal antibodies, glycosylated or PEGylated therapeutics, and therapeutic macromolecules with complex quaternary structure forming aggregates, DNA drugs, and vectors delivering drugs, such as adenoviral vectors.

ADA may neutralize the therapeutic effects of the drug and/or alter its pharmacokinetics. B cells are certainly involved in this immune response when IgG class ADA are observed, because antibody isotype switching is a hallmark of B-dependent antigens. Examples of adverse ADA responses include autoimmune thrombocytopenia (ITP) following exposure to recombinant thrombopoietin, and pure red cell aplasia, which was associated with a particular formulation of erythropoictin (Eprex).

Antigens to which an Immune Response should be Induced to

Exemplary antigens include cancer antigens, infectious disease antigens such antigens from hepatitis, influenza, and polio, and protozoans such as *Plasmodium* (malaria) and *Leishmania*.

Cellular antigens include tumor antigens, abnormal cellular proteins, and mammalian cellular components produced by viral, bacterial, or protozoan infected cells.

Cancer antigens include Melan-A/MART-1, Dipeptidyl peptidase IV (DPPIV), adenosine deaminase-binding protein (ADAbp), cyclophilin b, Colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGEA3, MAGE-A4, MAGE-A5, MAGE-A6, MAGE-A7, MAGE-A8, MAGE-A9, MAGE-A10, MAGE-A11, MAGEA12, MAGE-Xp2 (MAGE-B2), MAGE-Xp3 (MAGE-B3), MAGE-Xp4 (MAGE-B4), MAGE-C1, MAGE-C2, MAGEC3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100Pmel117, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, PIA, Connexin 37, Ig-idiotype, p15, gp75, GM2 and GD2 gangliosides, viral products such as human papilloma virus proteins, Smad family of tumor antigens, Imp-1, EBV-encoded nuclear antigen (EBNA)-1, or c-erhB-2.

b. Immunomodulators

Tolerance

As reported by Kishimoto and Maldonado, Front. Immunol., 20 Feb. 2018|https://doi.org/10.3389/fimmu.2018.00230 "Nanoparticles for the Induction of Antigen-Specific Immunological Tolerance", pharmacological agents targeting at least two different signaling pathways have been used to induce antigen-specific tolerance in vivo.

NF-κB Inhibitors

NF kappa B is a master regulator of a broad array of genes controlling inflammation and cell survival. Thomas and colleagues have demonstrated that co-delivery of antigen with various NF-κB inhibitors, such as curcumin, quercetin, and Bay11-07082, in liposomes suppressed inflammatory arthritis in an antigen-specific manner (Capini et al. J Immunol (2009) 182(6):3556-65. doi:10.4049/jimmunol.0802972).

mTOR Inhibitors

The mammalian target of rapamycin is a conserved serine/threonine kinase that integrates environmental signals to regulate cell metabolism and survival. Rapamycin is a natural product derived from *Streptomyces hygroscopicus*, which binds to the FK506-binding protein to form a complex that acts as an allosteric inhibitor of the mTOR complex-1 pathway. Rapamycin promotes Treg expansion and differentiation. In vitro treatment of DC induces a tolerogenic phenotype (Turnquist et al. J Immunol (2007) 178 (11):7018-31. doi:10.4049/jimmunol.178.11.7018; Fischer et al. Handb Exp Pharmacol (2009) 18:215-32. doi:10.1007/978-3-540-71029-5_10).

As reported by Kishimoto and Maldonado, Front. Immunol., 20 Feb. 2018|https://doi.org/10.3389/fimmu.2018.00230, rapamycin-loaded nanoparticles show potent tolerogenic activity in vivo. NPs containing rapamycin induced durable antigen-specific immune tolerance when coadministered with various encapsulated or free protein and peptide antigens. In addition, rapamycin-containing NPs inhibited B cell activation and differentiation into effector cells, germinal center formation and antibody production. These rapamycin-containing tNPs were effective in preventing IgE-mediated anaphylaxis in models of allergy, IgG-mediated anaphylaxis associated with repeated intravenous challenges with antigen, and the formation of anti-drug antibodies (ADAs) to a wide range of biologic drugs. Coadministration of tNPs containing rapamycin with free biologic drugs was effective in preventing ADAs against coagulation FVIII (ADVATE®) in a model of hemophilia A; human TNFα-blocking antibody adalimumab (HUMIRA®) in a model of inflammatory arthritis, acid-α-glucosidase (LUMIZYME®) in a model of Pompe disease, recombinant immunotoxin in a model of mesothelioma, adeno-associated virus gene therapy vectors and pegylated uricase (pegsiticase) in uricase-deficient mice and non-human primates. Currently the combination of tNP-rapamycin and pegsiticase (SEL-212) is in Phase 2 clinical trials (NCT02959918) in patients with symptomatic gout and hyperuricemia.

In some embodiments, the immunomodulator is TGF-β, rapamycin, or retinoic acid, and other agents that induce regulatory T cells.

Rapamycin (also known as SIROLIMUS®) has a structure according to Formula I, or a derivative prodrug or functional analog of rapamycin.

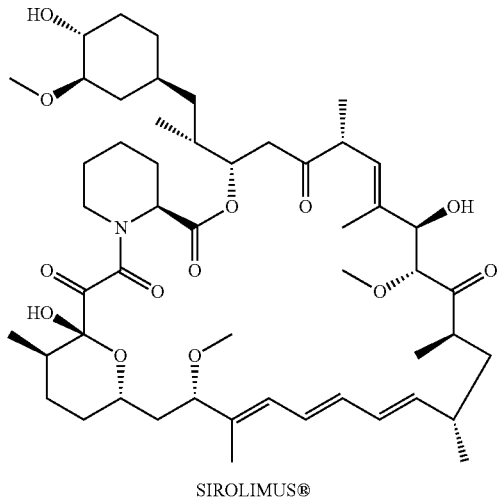

Formula I

SIROLIMUS®

SIROLIMUS® is a macrolide compound produced by the bacterium *Streptomyces hygroscopicus* and was first isolated in 1972, from samples of *Streptomyces hygroscopicus* found on Easter Island. SIROLIMUS® has Empirical Formula $C_{51}H_{79}NO_{13}$, and a molecular weight of 914.17 Da (CAS Number: 53123-88-9). It is thought SIROLIMUS® inhibits activation of T cells and B cells by reducing the production of interleukin-2 (IL-2).

SIROLIMUS® is a member of the class of compounds that inhibit the mechanistic target of rapamycin (mTOR) molecule (i.e., mTOR inhibitors). SIROLIMUS® (rapamycin) has been shown to have immunosuppressant functions through regulation of T cell activities and has been shown to be useful in preventing the rejection of organ transplants, as well as inhibiting neointimal hyperplasia in arterial and vein grafts (Suzuki, et al., *Circulation* 104, 1188-1193 (2001); Araki, et al., *Nature*, 460, 108-112 (2009)).

Variants, derivatives and functional analogues of rapamycin are known, including the structural analog everolimus (also known under the trade names ZORTRESS®, CERTICAN®, AFINITOR®, and VOTUBIA®,) temsirolimus (pro-drug analog of rapamycin, also known as CCI-779), as well as deforolimus or ridaforolimus. Rapamycin and its variants, derivatives, and functional analogues are described in WO 95122972, WO 95116691, WO 95104738, U.S. Pat. Nos. 6,015,809; 5,989,591; U.S. Pat. Nos. 5,567,709; 5,559, 112; 5,530,006; 5,484,790; 5,385,908; 5,202,332; 5,162, 333; 5,780,462; 5,120,727.

Immunostimulation

The immunomodulators include interleukins (IL-), interferons (IFN-), or cytokines, such as IFN-γ, IL-4, IL-2, IL-10, IL-17 and/or TNF-α. In some embodiments, the immunostimulatory agent is a toll-like receptor (TLR) agonist, cytokine receptor agonist, CD40 agonist, Fc receptor agonist, CpG-containing immunostimulatory nucleic acid, complement receptor agonist, or an adjuvant. In some embodiments, the TLR agonist is a TLR-1, TLR-2, TLR-3, TLR-4, TLR-5, TLR-6, TLR-7, TLR-8, TLR-9, or TLR-10 agonist. In some embodiments, the Fc receptor agonist is an Fcgamma receptor agonist. In some embodiments, the complement receptor agonist binds to CD21 or CD35.

Examples of immunological adjuvants that can be associated with the particles include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A, TLR3 ligands (e.g., polyinosinic-polycytidylic acid (poly(I:C)), TLR7 ligands (e.g., imiquimod and resiquimod), and TLR9 ligands.

c. Therapeutic Agents

Therapeutic agents include anti-infectives, general immunomodulatory agents, neuroactive agents, hormones and chemotherapeutic agents, as well as prophylactic agents.

Antimicrobial agents include agents effect in treating or alleviating the symptoms of viral, bacterial or fungal infection. These can be small molecules (2000 D, 1500 D, and 1000 D), proteins, peptides, or combinations thereof.

Representative anti-cancer agents include, but are not limited to, alkylating agents (such as cisplatin, carboplatin, oxaliplatin, mechlorethamine, cyclophosphamide, chlorambucil, dacarbazine, lomustinc, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel, epothilones A-F, and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), and combinations thereof. Other suitable anti-cancer agents include angiogenesis inhibitors including antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (NEXAVAR®), erlotinib (TARCEVA®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

Other suitable anti-neoplastic agents include cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, tamoxifen, piposulfan, altretamine, asparaginase, bleomycin, busulfan, carboplatin, carmustine, chlorambucil, cisplatin, cladribine, cyclophosphamide, cytarabine, dacarbazine, diethylstilbestrol, ethinyl estradiol, etoposide, mitomycin, mitotane, mitoxantrone, paclitaxel, pentastatin, pipobroman, plicamycin, prednisone, procarbazine, streptozocin, tamoxifen, teniposide, vinblastine, and vincristine.

Imaging Agents

The particles may also include imaging agent such as radionuclide-labeled small molecules, such as Technetium99 ($^{99m}$Tc), F-18 fluorodeoxyglucose, fluorinated compounds, such as fluorinated silicon oil, perfluorocarbon, or perfluoropolyether containing $^{19}$F, superparamagnetic iron oxide (SPIO), gadolinium, europium, diethylene triamine pentacetic acid (DTPA), 1,4,7,10-tetraazacyclododecane-1, 4,7,10-tetraacetic acid (DOTA) and their derivatives, gas, and fluorescent tracers. Suitable modalities with respective tracers are known in the art (Baum et AL., *Theranostics*, 2(5)437-447 (2012)).

Exemplary radioisotopes include, but are not limited to Molybdenum-99, Technetium-99m, Chromium-51, Cobalt-60, Copper-64, Ytterbium-169, Iodine-131, Iridium-192, Iron-59, Xenon-133, Xenon-127, Phosphorus-32, Potassium-42, Samarium-153 (and Strontium-89, Selenium-75, Sodium-24, Yttrium-90, Gallium-67, Fluorodeoxyglucose-18, and combinations thereof.

6. Targeting Moiety

The particles may include a targeting moiety. The targeting moiety may be present on the core particle, on the tethered particle, or both on the core particle and on the tethered particle.

The particles can be targeted to a specific tissue or organ in vivo with a surface ligand or moiety. The targeting moiety can be covalently or non-covalently associated with the particles. The targeting moiety may be an antibody or antigen-binding fragment thereof. The targeting moiety can be an RNA or protein shaped to specifically interact with the target (e.g., an RNA- or peptide-aptamer). The targeting moiety can be a small molecule or element with specific binding affinity (e.g., biotin which binds streptavidin, or iron which is bound by the transferrin receptor). The targeting moieties should have an affinity for a cell-surface receptor, cell-surface antigen, or other ligand that is specific to the target tissue.

The targeting moiety can specifically recognize and bind to a target molecule specific for a cell type, a tissue type, or an organ. The target molecule can be a cell surface polypeptide, lipid, or glycolipid. The target molecule can be a receptor that is selectively expressed on a specific cell surface, a tissue or an organ. Cell specific markers can be for specific types of cells including, but not limited to stem cells, skin cells, blood cells, immune cells, muscle cells, nerve cells, cancer cells, virally infected cells, and organ specific cells. The cell markers can be specific for endothelial, ectodermal, or mesenchymal cells. Representative cell specific markers include, but are not limited to cancer specific markers, immune-cell specific markers, and skin-cell specific markers. The STPs with the targeting moieties may be delivered to specific tissues, such as liver tissue, pancreatic tissue, heart tissue, lung tissue, intestinal tissue, spleen tissue, kidney tissue, bladder tissue, muscle tissue, bone tissue, cartilage, neural tissue, the blood, lymphatic tissues, or sensory tissues, such as skin, eye, ear and nasal passages.

The targeting moiety can be covalently associated with the STP, and the covalent association can be mediated by a linker.

In some aspects, the targeting moiety is a peptide. Specifically, the peptide can be, but is not limited to, one or more of the following: Epidermal growth factor (EGF), hepatocyte growth factor, and 0.4 integrin (which is bound by vascular cell adhesion molecule-1), or the targets of various integrins (e.g. integrin ligands, matrikines and matricryptins).

The targeting moiety can be an antibody or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. The antigen binding portion of the antibody can be any portion that has at least one antigen binding site, such as Fab, F(ab')2, dsFv, sFv, diabodies, and triabodies. In certain embodiments, the antibody is a single chain antibody.

Aptamers are oligonucleotide or peptide sequences with the capacity to recognize virtually any class of target molecules with high affinity and specificity. Aptamers bind to targets such as small organics, peptides, proteins, cells, and tissues. Unlike antibodies, some aptamers exhibit stereoselectivity. The aptamers can be designed to bind to specific targets expressed on cells, tissues or organs.

B. Spatiotemporal Agent Release

The STP are designed so that they release agents within the same cells, but not at the same time, with the tethered agents being released first, then the core agents, to achieve the required spatial and temporal requirements for efficacy. The linker or tether as well as particle composition can be used to determine when the agent is released relative to release of agent from the core.

1. Spatial Aspect of Release

The spatial aspect of release refers to spatially separated release of one, two, or more agents from the same particle within the same targeted cells. Spatially separated release of agents may be a release from two or more separate regions of the same particle. Spatially separated release of agents may be a release at two or more anatomical regions in a subject from the same particle. Spatially separated release of agents may be a release from two or more separate regions of a particle and a release at two or more anatomical regions in a subject from the same particle. For example, the particle may be injected subcutaneously and engulfed by Langerhans cell, delivered to a local lymph node by the same Langerhans cell, wherein the particle releases the first agent from one part of the particle in Langerhans cell positioned subcutaneously, and releases the second agent from another part of the particle in the same Langerhans cell now positioned in the lymph node.

2. Temporal Aspect of Release

The temporal aspect of release refers to timing of release of one, two, or more agents from the same particle. Timing of release of an agent may be a first release and a second release of the agent separated in time. The first release of the agent may or may not overlap in time with the second release. For example, the first release of the agent may overlap with the second release such that the first release may be at about 50%, at about 60%, at about 70%, at about 80%, at about 90%, or at about 100% of the total release of the agent, before the second release is at about 10%, at about 20%, or at about 30% of the total release of the agent. The first release of the agent and the second release of the agent may not overlap, such that the first release may be at about 100% of the total release of the agent, before the second release is at about 1% or at about 10% of the total release of the agent. There may be a time delay between the first release, for example, after about 100% of the total release of the agent, before the second release is initiated. The time delay may be in minutes, hours, or days. The time delay may be between 1 minute and 60 minutes, between 1 hour and 24 hours, or between 24 hours and 168 hours. The first release may be a release of a first agent and the second release may be a release of the second agent, where the first agent and the second agent are the same agent or are different agents.

The release of the first agent and the release of the second agent may occur within a time period between minutes and hours, a day, two days, three days, a week, two weeks, three weeks, a month or more.

C. Compositions

The particles may be formulated into pharmaceutical compositions with suitable excipients, in suitable dosage forms, to provide effective amounts of the one or more agents in the compositions. Typically the particles will be administered by injection, intravenously, subcutaneously, intramuscularly, although there may be embodiments where they are administered topically to tissue or mucosal surface (nasal, vaginal, buccal, rectal, pulmonary, oral).

Excipients may include suspending agents such as sterile water, phosphate buffered saline, saline, or a non-aqueous solution such as glycerol.

The STPs may be stored in any suitable storage medium. The storage can be at temperatures at or below 0° C. (e.g., −20° C., −80° C., or −165° C.), at or above 0° C., such as at refrigeration temperature (about 4° C.), at about 10° C., at room temperature and standard pressure (about 20° C., 1 atm), or at physiological temperature (about 37° C.). Storage may be in any suitable vessel for ease of utilizing the STPs in future applications. Suitable storage vessels include, but are not limited to, capsules, vials, packets, pouches, syringes, tubes, tubs, cans, and lyophilized containers.

III. Methods of Making the Particles and Compositions

A. Methods of Making the Core Particles

The core particles described herein can be prepared by a variety of methods. The preferred method is an emulsion method as described in the examples.

1. Solvent Evaporation

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. The nanoparticles with different sizes and morphologies can be obtained by this method. This method is useful for relatively stable polymers like PBA, polyesters and polystyrene.

2. Interfacial Polycondensation

Interfacial polycondensation is used to encapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

3. Solvent Evaporation Microencapsulation

In solvent evaporation microencapsulation, the polymer is typically dissolved in a water immiscible organic solvent and the material to be encapsulated is added to the polymer solution as a suspension or solution in an organic solvent. An emulsion is formed by adding this suspension or solution to a beaker of vigorously stirring water (often containing a surface active agent, for example, polyethylene glycol or polyvinyl alcohol, to stabilize the emulsion). The organic solvent is evaporated while continuing to stir. Evaporation results in precipitation of the polymer, forming solid nanoparticles containing core material.

The solvent evaporation process can be used to entrap a liquid core material in a polymer such as PBA, PLA, PLA/PGA copolymer, or PLA/PCL copolymer microcapsules. The polymer or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the polymer or copolymer to phase separate and migrate towards the surface of the core material droplets. This phase-separated solution is then transferred into an agitated volume of nonsolvent, causing any remaining dissolved polymer or copolymer to precipitate and extracting any residual solvent from the formed membrane. The result is a nanoparticle composed of polymer or copolymer shell with a core of liquid material.

Solvent evaporation microencapsulation can result in the stabilization of insoluble active agent particles in a polymeric solution for a period of time ranging from 0.5 hours to several months. Stabilizing an insoluble pigment and polymer within the dispersed phase (typically a volatile organic solvent) can be useful for most methods of microencapsulation that are dependent on a dispersed phase, including film casting, solvent evaporation, solvent removal, spray drying, phase inversion, and many others.

The stabilization of insoluble active agent particles within the polymeric solution could be critical during scale-up. By stabilizing suspended active agent particles within the dispersed phase, the particles can remain homogeneously dispersed throughout the polymeric solution as well as the resulting polymer matrix that forms during the process of microencapsulation.

Solvent evaporation microencapsulation (SEM) have several advantages. SEM allows for the determination of the best polymer-solvent-insoluble particle mixture that will aid in the formation of a homogeneous suspension that can be used to encapsulate the particles. SEM stabilizes the insoluble particles or pigments within the polymeric solution, which will help during scale-up because one will be able to let suspensions of insoluble particles or pigments sit for long periods of time, making the process less time-dependent and less labor intensive. SEM allows for the creation of microparticles or nanoparticles that have a more programmable release of the encapsulated material.

4. Solvent Removal Microencapsulation

In solvent removal microencapsulation, the polymer is typically dissolved in an oil miscible organic solvent and the material to be encapsulated is added to the polymer solution as a suspension or solution in organic solvent. The agents can be added to improve the dispersion of the material to be encapsulated. An emulsion is formed by adding this suspension or solution to vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid particles containing core material.

5. Phase Separation Microencapsulation

In phase separation microencapsulation, the material to be encapsulated is dispersed in a polymer solution with stirring. While continually stirring to uniformly suspend the material, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the core material in a droplet with an outer polymer shell.

6. Spontaneous Emulsification

Spontaneous emulsification involves solidifying emulsified liquid polymer droplets by changing temperature, evaporating solvent, or adding chemical cross-linking agents. The physical and chemical properties of the encapsulant, and the material to be encapsulated, dictates the suitable methods of encapsulation. Factors such as hydrophobicity, molecular weight, chemical stability, and thermal stability affect encapsulation.

7. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=−24° C., outlet temperature=13-15° C., aspirator setting=15, pump setting=10 mL/minute, spray flow=600 Nl/hr, and nozzle diameter=0.5 mm. Microparticles ranging between 1-10 microns are obtained with a morphology which depends on the type of polymer used.

B. Methods of Making the Tethered Particle

Techniques and reagents are commercially available for coupling avidin-biotin or by using Click Chemistry. The tethered particles are formed as described above.

IV. Methods of Using the Particles and Compositions

Spatiotemporally tuned particles (STP) provide for the delivery of agents to the same cells in a preferred order. The release kinetics of STP have been validated, and STP has shown enhanced tolerogenic effects both in vitro and in vivo (see Examples). STP can be used to deliver any combination of agents, in a desired temporal release profile, to be applied for treatment of cancer, autoimmune diseases, allergies, epigenetic manipulations, or other diseases that require spatiotemporal considerations for treatment.

In current formulations involving administration of multiple agents, it is assumed that the activity kinetics of the multiple agents are the same. In the case of co-delivery of antigens and immunomodulators, the antigen will display on an APC at the same time as the cell itself is being reprogrammed to become tolerogenic. By administering such agents at the same time either subcutaneously, intradermal or intravenously, it is assumed that the combination of factors will localize to the same affected or diseased region.

However, these therapies have a limited efficacy. With standard formulations, the efficacy is only a fraction of what it can be if the spatial and temporal aspects of administration are properly determined during administration of the drug combinations.

As such, many diseases can be treated with greater efficacy if drugs or immunological agents can be locally delivered in the preferred sequence. For example, combinatorial delivery of drugs (such as checkpoint inhibitors) and cytokine (such as IL-2) in cancer immunotherapy can be staggered such that checkpoint inhibitors and IL-2 are delivered to the same spatial location, the earlier release of checkpoint blockade inhibiting suppressive Tregs in the tumor microenvironment and therefore increasing IL-2 availability specifically to TILs. Unfortunately, to date, there is no single technology that can achieve this "Spatiotemporal" aspect in any therapy. To overcome the issue, several regimens require unlocalized injections at different time points, or different frequencies. The expected effects are the usual toxicity, limited efficacy, and adverse short and long-term side effects.

The Examples below demonstrate that by employing temporal staggering of agent release and spatial localization, antigen-specific tolerance induction can be achieved. The particles may be used to form programmable formulations that facilitate localization and required temporal release of agents for improving treatment outcomes in diverse diseases requiring combined therapies.

Because STP is a single platform that delivers multiple agents with the desired kinetics, treatment regimens are better fine-tuned with greater efficacy. Efficacy is enhanced with logarithmically lower drug concentrations. This in turn reduces adverse side-effects, and the prolonged hospitalization of patients and expense of monitoring and treatment is significantly lowered. The STP may be better vaccine platforms as they may accommodate both adjuvant and antigen in a single vehicle with proper release features making them more efficacious.

1. Inhibition of Epitope Spreading and Induction of Tolerance

Many DCs are present in the periphery, where they constantly sense the environment by endocytosis. Once activated by pathogen-associated molecular pattern molecules (PAMPs) or damage-associated molecular pattern molecules (DAMPs), they rapidly produce early proinflammatory signals such as NO, TNF-α, or type I interferons (IFNs) to combat the infection or tissue danger. Mammalian target of rapamycin complex 1 (mTORC1) and mTORC2 are activated by TLR ligands and usually support these responses. Therefore, inhibition of mTOR at this time point is considered anti-inflammatory. Later, these DCs upregulate CCR7 and migrate to lymph nodes to activate T cells. They shut down antigen uptake, optimize antigen presentation, and increase the expression of the costimulatory molecule CD86, while inhibitory PD-L1 is also induced to prevent excessive T cell activation. Moreover, immunomodulatory cytokines such as IL-12 and IL-10 are maximally expressed at these late time points to guide T helper cell activation and differentiation. Inhibition of mTOR at this time point usually enhances antigen presentation and CCR7, CD86, and IL-12 production and blocks PD-L1 and IL-10 expression, which in total promotes T cell activation. See FIGS. 6A-6C.

In the lymph node, limiting the amount of nutrients downregulates mTOR in DCs, which may act as an intrinsic signal to support their T cell-stimulatory capacities. Pharmacological inhibition of mTOR thus exacerbates a response that is physiologically occurring in lymph nodes to support T cell activation.

Epitope spreading refers to the ability of B and T cell immune response to diversify both at the level of specificity, from a single determinant to many sites on an auto antigen, and at the level of V gene usage (Monneaux, F. et al., *Arthritis & Rheumatism,* 46(6): 1430-1438 (2002). Epitope spreading is not restricted to systemic autoimmune disease. It has been described in T cell dependent organ specific diseases such as insulin dependent diabetes mellitus (IDDM) and multiple sclerosis in humans and EAE induced experimental animals with a variety of myelin proteins.

Epitope spreading involves the acquired recognition of new epitopes in the same self molecule as well as epitopes residing in proteins that are associated in the same macromolecular complex. Epitope spreading can be assessed by measuring delayed-type hypersensitivity (DTH) responses, methods of which are known in the art.

Therefore, in some embodiments, a method for inhibiting or reducing epitope spreading in a subject includes administering to the subject an effective amount of particles. In a preferred embodiment the particle formulation inhibits epitope spreading in the subject.

a. Antigen-Specific Tolerance

Co-administration of antigen with immunosuppressive agents such as Rapamycin is a promising approach for induction of antigen-specific tolerance. The direct priming of antigen presenting cells, such as Dendritic Cells (DCs), with antigen and immunosuppressives or tolerogenic agents is understood as a potentially powerful new "anti-vaccination" approach that induces a tolerant immunity against the antigen of choice as opposed to priming an immune response against an antigen. The therapeutic applications range from autoimmune disease states to transplantation, allergy and asthma. This strategy, termed "antigen-specific tolerance" is of significant interest and seeks methods to tune immunity against specific antigens such pancreatic B cell antigens for diabetes, nuclear antigens for lupus, new antigenic sequences and epitopes for inflammatory bowel disease, Crohn's disease, collagen-based antigens for rheumatoid arthritis, white matter and dark matter antigens for multiple sclerosis, donor antigenic sequences in transplants, food allergens and other diseases.

Currently, all strategies focus on administering the antigen together with the tolerance adjuvant at the same time as a bolus or injectable. The platform in nanoparticle design and production exploits the understandings in disease pathogenesis and molecular interactions within and between cells to create a powerful new methodology that addresses antigen-specific tolerance.

The particles are formed to modulate antigen-specific tolerance, which can be significantly enhanced or reduced through sequential timing of delivery of an antigen and a tolerogenic agent (such as an immunomodulator, or an immunosuppressive agent). The particles simultaneously enable the control of the localization of agent release and the timing of the agent release by staggering release of the antigen and the tolerogenic agent.

By temporally staggering the delivery of the antigen and the immunomodulatory agent, one can significantly enhance or reduce the quality and magnitude of antigen-specific tolerance. That is, the sequence of delivery of antigen and the immunomodulatory agent matters for tuning and enhancing antigen-specific induction and maintenance of tolerance. Temporal staggering of the agents is described as a "tuning knob" for controlling the levels of immunological tolerance.

The spatial localization of the immunomodulator and antigen is important for antigen-specific tolerance induction. The requirement for co-encapsulation of both agents in one particle supports the use of the particles to deliver the immunomodulator and antigen to the same antigen-presenting cell (APC), as the same APC needs to be primed to display antigen and be phenotypically tolerant. In other words, a subset of cells displaying antigen and another subset exhibiting tolerogenic behavior is not sufficient nor efficient for inducting maintenance of tolerance to the antigen in a safe manner. Tolerant cells alone may display other antigens (promoting long-term adverse/safety issues) and cells displaying antigen without being phenotypically tolerogenic may induce a pro-inflammatory response against the displayed antigen (worsening the disease) or ineffectual. Thus, spatial localization of both agents to the same APC is needed for the effective tolerance induction and prevention of adverse effects due to immunization.

i. Allergies

A similar methodology can be used to treat allergies, substituting the allergen of interest for the autoimmune stimulus. Typically, particles are administered to a subject in an effective amount to reduce or inhibit an allergy or allergic reaction.

Allergies are abnormal reactions of the immune system that occur in response to otherwise harmless substances. Allergies are among the most common of medical disorders. It is estimated that 60 million Americans, or more than one in every five people, suffer from some form of allergy, with similar proportions throughout much of the rest of the world. Allergy is the single largest reason for school absence and is a major source of lost productivity in the workplace.

An allergy is a type of immune reaction. Normally, the immune system responds to foreign microorganisms or particles by producing specific proteins called antibodies. These antibodies are capable of binding to identifying molecules, or antigens, on the foreign particle. This reaction between antibody and antigen sets off a series of chemical reactions designed to protect the body from infection. Sometimes, this same series of reactions is triggered by harmless, everyday substances such as pollen, dust, and animal dander. When this occurs, an allergy develops against the offending substance (an allergen.)

Mast cells, one of the major players in allergic reactions, capture and display a particular type of antibody, called immunoglobulin type E (IgE) that binds to allergens. Inside mast cells are small chemical-filled packets called granules. Granules contain a variety of potent chemicals, including histamine.

Immunologists separate allergic reactions into two main types: immediate hypersensitivity reactions, which are predominantly mast cell-mediated and occur within minutes of contact with allergen; and delayed hypersensitivity reactions, mediated by T cells (a type of white blood cells) and occurring hours to days after exposure.

Inhaled or ingested allergens usually cause immediate hypersensitivity reactions. Allergens bind to IgE antibodies on the surface of mast cells, which spill the contents of their granules out onto neighboring cells, including blood vessels and nerve cells. Histamine binds to the surfaces of these other cells through special proteins called histamine receptors. Interaction of histamine with receptors on blood vessels causes increased leakiness, leading to the fluid collection, swelling and increased redness. Histamine also stimulates pain receptors, making tissue more sensitive and irritable. Symptoms last from one to several hours following contact. In the upper airways and eyes, immediate hyper-sensitivity reactions cause the runny nose and itchy, bloodshot eyes typical of allergic rhinitis. In the gastrointestinal tract, these reactions lead to swelling and irritation of the intestinal lining, which causes the cramping and diarrhea typical of food allergy. Allergens that enter the circulation may cause hives, angioedema, anaphylaxis, or atopic dermatitis.

Allergens on the skin usually cause delayed hypersensitivity reaction. Roving T cells contact the allergen, setting in motion a more prolonged immune response. This type of allergic response may develop over several days following contact with the allergen, and symptoms may persist for a week or more.

Allergens enter the body through four main routes: the airways, the skin, the gastrointestinal tract, and the circulatory system. Airborne allergens cause the sneezing, runny nose, and itchy, bloodshot eyes of hay fever (allergic rhinitis). Airborne allergens can also affect the lining of the lungs, causing asthma, or conjunctivitis (pink eye). Exposure to cockroach allergens has been associated with the development of asthma. Airborne allergens from household pets are another common source of environmental exposure. Allergens in food can cause itching and swelling of the lips and throat, cramps, and diarrhea. When absorbed into the bloodstream, they may cause hives (urticaria) or more severe reactions involving recurrent, non-inflammatory swelling of the skin, mucous membranes, organs, and brain (angioedema). Some food allergens may cause anaphylaxis, a potentially life-threatening condition marked by tissue swelling, airway constriction, and drop in blood pressure. Allergies to foods such as cow's milk, eggs, nuts, fish, and legumes (peanuts and soybeans) are common. Allergies to fruits and vegetables may also occur. In contact with the skin, allergens can cause reddening, itching, and blistering, called contact dermatitis. Skin reactions can also occur from allergens introduced through the airways or gastrointestinal tract. This type of reaction is known as atopic dermatitis. Dermatitis may arise from an allergic Dermatitis may arise from an allergic response (such as from poison ivy), or exposure to an irritant causing nonimmune damage to skin cells (such as soap, cold, and chemical agents). Injection of allergens, from insect bites and stings or drug administration, can introduce allergens directly into the circulation, where they may cause system-wide responses (including anaphylaxis), as well as the local ones of swelling and irritation at the injection site.

These can be treated by administration of anti-inflammatories, or by inducing tolerance to the antigen.

ii. Inflammatory Bowel Disease

Inflammatory bowel disease (IBD) is a broad term that describes conditions with chronic or recurring immune response and inflammation of the gastrointestinal tract. The two most common inflammatory bowel diseases are ulcerative colitis and Crohn's disease. Inflammation affects the entire digestive tract in Crohn's disease and only the large intestine in ulcerative colitis. Both illnesses are characterized by an abnormal response to the body's immune system.

Crohn's disease is treated with medications designed to suppress the immune system's abnormal inflammatory response that causes the symptoms. Suppressing inflammation offers relief from common symptoms like fever, diarrhea, and pain, and healing of the intestinal tissues. Combination therapy could include the addition of a biologic to an immunomodulator. As with all therapies, there are risks and benefits of combination therapies. Combining medications with immunomodulatory therapies can increase the effectiveness of IBD treatment.

Examples of agents used to treat IBD symptoms include, but are not limited to, sulfasalazine, mesalamine, olsalazine, and balsalazide that contain 5-aminosalicylate acid (5-ASA), corticosteroids, immunomodulators, antibiotics, and biologic therapies. Examples of disease specific antigens include bacterial flagellin, and other components of gut bacteria, including commensal bacteria.

iii. Multiple Sclerosis

Multiple sclerosis is an unpredictable disease of the central nervous system. Multiple sclerosis (MS) can range from relatively benign to somewhat disabling to devastating, as communication between the brain and other parts of the body is disrupted. MS may be an autoimmune disease.

Most people experience their first symptoms of MS between the ages of 20 and 40; the initial symptom of MS is often blurred or double vision, red-green color distortion, or even blindness in one eye. Most MS patients experience muscle weakness in their extremities and difficulty with coordination and balance. These symptoms may be severe enough to impair walking or even standing. In the worst cases, MS can produce partial or complete paralysis. Most people with MS also exhibit paresthesias, transitory abnormal sensory feelings such as numbness, prickling, or "pins and needles" sensations. Some may also experience pain. Speech impediments, tremors, and dizziness are other frequent complaints. Approximately half of all people with MS experience cognitive impairments such as difficulties with concentration, attention, memory, and poor judgment, but such symptoms are usually mild and are frequently overlooked. Depression is another common feature of MS.

Currently there is no cure for MS. Three forms of beta interferon (AVONEX®, Biogen, Inc., Cambridge, Mass.; BETASERON®, Bayer Intellectual Property GMBH, Monheim Am Rhein, Germany; and REBIF®, Ares Trading S.A., Aubonne, Switzerland) have been approved by the Food and Drug Administration for treatment of relapsing-remitting MS. The FDA has also approved ocrelizumab (OCREVUS®, Genentech, Inc., San Francisco, Calif.) to treat adults with relapsing forms of MS and primary progressive MS. Beta interferon has been shown to reduce the number of exacerbations and may slow the progression of physical disability. When attacks do occur, they tend to be shorter and less severe. The FDA also has approved a synthetic form of myelin basic protein, called copolymer I (COPAXONE®, Teva Pharmaceutical Industries LTD., Jerusalem, Israel), for the treatment of relapsing-remitting MS. Copolymer I has few side effects, and studies indicate that the agent can reduce the relapse rate by almost one third. Other FDA approved drugs to treat relapsing forms of MS in adults include teriflunomide and dimethyl fumarate. An immunosuppressant treatment, Novantrone (mitoxantrone), is approved by the FDA for the treatment of advanced or chronic MS. The FDA has also approved dalfampridine (AMPYRA®, Acorda Therapeutics, Inc., Ardsley, N.Y.) to improve walking in individuals with MS.

One monoclonal antibody, natalizumab (TYSABRI®, Elan Pharma International Limited, Shannon, Ireland), was shown in clinical trials to significantly reduce the frequency of attacks in people with relapsing forms of MS and was approved for marketing by the U.S. Food and Drug Administration (FDA) in 2004. However, in 2005 the drug's manufacturer voluntarily suspended marketing of the drug after several reports of significant adverse events. In 2006, the FDA again approved sale of the drug for MS but under strict treatment guidelines involving infusion centers where patients can be monitored by specially trained physicians.

STP containing myelin basic protein (MBP), myelin oligodendrocyte glycoprotein (MOG), truncated MBP, truncated MOG, analogues of MBP or its truncated peptides, analogues of MOG or its truncated peptides, or any combination thereof, may be used to induce tolerance in a subject against these antigens. The STPs may include one or more of these antigens in the core particle, and an immunomodulator in the tethered particle, to induce antigen-specific tolerance in the subject. In some aspects, these STPs may also include additional pharmaceutical agents in the core particle or the tethered particle. Additional pharmaceutical agents include beta interferon, ocrelizumab, copolymer I, dalfampridine, natalizumab, steroids, non-steroidal anti-inflammatory agents, and any combinations thereof.

The STPs may be used in compositions to provide the immunomodulator and the antigen at an effective amount and at an effective time to induce antigen-specific tolerance in the subject.

2. Cancer

An STP for reducing one or more symptoms of a disease, such as cancer, may include a particle with the core particle containing a cytokine for stimulating an immune response, and the tethered particle containing an inhibitor, such as a checkpoint inhibitor, an anti-proliferative cancer therapeutic, and/or a cancer antigen. Exemplary cancer antigens are listed above.

3. Diabetes

Diabetes, or diabetes mellitus, is due to either the pancreas not producing enough insulin or the cells of the body not responding properly to the insulin produced. There are three main types of diabetes mellitus:

Type 1 Diabetes results from the pancreas' failure to produce enough insulin or active insulin; this form was previously referred to as "insulin-dependent diabetes mellitus" (IDDM) or "juvenile diabetes", Type 2 Diabetes begins with insulin resistance, a condition in which cells fail to respond to insulin properly. As the disease progresses a lack of insulin may also develop; this form was previously referred to as "non insulin-dependent diabetes mellitus" (NIDDM) or "adult-onset diabetes"; and Gestational diabetes, the third main form, occurs when pregnant women, without a previous history of diabetes, develop a high blood sugar level.

Type 1 diabetes must be managed with insulin injections. Type 2 diabetes may be treated with medications with or without insulin. Gestational diabetes usually resolves after the birth of the baby.

People with type 1 diabetes need insulin therapy to survive. Many people with type 2 diabetes or gestational diabetes also need insulin therapy. Medications used for treating T2D include over 20 types of injectable insulin, and orally administered drugs such as meglitinides, sulfonylureas, metformin, canagliflozin, dapagliflozin, thiazolidinediones, pioglitazone, rosiglitazone, acarbose, pramlintide, exenatide, liraglutide, long-acting exenatide, albiglutide, dulaglutide, and dipeptidyl peptidase-4 (DPP-IV) inhibitors (sitagliptin, saxagliptin, linagliptin). These agents are collectively referred to as "anti-diabetics".

STPs containing anti-diabetics and/or insulin may be used to better manage diabetes. The STPs may be used to provide timed and sequential release of these therapeutics following single administration, may be used to better manage diabetes.

In other embodiments, the methods of using the STP compositions may include methods of non-invasively imaging the target organ as a whole, or distinct microenvironments within the target organ, such as pockets of inflammation, leaky vasculature, or neoplasms. In these embodiments, the methods include administering to a subject in need thereof a dosage unit of the STP composition containing an effective amount of an imaging agent, optionally with a therapeutic or prophylactic agent; delivering the effective amount of the imaging agent to target tissue, such as skin, breast, brain, bone, heat, lung, kidney, spleen, pancreas, liver, stomach, or colon; optionally, releasing the effective amount of the imaging agent from the nanoparticles at the target tissues; which results in enhanced detection of target tissue, or a distinct microenvironment within the target tissue, via non-invasive imaging.

Imaging modalities suitable for detecting the STPs, and/or the agents released from the STPs, include positron-emission tomography (PET), computed tomography (CT), magnetic resonance imaging (MRI), ultrasound imaging (US), and optical imaging. Suitable imaging agents (tracers) include radionuclide-labeled small molecules, such as F-18 fluorodeoxyglucose, superparamagnetic iron oxide (SPIO), gadolinium, europium, diethylene triamine pentacetic acid (DTPA), 1,4,7,10-tetraazacyclododecane-1,4,7,10-tetraacetic acid (DOTA) and their derivatives, gas, and fluorescent tracers. Such suitable modalities with respective tracers are known in the art (Baum et al., *Theranostics*, 2(5)437-447 (2012)).

The present invention will be further understood by reference to the following non-limiting examples.

EXAMPLES

Dendritic cells exposed to different sequences of the model antigen, OVA, and the mTOR inhibitor, rapamycin, loaded separately in nanoparticles, exhibit different potencies in tolerance induction. DCs exposed first to RAPA, then to antigen, expressed lower levels of positive co-stimulatory markers, higher levels of negative co-stimulatory markers, produced more anti-inflammatory cytokines, and induced a more potent tolerogenic response overall compared to other sequences of administration. DCs exposed to antigen prior to RAPA, or exposed to both agents simultaneously were less tolerogenic. The results showed that, for effective vaccine design, the temporal sequence of administration of antigen and tolerogenic adjuvant plays a critical role in efficacy. The data show efficacy of the particles for effective tolerogenic immunization or immunostimulatory immunization.

Of the main professional antigen-presenting cells (APCs), the dendritic cell (DC) is the most potent and is pivotal in initiating antigen-specific immune responses. Through interactions with T lymphocytes, DCs bridge innate and adaptive immunity and are key players in the development of immunogenicity against pathogens and the maintenance of tolerance towards self-antigen. The priming conditions under which DCs encounter antigen greatly influences the elicited response. Effective immunogenic vaccines rely on the inclusion of stimulatory adjuvant to serve as an activation signal and initiate the process of DC maturation. This promotes migration to the draining lymph nodes, facilitation of antigen presentation, upregulation of costimulatory markers, and changes in cytokine expression that are all critical to inducing a potent T cell response and enhancing vaccine efficacy. Changes to any of these parameters alter the environment in which antigen presentation occurs, influencing both the quality and magnitude of the elicited T cell response. The choice of adjuvant can play a vital role in shaping this environment by skewing the immature DC towards a stimulatory or tolerogenic phenotype.

Examples show that co-delivery in a preferred sequence by nanocarriers enhanced the magnitude and quality of the tolerogenic response. Biotin-attached RAPA-cyclodextrin complexes (RAPA-CD) were synthesized to decorate the surface of avidin-coated PLGA nanoparticles, as the looser association of RAPA with cyclodextrin resulted in earlier release compared to the antigen inside the core of the nanoparticles. The physical characteristics of the resultant, STP, was similar to that of the other conventional nanoparticles. Both in vitro and in vivo use showed that STP induced tolerance through expansion of Tregs to the greatest extent. nTregs or pre-existing Tregs in particular were selectively expanded, rather than induction of iTregs de novo. Evaluation of STP in murine autoimmune disease models revealed that STP was able to both prevent and reverse the disease. Single-cell RNAseq suggested that APCs, particularly M2 macrophages, were most widely affected and presented antigen in the early stages of STP injection. Depletion of macrophages and PD-L1 completely reversed the expansion of Tregs and tolerance, emphasizing the importance of macrophages and overall selective targeting of APCs by STP as a mechanism of action. Described is a unique platform that provides a path forward for multivariable drug delivery applications that are effective due to their spatiotemporal configuration.

Example 1. Spatial and Temporal Considerations in Inducing Antigen-Specific Tolerance Dendritic cells (DCs) are professional antigen presenting cells that are essential in developing an immune response to pathogens and tolerance to self-antigens (Merad et al., *Annual review of immunology*, 31:563-604 (2013)). In the immune system, DCs are key players that bridge innate to adaptive immunity through their interactions with T lymphocytes (Maldonado and von Andrian. *Advances in immunology*, 108:111-65 (2010)). For a robust immune response, T cells require three signals from DCs for activation and prolonged survival: (1) Interaction of the T cell receptor (TCR) with processed antigen presented on the major histocompatibility complex (MHC) I or II; (2) Activation of a co-stimulatory marker on T cells, such as CD28; and (3) Secretion of cytokines that can program T cells to be developed into a certain subset, such as $T_H1$, $T_H2$, $T_H17$, or Tregs (Sallusto and Lanzavecchia. *Arthritis Research & Therapy*, 4:S127-S132 (2002); Kapsenber. *Nature Reviews Immunology*, 3:984 (2003)). DC's multifaceted ability to provide all required signals for T cell function has attracted the use of DC vaccination for cancer immunotherapy and induction of tolerance (Gross and Wiendl, *Current opinion in rheumatology*, 25:268-74 (2013); Palucka and Banchereau. *Nature Reviews Cancer*, 12:265 (2012)).

Immature DCs that have not been activated through phagocytosis of an antigen express low levels of co-stimulatory markers, such as CD80 or CD86 (Merad et al. *Annual review of immunology*, 31:563-604 (2013); Dudek et al., *Frontiers in Immunology*, 4:438 (2013)). Some studies have shown that tolerogenic DCs, despite having a similar surface marker profile to immature DCs, are a distinct subset through production of anti-inflammatory cytokines, such as IL-10, retinoic acid, and TGF-β. Several methods of generating tolerogenic DCs have been proposed, such as treatment of DCs with aryl hydrocarbon receptor ligand (Harden et al., *Immunological investigations* 41, 738-764 (2012); Quintana et al., *Proceedings of the National Academy of Sciences*, 107:20768-20773 (2010)), IL-10, or rapamycin (Maldonado and von Andrian. *Advances in immunology*, 108:111-65 (2010); Bonifaz et al., J Exp Med, 196:1627-38 (2002); Raker et al., *Frontiers in Immunology*, 6:569 (2015)).

Tolerogenic DCs are potent generators of $CD4^+$ $CD25^+$ $Foxp3^+$ Tregs (Maldonado and von Andrian. *Advances in immunology*, 108:111-65 (2010)), which suppress inflammation and establish self-tolerance (Josefowicz et al., *Annual review of immunology*, 30:531-564 (2012)). Tregs suppress inflammatory T cells in a cell-cell contact-dependent context (Sojka et al., *Immunology*, 124:13-22 (2008), and cytokines TGF-β and IL-2 are required for their maintenance. Adoptive transfers of Foxp3+ Tregs have been efficacious in treatment of autoimmune diseases, such as type-1 diabetes, multiple sclerosis, and inflammatory bowel disease (Roncarolo et al., *Nature Reviews Immunology*, 7:585 (2007)). Induction and expansion of Tregs have been the overlapping goal for almost all immunotherapy for autoimmune diseases.

Combinatory delivery of immunomodulatory agents and antigen, such as RAPA and antigen, to the same DCs is now a well-established mode of developing a tolerogenic response (Look et al., *The Journal of clinical investigation*, 123, 1741-9 (2013)). Since biodegradable nanoparticles can encapsulate the immunosuppressive agent and the antigen together, nanoparticles have been considered as promising vehicles for treatment of cancer (Gregory et al., *Frontiers in cellular and infection microbiology*, 3:13 (2013)), and autoimmune diseases (Maldonado et al., *Proceedings of the National Academy of Sciences*, 112:E156-E165 (2015)).

Therefore, direct delivery of antigen and tolerogenic agent to antigen presenting cells is a promising modality for induction of antigen-specific tolerance needed for the treatment of autoimmune disease. In this modality, antigen presentation by dendritic cells (DCs) is required for robust stimulation and skewing of the antigen-specific T cell response. A central question with this combinatorial approach is the timing and the location of antigen delivery.

Materials and Methods

Nanoparticle Synthesis

Either OVA or RAPA was encapsulated in poly-lactic-co-glycolic acid nanoparticles (50:50 monomer ratio) using water/oil/water double emulsion method described by Fahmy et al. *Biomaterials*, 26:5727-5736 (2005). For RAPA encapsulation, 10% of the total PLGA polymer mass (8 mg of RAPA per 80 mg of PLGA) was added directly to the polymer dissolved in chloroform. For OVA encapsulation, 1.5 mg of OVA dissolved in 200 μL of water was added drop-by-drop while PLGA in chloroform was being vortexed. The primary emulsion containing dissolved RAPA or OVA was sonicated, which was added drop-by-drop to 3 ml of water containing 5% poly-vinyl-alcohol (Sigma-Aldrich). The resulting double-emulsion was sonicated to yield nano-sized droplets with encapsulated RAPA or OVA. Solvent was removed by stirring at room temperature for 4 hours. Nanoparticles were then washed three times in MilliQ water and lyophilized for long-term storage. For each experiment, nanoparticles were prepared fresh from lyophilized stocks and dissolved in PBS at a concentration of 10 mg/ml for in vitro experiments or in vivo injections.

PLGA nanoparticles were also prepared as follows. 60 mg of PLGA (50:50, Durect Corp.) were dissolved in 3 mL of chloroform in a glass test tube. For RAPA encapsulating NPs, 3 mg of RAPA (>99%, LC Laboratories) was added directly to the polymer solution. A primary emulsion was generated by adding 200 μL of water dropwise while continuously vortexing the polymer solution. For OVA encapsulating NPs, this water solution contained 2 mg of dissolved OVA. The primary emulsion was sonicated using an Ultrasonic Processor GEX600 model probe at 38% amplitude for a 10 s pulse, and then added dropwise to a continuously vortexed glass tube containing 4 mL of a 4.7% PVA solution with 0.3125 mg/mL avidin-palmitate conjugate. The resulting double emulsion was further sonicated with three 10 s pulses with 20 s breaks in an ice bath in between, before being transferred to a beaker containing 200 mL of 0.25% PVA. This solution was stirred at room temperature for 3 hours, after which the hardened particles were washed tree times by cycles of pelleting at 18,000 r.c.f. and resuspension in MilliQ water. Washed NPs were flash-frozen in liquid nitrogen and lyophilized for multiple days to enable long-term storage. NPs were stored at −20° C. until use and prepared from lyophilized stocks for each experiment.

Characterization of Nanoparticles

Nanoparticle size was quantified using the NANO-SIGHT® particle tracking system (Nanosight, Ltd., Wiltshire, UK). Particle morphology was captured by scanning electron microscopy (SEM). RAPA loading in nanoparticles was calculated by dissolving RAPA nanoparticles in DMSO at 1 mg/ml, then adding 1N NaOH at a 50:50 ratio to degrade RAPA and yield its ring-opened isomer. The formulation of the ring-opened isomer resulted in a yellow solution, the intensity being dependent on the concentration of RAPA. The absorbance was measured on the spectrometer and the concentration of RAPA per mg of particle was calculated based on the standard curve. Rapa loading was measured by diluting the DMSO solution 10-fold in 1 N NaOH to generate the degradation product, seco-RAPA, which was then measured by its absorbance at 400 nm. OVA loading in nanoparticles was calculated by dissolving OVA nanoparticles in DMSO, then by performing a microBCA protein assay.

Animals and Nanoparticle Injections

Female C57BL/6J and OT-II mice were purchased from Jackson Labs, at the age of 8-10 weeks. All animal work was performed under protocols that have been approved by the Yale Institute of Animal Care and Use Committee. For injections, nanoparticles were freshly prepared at 10 mg/ml concentration and each OT-II mouse was injected with either 2 mg of empty PLGA nanoparticles or RAPA and OVA nanoparticles.

Cell Culture

All isolated BMDCs or T cells were cultured in RPMI-1640 (Life Technologies) supplemented with 10% FBS (Gibco), Pen/Strep, MEM Vitamin solution, pyruvate, non-essential amino acids, and beta-mercaptoethanol (Life Technologies).

Generation and Isolation of BMDCs and OT-H T Cells

Bone marrow-derived dendritic cells (BMDCs) were generated as described by Zanoni et al. Generation of mouse bone marrow-derived dendritic cells (BM-DCs) (2009). Briefly, bone marrow progenitor cells were isolated from the femur of C57BL/6J mouse and cultured with media containing 20 ng/ml of GM-CSF. Cells were replenished with fresh media after 5 days of culture and collected after 48 hours of media replenishment. Naïve CD4 T cells and T cells were collected from OT-II splenocytes by using naïve CD4 T cell or CD3 T cell isolation kit (STEMCELL Technologies), respectively.

Flow Cytometry and Analysis

When ready for flow cytometry (FACS) analysis, cells were transferred to a 96-well U-bottom plate and spun at 500 g for 5 minutes. Cells were then washed with PBS and stained with LiveDead Zombie NIR (Thermo Fisher) at 1:1000 dilution for 15 minutes in the dark. Cells were washed two times with FACS buffer (PBS with 10% FBS) and then treated with Fc block at 1:500 dilution for 15 minutes in the dark at 4° C. Cells were then stained with fluorescent antibodies (eBiosciences or Biolegends) diluted at 1:100 or 1:200 in FACS buffer for 15 minutes in the dark at 4 C. After staining, cells were washed twice and fixed in 1% PFA.

For intracellular staining, cells were fixed and permeabilized with Fix/Perm buffer (Intracellular Fixation and Permeabilization Kit, eBiosciences) overnight in 4° C. Cells were washed with Perm/Wash buffer and then stained with Foxp3 antibody (eBioscience) for 45 minutes in the dark. After washing with Perm/Wash, cells were placed in PBS for up to 24 hrs before FACS analysis.

FACS was performed by either LSR-II (Becton Dickinson) or Attune NxT flow cytometer. Sorting was performed on FACSAria (Becton Dickinson). All FACS data was analyzed on FlowJo software (Tree Star Inc., Ashland, Oreg.).

ELISA

Supernatants from cultured DCs were collected to measure TGF-β and IL-10 secretion by using ELISA kits (Becton Dickinson), following the manufacturer's instructions. TGF-β was first activated by adding 0.4N HCl for 1 hr in 37° C. and then neutralizing with 1 M NaOH.

In Vitro Treg Suppressive Assay

CD25+ Tregs were generated by culturing nanoparticle-treated BMDCs with OT-II naïve CD4 T cells for 72 hours. CD25+ cells (suppressor cells) were sorted on FACSAria and added to the mixture of DCs pulsed with $OVA_{323-339}$ peptide and CFSE-stained OT-II T cells (responder cells). The ratio of responder cells and suppressor cells were titrated. After 72 hrs, suppression was analyzed by gating out the suppressor cells and by measuring the degree of CFSE dilutions, which showed proliferation of responder cells. Percent suppression was calculated by dividing $CFSE^{lo}$ population of responder cells from the positive control (no suppressor cells) and subtracting the resultant from 1.

Results

Duration of Soluble RAPA Treatment, but not Soluble OVA, Impacts DC Phenotype

DCs are one of the best antigen presenting cells that express costimulatory molecules and present antigens, which are modulated by mTOR signaling and antigen processing, respectively. The duration of DC exposure to RAPA and OVA affected the phenotype of DCs. DCs from the bone marrow (BMDCs) were harvested and treated with 100 ng/ml of free RAPA or 2 µg/ml of free OVA for either 72 hours or for 24 hours and analyzed by FACS. In all following experiments, BMDCs were gated on CD11c+, live cells, and surface markers of BMDCs were analyzed by flow cytometry. Compared to BMDCs treated with RAPA for 24 hours (RAPA 24 hrs), BMDCs treated with 72 hours of RAPA (RAPA 72 hrs) showed diminished expression of surface markers, such as PD-L1, CD80, CD86, and MHC 11 (FIG. 1A). However, no differences were observed for BMDCs treated with OVA for various times (FIG. 1B), showing that duration of RAPA exposure to DCs is a crucial aspect in downregulation of the costimulatory molecules and antigen presentation.

Figure 1B:
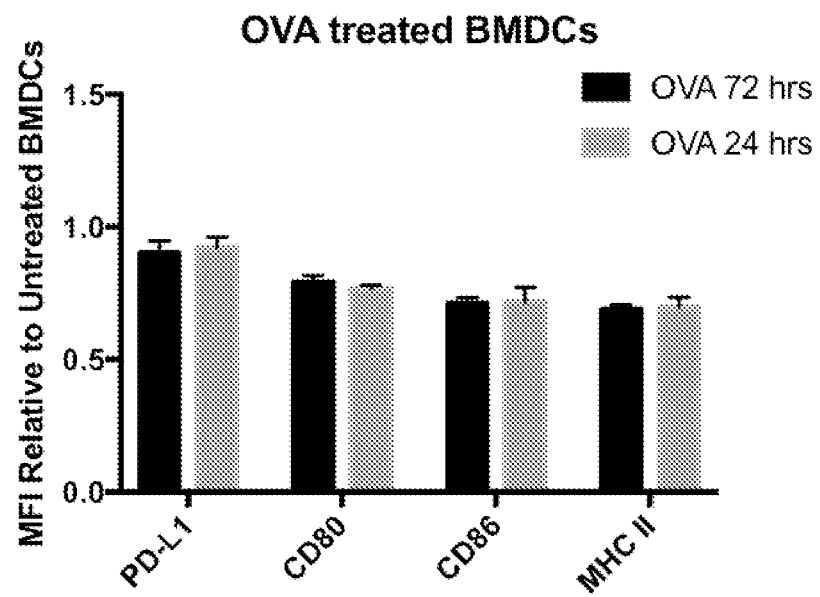

Both OVA and RAPA are expected to interact with DCs through the antigen processing and presentation pathways, and through mTOR signaling, respectively, and its subsequent effects on costimulatory marker expression and cytokine production. BMDCs were treated with soluble agents (100 ng/ml of RAPA or 2 µg/ml of OVA) for 24 or 72 hours. The phenotypic profile, as assessed by expression of canonical DC maturation markers (PD-L1, CD80, CD86, and MHC II) was analyzed by flow cytometry analysis (Gating strategy for analysis was on live, CD11c+ dendritic cells). Extended duration of BMDC exposure to RAPA (RAPA 72 hrs vs RAPA 24 hrs) resulted in reduced expression of all markers (FIG. 1A). In contrast, irrespective of the exposure duration, no differences in marker expression were observed for BMDCs treated with the antigen (OVA) alone (FIG. 1B).

Figure 1C:
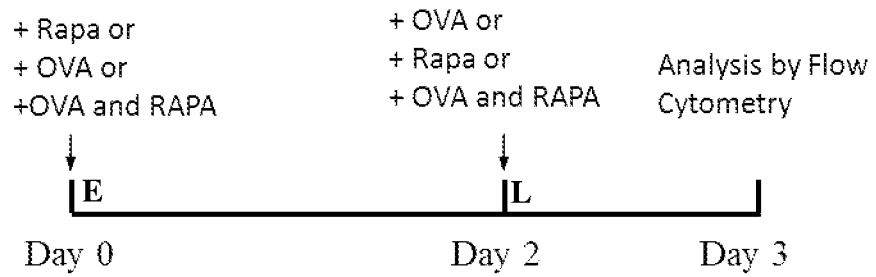
FIG. 1C is a diagram showing the experimental timeline for early (E) and late (L) treatments of BMDCs with either OVA, or RAPA, or Both OVA and RAPA. BMDCs were either first treated with rapamycin then OVA 48 hours after (RAPA$_E$/OVA$_L$), OVA then RAPA 48 hours later (RAPA$_L$/OVA$_E$), RAPA and OVA for 72 hours (RAPA$_E$/OVA$_E$), or RAPA and OVA for 24 hours (RAPA$_L$/OVA$_L$). BMDCs were harvested 24 hours later and analyzed by FACS.
Figure 1D:
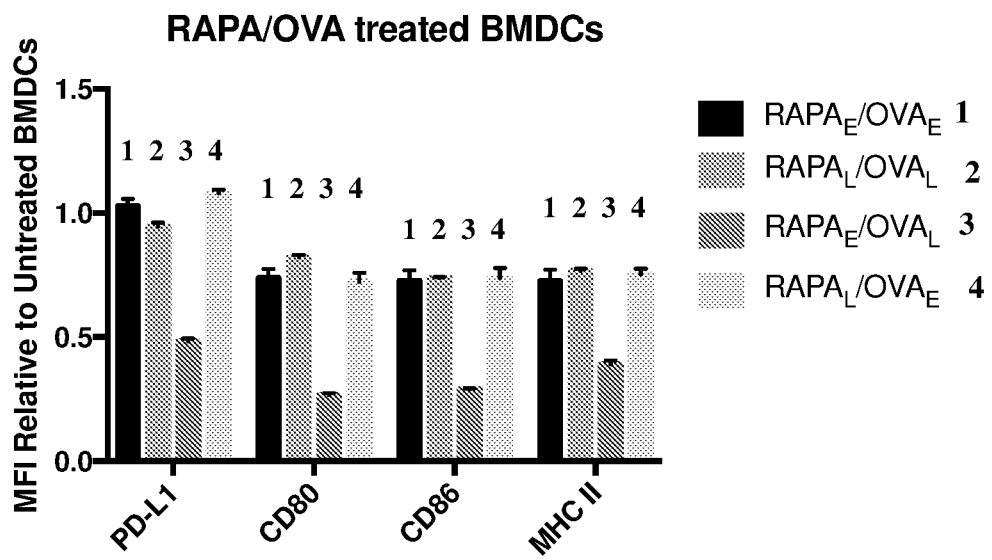
FIG. 1D is a diagram showing relative expression (MFI Relative to Untreated BMDCs) of PD-L1, CD80, CD86, and MHCII in BMDCs treated with conditions presented in FIG. 1C. Results are representative of two or more experiments.

Sequence Matters: Treatment with Free RAPA Prior to Free OVA is Preferred for Downregulation of DC Surface Markers The kinetics of mTOR inhibition by RAPA and OVA presentation on MHC II are quite different, emphasizing that there is a need for fine tuning of RAPA and OVA exposure kinetics for maximal tolerogenic response. While RAPA is a highly potent immunosuppressant, presence of an antigen and its loading can upregulate costimulatory markers and weakly activate DCs, suggesting that two modulators required for antigen-specific tolerance counterbalance each other in DC physiology. The importance of sequential RAPA and OVA delivery was investigated by comparing BMDCs treated with RAPA or OVA for 72 hrs and OVA or RAPA for 24 hrs, respectively. $RAPA_E/OVA_L$ BMDCs expressed the lowest levels of PD-L1 (co-inhibitory surface marker), CD80, CD86 (co-stimulatory surface markers), and MHC II (FIG. 1D). There were no statistically significant differences between free $RAPA_E/OVA_E$ versus free $RAPA_L/OVA_L$ (FIGS. 1C and 1D), showing that a preferred sequential release of RAPA and OVA exists for most effective tolerance. These results show that free RAPA treatment followed by free OVA treatment is most preferred for lower expression of co-stimulatory/inhibitory molecules and antigen presentation.

Synthesis of PLGA Nanoparticles Containing RAPA or OVA, Characterization, and In Vitro Validation A nanoparticle platform to deliver RAPA and OVA with sustained release was developed and their functionalities characterized. Nanoparticles were approximately 250 nm in diameter, with or without RAPA or OVA encapsulation. The nanoparticles were evenly spherical overall by SEM. Loading of OVA and RAPA were approximately 26.7 µg and 9.8 µg per mg of particle, which yielded around 53.4% and 19.6% encapsulation efficiency, respectively (Table 3). In proceeding in vitro experiments, nanoparticles were added at a concentration of 100 µg/ml to normalize to free concentration of 100 ng/ml and 2 µg/ml of free RAPA and free OVA.

The dynamic light scattering (DLS)-generated size distributions of OVA and RAPA nanoparticles, and showed Z-average of 250.3 nm, standard deviation of 3.72, and polydispersity index of 0.12.

TABLE 3

Loading of PLGA nanoparticles containing OVA or RAPA.

|  | OVA Loading (µg/mg NP) | RAPA Loading (µg/mg NP) |
|---|---|---|
| OVA | 26.7 ± 4.03 | 0 |
| RAPA | 0 | 9.8 ± 0.20 |

Figure 1E:
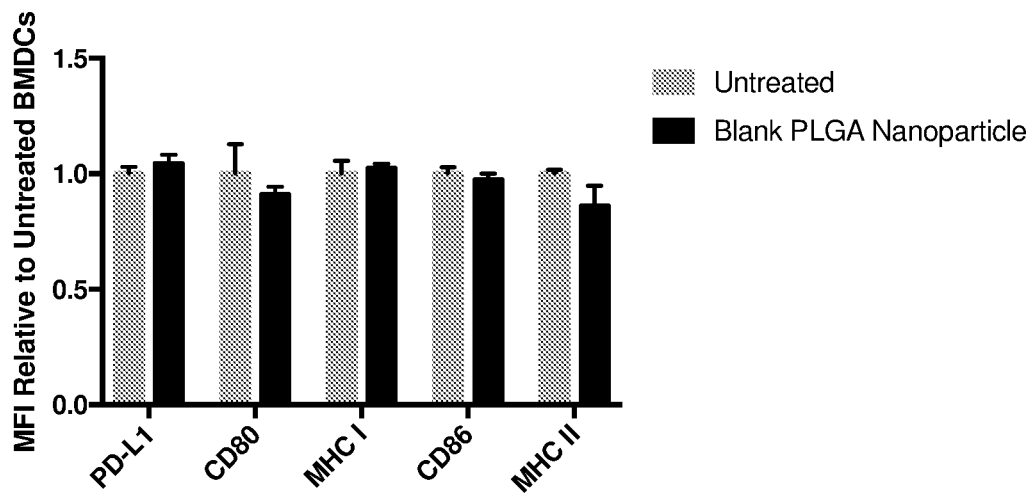
(FIG. 1E). BMDCs have been treated with either PBS or blank PLGA nanoparticles (100 μg/ml). Three days later, BMDCs were harvested and DC surface markers were analyzed by flow cytometry (N=3). ***$p<0.01$.

To ascertain that the observed effects are not due to PLGA nanoparticles alone, DCs were treated with either PBS or blank PLGA nanoparticles. DCs treated with empty nanoparticles showed no difference in expression of PD-L1, CD80, CD86, and MHC II, indicating that PLGA nanoparticles by themselves have no intrinsic effect on BMDC phenotype (FIG. 1E).

Figure 2A:
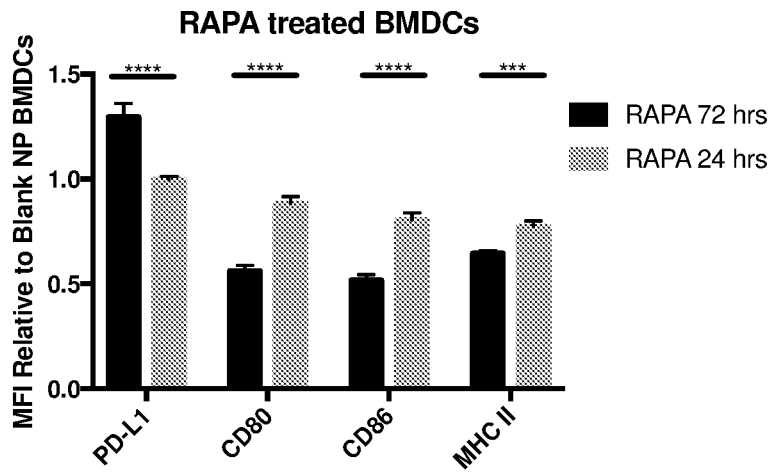
FIGS. 2A and 2B are graphs showing the temporal effect of RAPA or OVA on relative expression (MFI Relative to Blank NP-treated BMDCs) of PD-L1, CD80, CD86, and MHCII in BMDCs treated with RAPA nanoparticles (FIG. 2A) or OVA nanoparticles (FIG. 2B) (100 μg/ml of particles) for either 72 hrs or 24 hrs. *$p<0.01$, **$p<0.001$.
Figure 2B:
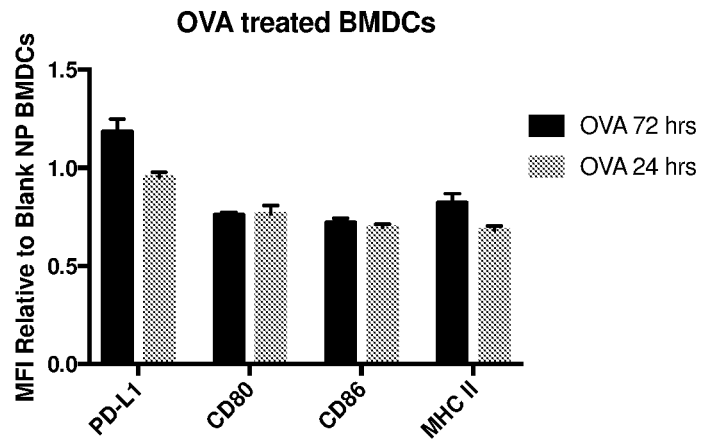

Treatment of DCs with RAPA Nanoparticles Prior to OVA Nanoparticles Increases PD-L1 Expression, but Decreases Co-Stimulatory Molecules Validated RAPA and OVA nanoparticles were added to BMDCs for either 72 hrs or 24 hrs, and expression of surface markers was analyzed by FACS. RAPA 72 hr-pulsed BMDCs expressed lower levels of co-stimulatory molecules CD80 and CD86 compared to DCs treated with blank nanoparticles (FIGS. 2A and 2B), which was consistent with observations from FIGS. 1A-1D that prolonged exposure to RAPA decreases CD80, CD86, and MHC II. Co-inhibitory molecule PD-L1 was increased by longer exposure to RAPA nanoparticles (FIGS. 2A and 2B). Similarly to free OVA, prolonged OVA nanoparticle exposure had no major effect on BMDC surface markers (FIGS. 2A and 2B), showing that prolonged RAPA nanoparticle delivery upregulates PD-L1 while lowering expression of co-stimulatory markers and antigen presentation. Because prolonged RAPA delivery by nanoparticles increased PD-L1, contrary to free RAPA, this suggested that RAPA nanoparticles could be more potent than free RAPA in induction of tolerance.

Figure 3A:
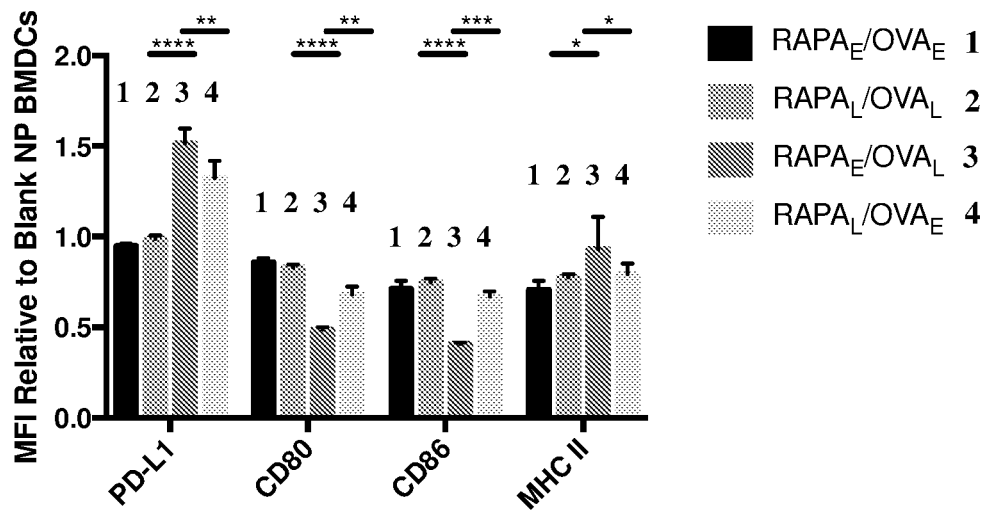
FIG. 3A is a bar graph showing relative expression (MFI Relative to Blank NP BMDCs) of PD-L1, CD80, CD86, and MHCII in BMDCs when the cells were treated with PLGA NPs at different time points: either first treated with rapamycin then OVA 48 hours after (RAPA$_E$/OVA$_L$), OVA then RAPA 48 hours later (RAPA$_L$/OVA$_E$), RAPA and OVA for 72 hours (RAPA$_E$/OVA$_E$), or RAPA and OVA for 24 hours (RAPA$_L$/OVA$_L$).

The influence of sequential delivery of RAPA and OVA by nanoparticles on DC phenotype was investigated. BMDCs were treated with either RAPA or OVA nanoparticles, followed by OVA or RAPA nanoparticles, respectively. $RAPA_E/OVA_L$ group demonstrated considerably lower expression of costimulatory molecules, CD80 and CD86, than $RAPA_L/OVA_E$, $RAPA_E/OVA_E$, or $RAPA_L/OVA_L$ (FIG. 3A). However, most importantly, $RAPA_E/OVA_L$ had more PD-L1$^{hi}$ BMDC population compared to $RAPA_L/OVA_E$, RAPA/OVA$_E$, and $RAPA_L/OVA_L$ (FIG. 3A). Similarly to the free RAPA and OVA experiment, no changes were seen in $RAPA_E/OVA_E$ and $RAPA_E/OVA_L$ DCs, implying that sequence of RAPA and OVA delivery by nanoparticles can be a key determinant in DC phenotype. In addition, $RAPA_E/OVA_L$ showed a slight increase in MHC II$^{hi}$ population (FIG. 3A), which suggests that more efficient antigen presentation and induction of T cells could be expected.

Delivery of RAPA Nanoparticle Followed by OVA Nanoparticle Generates PD-L1 Tolerogenic DCs Tolerogenic DCs are a subset of DCs that exhibit immunoregulatory functions and induce tolerance by fostering Treg development. Tolerogenic DC's importance in immune tolerance has been accentuated in several autoimmune disease models, including Graft vs. Host Disease (Stenge et al., *Blood*, 119:5088-103 (2012)). These immunoregulatory DCs are defined as DCs that express lower levels of MHC and co-stimulatory molecules, while producing high levels of co-inhibitory molecules, such as PD-L1 (Mildner and Jung, *Immunity*.40(5):642-656 (2014)).

Figure 3B:
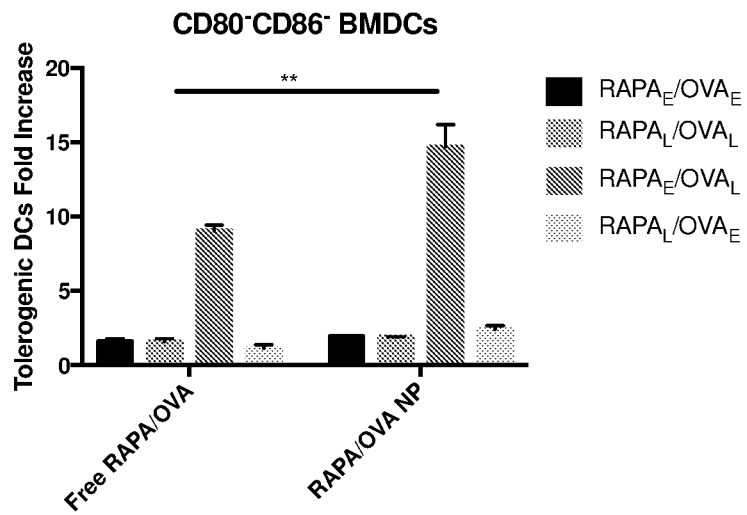
FIG. 3B is a bar graph showing the change in tolerogenic DCs (fold increase relative to untreated) with the different treatments. DCs treated with nanoparticles at different timepoints were analyzed and gated by the expression levels of their surface markers. Tolerogenic DCs were defined as CD11c$^+$MHCI$^{lo}$MHCII$^{lo}$PDLI$^{hi}$CD80$^-$CD86$^-$ DCs.

Gating on CD11c+MHC I$^{lo}$MHC II$^{lo}$PD-L1$^{hi}$CD80$^{lo}$CD86$^{lo}$ DC populations revealed that $RAPA_E/OVA_L$ DCs induced the development of tolerogenic DCs (FIG. 3B). In addition, nanoparticle $RAPA_E/OVA_L$ showed superiority over free $RAPA_E/OVA_L$(FIG. 3B), showing that nanoparticle delivery of RAPA and OVA is superior in developing tolerogenic DCs through upregulation of PD-L1. It was reported that tolerogenic DCs share similar surface marker profiles to immature DCs; however, in addition to low levels of MHC II and co-stimulatory molecules, a well-noted characteristic of tolerogenic DCs is secretion of anti-inflammatory cytokines, such as TGF-β and IL-10 (Raker et al., *Frontiers in Immunology*, 6, 569 (2015)). Nanoparticle $RAPA_E/OVA_L$ DCs produced the highest levels of TGF-β and IL-10 (FIG. 3C-3D), indicating that tolerogenic DCs produced by earlier delivery of RAPA nanoparticles are anti-inflammatory.

Consistent with results from the soluble agents, early exposure to RAPA NPs led to the most significant decreases in CD80 and CD86. However, with nanoparticle-mediated delivery, these lower levels of costimulatory receptors were paired with the highest upregulation of the co-inhibitory receptor, PD-L1. Defining a tolerogenic DC as a PD-L1 high, CD80/86 low population, both soluble and NP treatment, priming with RAPA prior to OVA exposure ($RAPA_E/OVA_L$) was best at inducing this DC phenotype (FIGS. 3A and 3B).

Figure 3C:
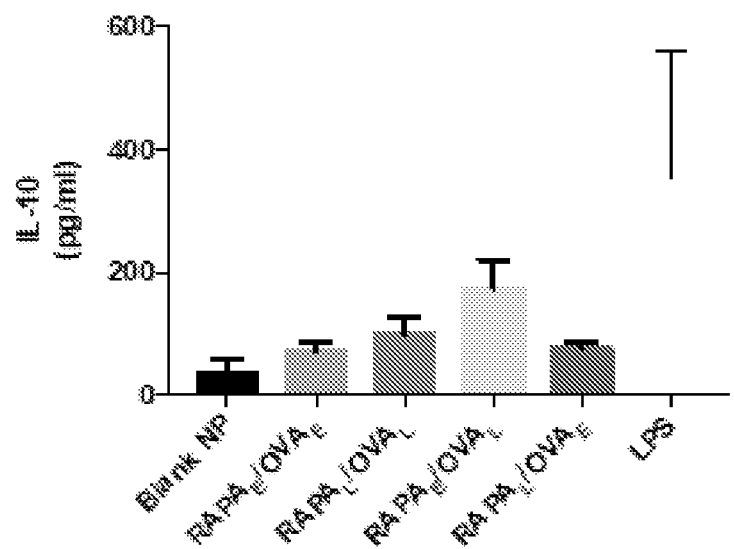
FIGS. 3C and 3D are bar graphs showing the amount of IL-10 (pg/ml, FIG. 3C) and TGF-β (pg/ml, FIG. 3D) secreted by the DCs treated with nanoparticles at different timepoints, as described for FIG. 3A. Supernatants from DCs treated with nanoparticles (untreated is the treatment with Blank NPs in FIG. 3D), at different timepoints were collected and the level of IL-10 and TGF-β were measured by ELISA. Results are representative from two independent experiments. LPS was used as a positive control.
Figure 3D:
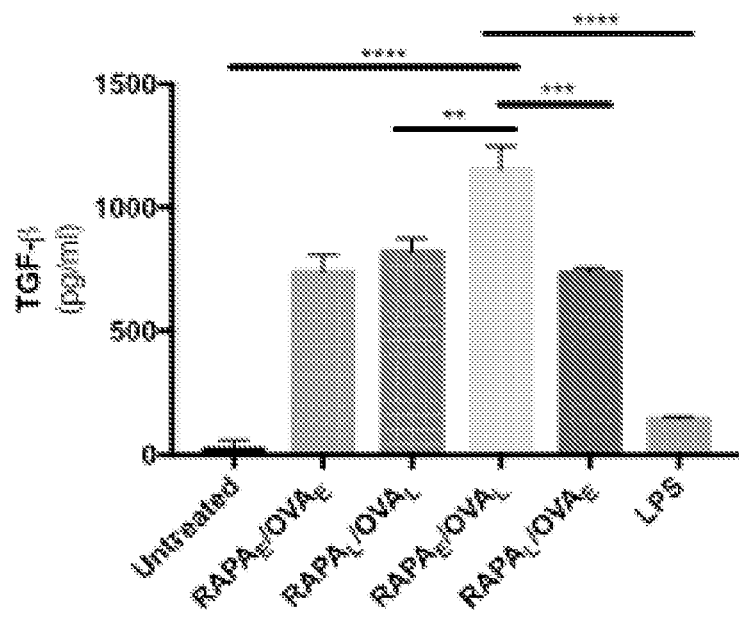

This result was far more pronounced when RAPA and OVA were delivered by nanoparticles. The $RAPA_E/OVA_L$ group was the only group that yielded significant tolerogenic profile enhancements, supporting that delivery sequence of adjuvant and antigen is an important determinant of DC response. This was further supported by the observation that this delivery sequence also promoted DCs to secrete the highest levels of the anti-inflammatory cytokines, IL-10 and TGF-β (FIGS. 3C-3D).

Tolerogenic DCs Produced by Preferential, Earlier Release of RAPA Nanoparticles Induce Development of Highly Suppressive Antigen-Specific Tregs CD4$^+$ Tregs are major players of immune modulation and suppress inflammatory effector T cells. Tolerogenic DCs are major inducers of Tregs through production of anti-inflammatory cytokines such as TGF-β and IL-10 (Maldonado and von Andrian. *Advances in immunology*, 108:111-65 (2010)). To test this, nanoparticle-pulsed DCs were co-cultured with transgenic T cells that express T cell receptors specific for MHC II-loaded OVA (OT-II). After three days of co-culture, OT-II T cells were collected and analyzed for CD25$^+$Foxp3$^+$ expression by FACS for identification of Tregs.

Figure 4A:
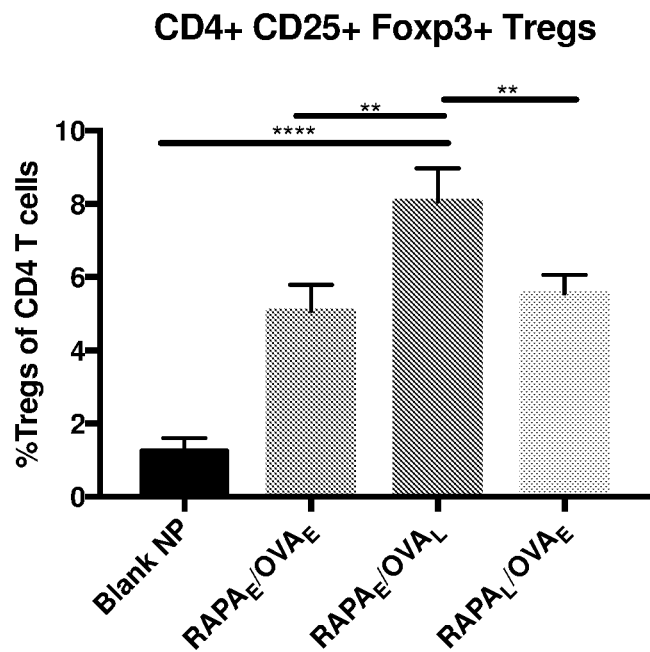
FIG. 4A is a bar graph showing the change in percent Tregs of CD4 T cells after nanoparticle-pulsed DCs were isolated, washed in PBS, and co-cultured with naïve CD4 OT-II T cells at a 1:5 ratio for 72 hours. After 72 hours of co-culture, cells were collected and analyzed by FACS. The FACS data were obtained from live, CD3+CD4+ cells.
Figure 4B:
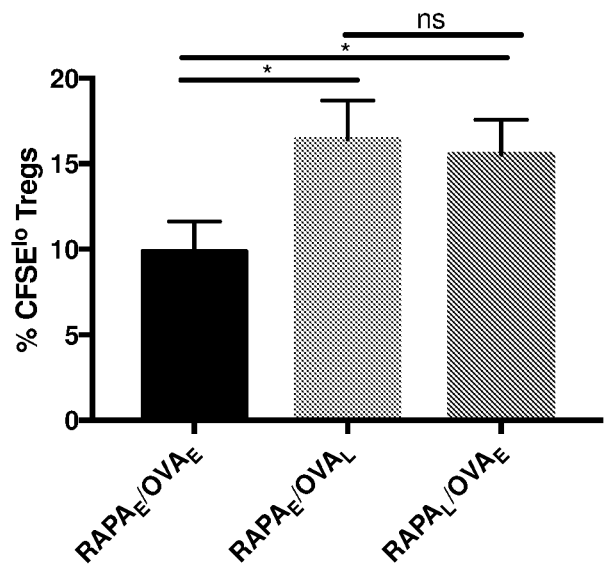
FIG. 4B is a bar graph showing proliferation (% CFSE$^{lo}$ Tregs) of induced Tregs by nanoparticle-pulsed DCs as analyzed by CFSE dilution. The FACS data were obtained from live, CD3+CD4+CD25+Foxp3+ cells.

Nanoparticle $RAPA_E/OVA_L$ DCs increased the frequency of Tregs by two-fold compared to $RAPA_E/OVA_E$ or $RAPA_L/OVA_E$ DCs (FIG. 4A). No difference was observed in Treg induction between $RAPA_E/OVA_E$ and $RAPA_L/OVA_L$, emphasizing the importance of sequential delivery of RAPA and OVA. Only a modest increase of Treg proliferation was observed in $RAPA_E/OVA_L$ DCs (FIG. 4B). Therefore the preferred sequential delivery of RAPA and OVA can also generate antigen-specific CD25$^+$Foxp3$^+$ Tregs, which are essential for induction of immune tolerance.

Figure 4C:
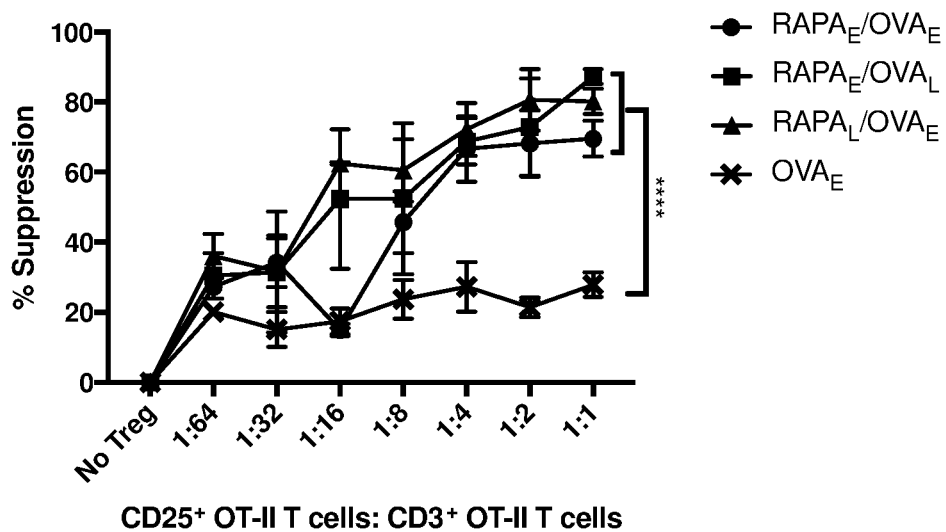
FIG. 4C is a line graph showing percent suppression (% Suppression) of proliferation in CFSE-stained OT-II T cells co-cultured with CD25+ T cells compared to control (No CD25 T cells). DCs pulsed with RAPA and OVA nanoparticles at different timepoints or just OVA for 72 hours (OVA$_E$) were co-cultured with non-CFSE stained naive CD4 OT-II T cells for 72 hrs. CD25+ Tregs were then sorted and added at a known ratio to splenic DCs pulsed with OVA$_{323-339}$ peptide and co-cultured with CFSE-stained OT-II T cells at a 1:5 ratio. CD25+ T cell-mediated suppression was measured by the proliferation decrease of CFSE-stained OT-II T cells compared to control (No CD25 T cells). Proliferation suppression of CFSE-stained T cells at a 1:1 ratio of CD25+ Tregs to CFSE-stained OT-II T cells is shown.

The suppressive ability of Tregs can be measured by the decrease of effector T cell proliferation when co-cultured with Tregs (Collison and Vignali, In Vitro Treg Suppression Assays. *Methods in Molecular Biology* (Clifton, N.J.), 707: 21-37 (2011)). To quantitate the antigen-specific suppression mediated by OVA-specific Tregs generated by nanoparticle-pulsed DCs, CD25+ T cells were sorted after generating Tregs, as described for FIG. 4A. Sorted CD25$^+$ T cells were transferred to OVA$_{323-339}$ peptide pulsed splenic CD11c$^+$ DCs cultured with CFSE-stained OT-II T cells. The inhibitory effect of transferred CD25$^+$ T cells on OT-II T cell proliferation was measured by quantifying CFSE dilution of OT-II T cells. Only a subset of CD25$^+$ T cells are suppressive, as CD25 is also a marker for T cell activation after experiencing an antigen. As a result, CD25+ T cells generated by OVA nanoparticle-pulsed DCs were added as a baseline control. It was found that Tregs generated by RAPA and OVA nanoparticle-pulsed DCs were much more suppressive compared to Tregs generated by OVA nanoparticle-pulsed DCs (FIG. 4C). Altogether, these results show that nanoparticle-pulsed DCs induced development of highly suppressive antigen-specific Tregs.

The tolerogenic DCs generated by the RAPA$_E$/OVA$_L$ NP delivery were tested for inducing functionally suppressive, OVA-specific Tregs. To test this, NP-treated DCs were co-cultured sequentially with transgenic T cells expressing OVA-specific T cell receptors (OT-II cells). After three days, all co-cultures were observed to have expansion of CD25$^+$ Foxp3$^+$ Tregs, with exception of a control group, in which the DCs were primed with empty nanoparticles (FIG. 4A). This expansion was significantly greater in the RAPA$_E$/OVA$_L$ co-culture group (FIG. 4A). No significant differences in Treg expansion were observed between cases where DCs were treated simultaneously with antigen and adjuvant (RAPA$_E$/OVA$_E$, RAPA$_L$/OVA$_L$) or when OVA exposure preceded RAPA treatment (RAPA$_L$/OVA$_E$). An increase of Treg proliferation was observed with the RAPA$_E$/OVA$_L$ co-culture (FIG. 4B). Given that Tregs are major player in immune modulation that function to suppress inflammatory effector cells, the impact of sequential DC treatment on Treg induction translated to an enhanced effect in suppression of the inflammatory response. To explore the effects on antigen-specific suppressive capacity introduced by temporally staggering antigen and adjuvant, the decrease of effector T cell proliferation when co-cultured with the induced Tregs was assessed. CD25+ Tregs were sorted after Treg induction in the initial co-culture and then added to a secondary co-culture containing both splenic CD11c$^+$ DCs pulsed with the OVA$_{323-339}$ peptide and freshly isolated, CFSE-labeled OT II T cells. CD25+ Tregs generated by RAPA and OVA NP-pulsed DCs displayed about four times more suppressive function than CD25+ Tregs generated by only OVA NP-pulsed DCs (FIG. 4C). However, with the normalization in suppressor to effector ratio contained within the in vitro Treg functional assay protocol, it became clear that while sequence of delivery may affect the amplitude of the promoted Treg expansion, the Tregs generated have potent suppressive capacity regardless of the DC priming sequence.

Preferred Sequential Delivery of RAPA and OVA In Vivo Highly Increases PD-L1$^{hi}$ Antigen Presenting Cells While co-delivery of RAPA and OVA in vivo has been described in many studies, the relevance of sequential delivery of RAPA and OVA on tolerance induction has not been fully elucidated in mice. It was verified whether earlier delivery of RAPA would enhance PD-L1$^{hi}$ antigen presenting cells in vivo.

Animals were vaccinated with RAPA and OVA NPs according to the staggered sequences used in all in vitro studies. PD-L1 expression in RAPA/OVA$_L$ macrophages and DCs was increased more than five-fold compared to control (FIGS. 5A and 5B), showing that mice receiving RAPA nanoparticles prior to OVA nanoparticles develop the highest levels of tolerogenic antigen presenting cells, consistent with the in vitro results.

Figure 5A:
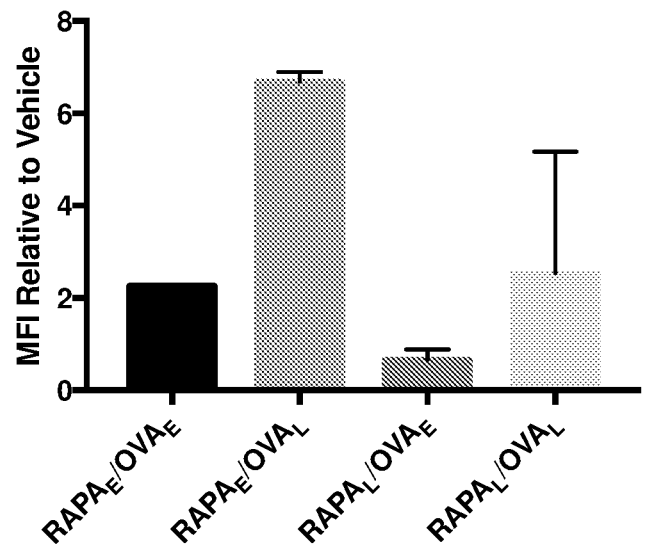
FIGS. 5A and 5B are bar graphs showing relative expression (MFI Relative to Vehicle) of PD-L1 in F4/80+ macrophages (FIG. 5A), or in CD11c+CD11b+ DCs (FIG. 5B) obtained from spleens of mice treated with NPs containing either OVA then RAPA 48 hours later (RAPA$_L$/OVA$_E$), RAPA and OVA for 72 hours (RAPA$_E$/OVA$_E$), or RAPA and OVA for 24 hours (RAPA$_L$/OVA$_L$). Mice were injected with nanoparticles (i.p.) (2 mg/mouse) at different timepoints (E=72 hours prior to harvest; L=24 hours prior to harvest). Mice were sacrificed and collected splenocytes were analyzed by FACS. PD-L1 expression on macrophages (CD11b+F4/80+) or CD11b+ DCs (CD11c+CD11b+) is shown, (N=4).
Figure 5B:
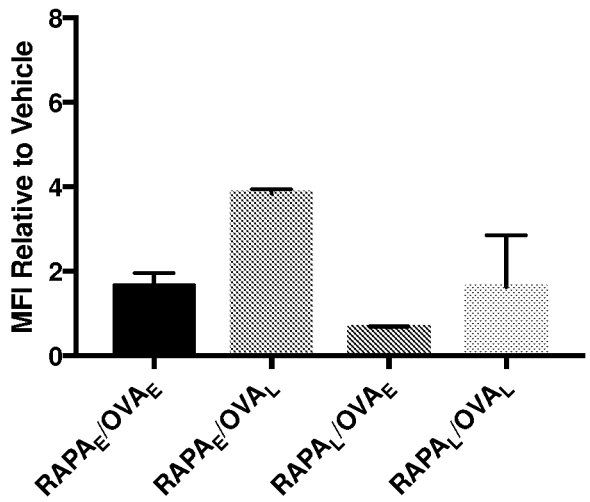

Although the differences in co-stimulatory markers CD80 and CD86 were not statistically significant between the groups, PD-L1 expression in RAPA$_E$/OVA$_E$ macrophages and DCs were increased by more than five-fold compared to control (FIGS. 5A and 5B). Increased PD-L1$^{hi}$ antigen presenting cells suggested that mice receiving RAPA nanoparticles prior to OVA nanoparticles develop tolerogenic antigen presenting cells, consistent with in vitro results, and could program a tolerogenic response in vivo.

These results show that in a combinatory delivery system of RAPA and OVA, RAPA (immunomodulatory agent causing tolerance) delivery prior to OVA (antigen) is preferred for induction of tolerance, and that sequential delivery of immunosuppressive agent and antigen should be considered for most effective tolerogenic priming of DCs and T cells for treatment of autoimmune diseases.

Colocalizing antigen and adjuvant to the same DC is essential for qualitative control over the nature of the immune response and the desired vaccination outcome. This has led to the emergence of nanocarrier technologies in vaccine development. Such carriers afford enhanced accumulation of antigen in APCs, cellular colocalization of antigen and adjuvant, and, ultimately, the potential to skew the DC response in an immunogenic or tolerogenic manner depending on the choice of adjuvant.

The combination of a tolerogenic adjuvant, such as rapamycin (RAPA), with antigen is a promising strategy for the induction of antigen-specific tolerance. However, an appreciation for the different mechanisms of action of the two primary vaccine components highlights that simply meeting the "spatial colocalization criterion" may be insufficient for achieving an effective tolerogenic response. That is, simple co-delivery of both agents may not harmonize with the kinetic differences in the cellular responses to antigen and adjuvant. While antigen processing and presentation begins within minutes of antigen exposure, the tolerogenic effects of an agent like RAPA involve integrated changes of intracellular signaling and gene expression that require significant time. Within the context of this kinetically-staggered response, the temporal order of exposure was adjusted to yield maximal responses.

Consistent with previous results, the nanoparticle-mediated delivery of RAPA and OVA was superior to delivery of the soluble agents. Earlier delivery of RAPA by nanoparticles increased the tolerogenic DC population, through upregulation of PD-L1, decreased expression of the co-stimulatory molecules CD80 and CD86, and increased secretion of the immunosuppressive cytokines IL-10 and TGF-β. The earlier delivery of RAPA to DCs also provided increased production of functionally suppressive Tregs.

Use of nanoparticles in vaccine formulation is largely fueled by the ability of such systems to facilitate the co-localization of multiple therapeutic agents at the cellular level. The ability of a vaccine to initiate a desired T cell response, whether immunogenic or tolerogenic, is dependent on cis-priming of the APC that will engage with the responding T cell at the immunological synapse. An optimal outcome will be realized only when the APC that encounters, engulfs, processes and presents the antigen of interest also encounters the adjuvant that has been included to skew the immunological response in a particular direction. Multiple reports have demonstrated the efficacy in the generation of antigen-specific tolerance of nanoparticle systems that co-encapsulate antigen with the tolerogenic adjuvant, RAPA. These studies highlight the immunosuppressive properties of the mTOR inhibitor, showing that RAPA treatment of APCs causes these cells to assume a tolerogenic phenotype through the downregulation of positive costimulatory markers, upregulation of negative costimulatory markers, inhibition of antigen processing and presentation, and the increased production of immunosuppressive cytokines. When antigen is co-delivered in this context, this results in an antigen presentation interaction and environment that favor the differentiation and proliferation of Tregs over effector T cells.

Figure 6A:
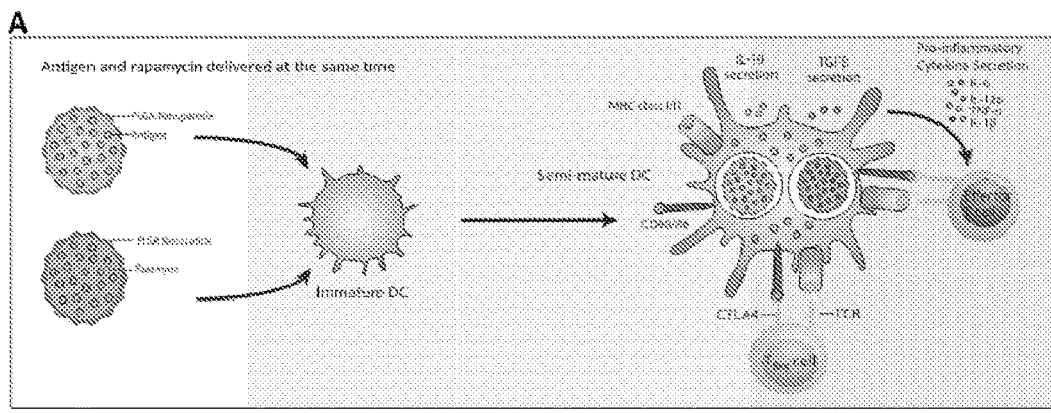
FIGS. 6A-6C are diagrams showing the different effector outcomes based on the temporal delivery of an antigen and rapamycin to the same dendritic cell (DC). A model of how temporal control of release induces tolerance is shown.
Figure 6B:
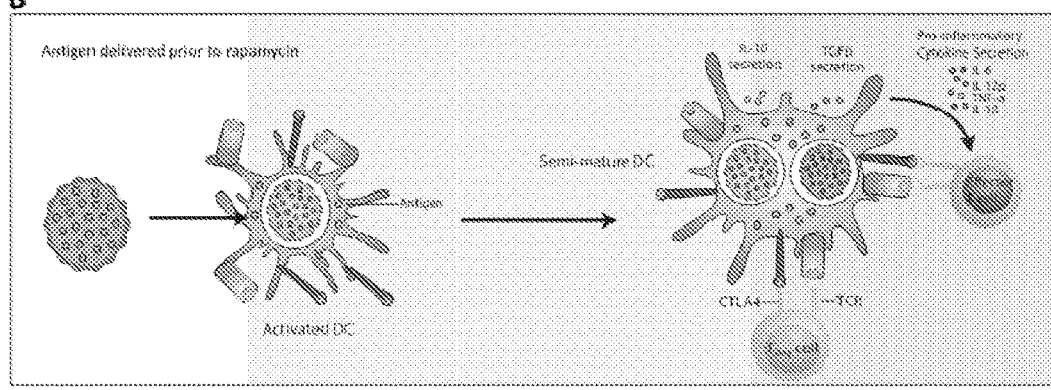
Figure 6C:
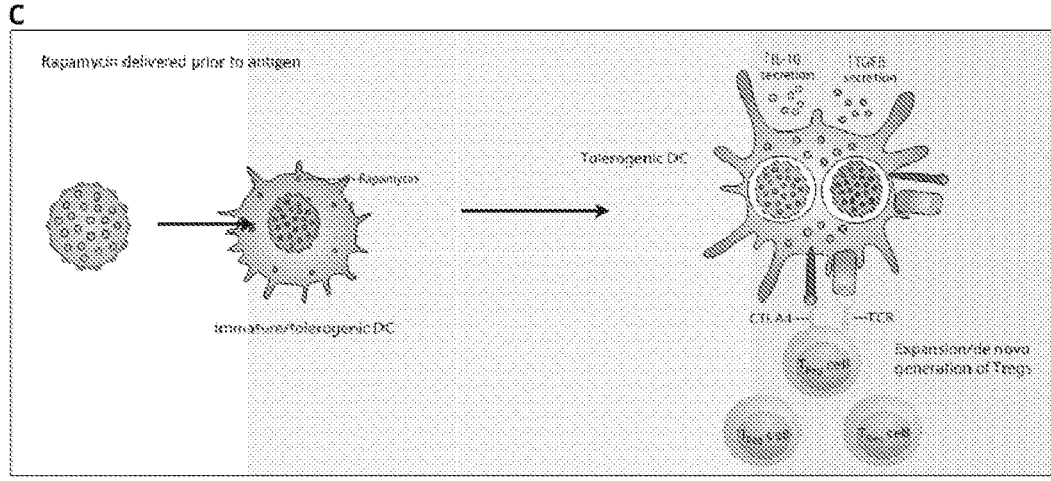
Figure 7A:
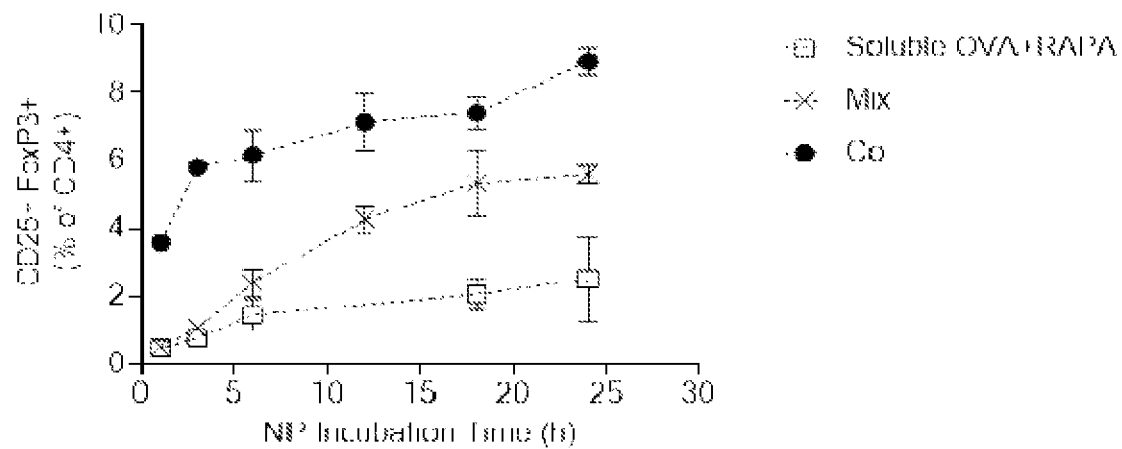
Figure 7B:
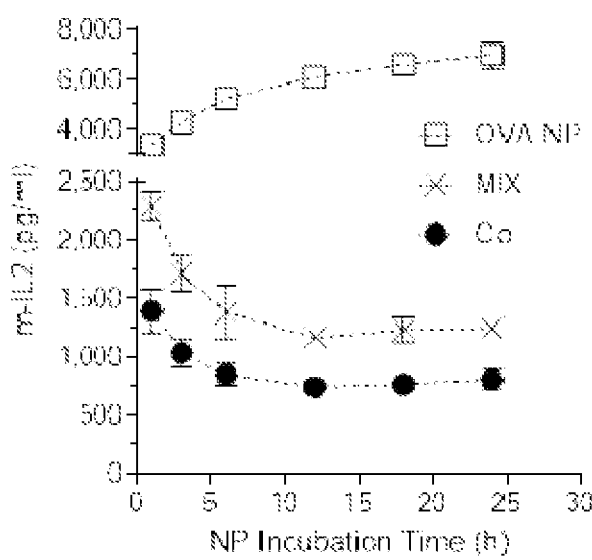

With the ability to execute selective dampening of immune system function, antigen-specific Tregs are widely believed to be the therapeutic target for intervention in autoimmune disease and avoidance of transplant rejection. While the antigen-RAPA NP has demonstrated efficacy in multiple animal models of autoimmune disease, it was unknown whether the kinetics of delivery of the two encapsulated agents could be tuned to yield an effective tolerogenic response. It is shown here that staggered delivery, in which DCs are exposed to RAPA before OVA, results in enhanced generation of tolerogenic DCs and subsequent antigen-specific T cell induction (FIGS. 6A-6C).

Example 2. Synthesis of STP with Spatial and Temporal Release of Agents

Figure 8C:
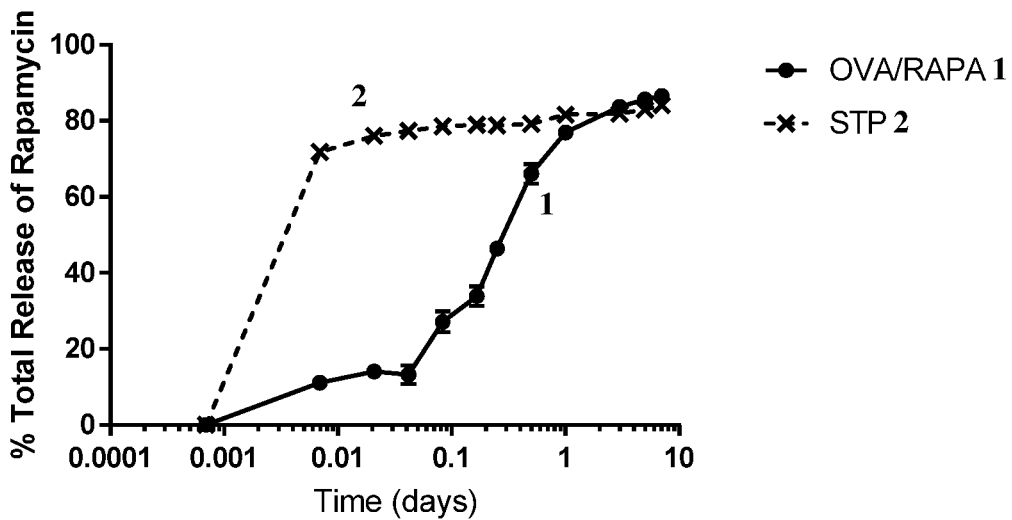
FIGS. 8C and 8D are graphs showing the percent (%) Total Release of Rapamycin (FIG. 8C) and Ovalbumin (FIG. 8D) from PLGA NP containing the antigen OVA and RAPA (1), or STP containing OVA in the core particle and RAPA in the tethered particle (2). Particles were incubated in PBS at 37° C., and supernatant was collected to measure the level of OVA and RAPA at each timepoint. (N=3; p-values calculated by student t-test for each timepoint).
Figure 8D:
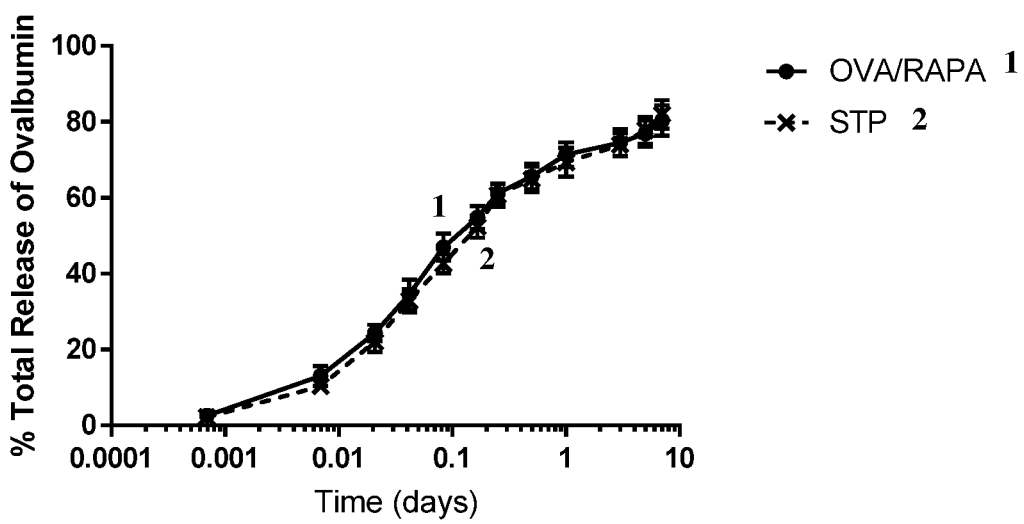

Spatiotemporally-Tuned Particles (STP), which achieve the preferential sequential release of co-localized rapamycin and antigen, were superior to the co-encapsulated antigen/ RAPA and antigen-only nanoparticles in development of CD4+ regulatory T cells (Tregs). In mice, STP also enhanced tolerance through expansion of naturally occurring Tregs (nTregs). STP prevented and cured mice from EAE. Furthermore, single-cell RNAseq revealed that macrophage type-2 (M2) was systemically increased as a result of STP administration in mice. Depletion of macrophages and PD-L1 expressing cells diminished the expansion of nTregs in STP-treated mice, highlighting the importance of STP-uptaking macrophages and the co-inhibitory biomarker PD-L1.

Materials and Methods

The STP containing OVA in the core particle and rapamycin (RAPA) in the tethered particle were prepared as follows. OVA was encapsulated in poly-lactic-co-glycolic acid nanoparticles as described in Example 1. For OVA encapsulation, 1.5 mg of OVA dissolved in 200 μL of water was added drop-by-drop while PLGA in chloroform was being vortexed. The primary emulsion containing dissolved RAPA or OVA was sonicated, which was added drop-by-drop to 3 ml of water containing 5% poly-vinyl-alcohol (Sigma-Aldrich) and 250 μL of 5 mg/ml avidin-palmitate. The resulting double-emulsion was sonicated to yield nano-sized droplets with encapsulated RAPA or OVA. Solvent was removed by stirring at room temperature for 4 hours. Nanoparticles were then washed three times in MilliQ water and lyophilized for long-term storage.

The resulting nanoparticles were attached to biotin-PEG-Cyclodextrin-RAPA complex by avidin-biotin interaction. Specifically, STP was synthesized through binding of avidin coated nanoparticles with biotin-RAPA-cyclodextrin complex. Biotin-RAPA-cyclodextrin (RAPA-CD) complex was formed by mixing of Biotin-PEG-NHS (EZ-link, Thermo Fisher Scientific) with amino-O-cyclodextrin (6-monodeoxy-6-monoamino hydrochloride) at 1:1 molar ratio, overnight at 4° C. The stable product, biotin-PEG-β-cyclodextrin was dialyzed overnight to remove any unreacted byproducts. Purified product was then mixed with RAPA at a 1:1 molar ratio, filtering out excess, unbound RAPA through a 40-μm strainer, and was lyophilized again and added to avidin-palmitate-coated nanoparticles. The amount of RAPA incorporated into cyclodextrin was quantified by reading the product dissolved in DMSO at 400 nm wavelength. The amount of RAPA-CD added to particles was always normalized to the amount of RAPA loaded in antigen/RAPA particles.

For each experiment, nanoparticles were prepared fresh from lyophilized stocks and dissolved in PBS at a concentration of 10 mg/ml for in vitro experiments or in vivo injections. The general method steps for forming the STP is presented in FIGS. 8A and 8B.

Nanoparticle size was quantified using the NANOSIGHT® (NanoSight Ltd, London, U.K.) particle tracking system (NanoSight, Ltd., Wiltshire, UK). Particle morphology was captured by scanning electron microscopy (SEM). RAPA loading in nanoparticles was calculated by dissolving RAPA nanoparticles in DMSO at 1 mg/ml, then adding 1N NaOH at a 50:50 ratio to degrade RAPA and yield its ring-opened isomer. The formulation of the ring-opened isomer resulted in a yellow solution, the intensity being dependent on the concentration of RAPA. The absorbance was measured on the spectrometer (400 nm wavelength on a spectrophotometer (Bio-rad)) and the concentration of RAPA per mg of particle was calculated based on the standard curve. OVA loading in nanoparticles was calculated by dissolving OVA nanoparticles in DMSO, then by performing a microBCA protein assay.

The release profiles for nanoparticles were obtained by dissolving nanoparticles in PBS and leaving in 37° C. for the duration of each timepoints. The supernatant was collected and antigen was quantified by microBCA. For RAPA, the supernatant was further mixed with Tween-80 and PEG400 to fully dissolve the RAPA.

Results

The STP (OVA-RAPA) showed spatial and temporal release of both agents, as shown in FIGS. 7A-7E, 8C, and 8D.

FIGS. 7A-7E are graphs showing the differences in regulatory T cell expansion (FIG. 7A), IL-2 secretion (FIG. 7B), or T cell division (FIGS. 7C, 7D, and 7E) when DC are incubated with a mix of nanoparticles (NP) containing either antigen ovalbumin (OVA) or rapamycin (RAPA) (Mix), or with NP containing both OVA and RAPA in the same NP (Co). FIG. 7A shows percent expansion of CD4+CD25+FoxP3+ regulatory T cells in the presence of soluble OVA+RAPA in solution, or Mix, or Co, over incubation time (h). FIG. 7B is a graph showing secretion of mouse IL-2 (mIL-2) by CD4 OT-II T cells over time (h) when the cells are incubated with OVA NP, Mix, or Co. FIGS. 7C and 7D show the cell division plots for CD4 OT-II T cells incubated with Mix or Co over incubation time (h), and FIG. 7D is a graph of the percent divided (% Divided) CD4 OT-II T cells from FIGS. 7C and 7D. FIGS. 7A-7E demonstrate one of the spatial aspects of directing the immune response with STP.

FIGS. 8C and 8D are graphs showing the percent (%) Total Release of Rapamycin (FIG. 8C) and Ovalbumin (FIG. 8D) from PLGA NP containing the antigen OVA and RAPA (1), or STP containing OVA in the core particle and RAPA in the tethered particle (2).

The spatiotemporal configuration of RAPA and antigen was as follows: (1) the preferred sequential release of RAPA (early) and antigen (late); (2) the co-spatial distribution of RAPA and antigen in a single particle (FIGS. 8A and 8B). To ensure normalization of RAPA and antigen loading, RAPA-CD added to STP was equivalent to the amount of RAPA loaded in antigen/RAPA co-loaded nanoparticles (OVA/RAPA). The nanoparticles, including STP, were similar in size, zeta potential, loading, and shape to each other (Table 4). STP released RAPA faster than OVA/RAPA nanoparticles, which contain both OVA and RAPA encapsulated in the core of the PLGA nanoparticles (FIGS. 8C and 8D). The release rate of OVA in STP and OVA/RAPA was the same (FIG. 8D), showing that STP fully satisfied the favorable spatiotemporal condition through earlier release of RAPA from a single particle.

Figure 8E:
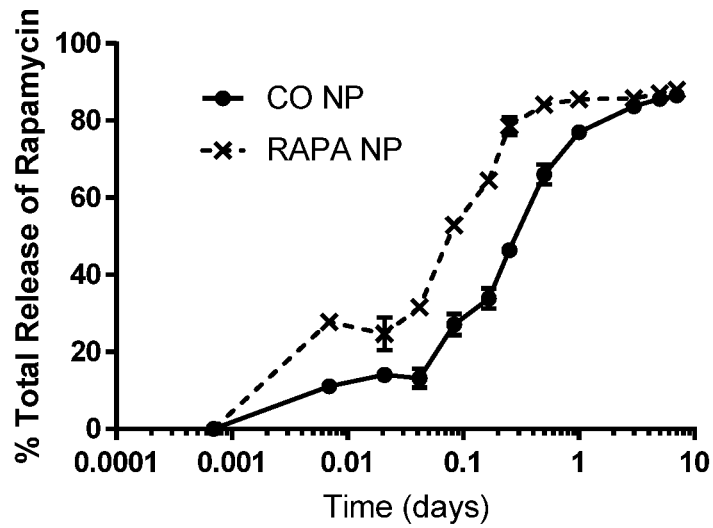
FIGS. 8E and 8F are graphs showing the percent (%) cumulative rapamycin release (FIG. 8E) or percent (%) cumulative OVA release (FIG. 8F) over time (days) from co-encapsulating particles (Co NP) or OVA or RAPA particles. The particles were incubated in PBS at 37° C., and supernatant was collected to measure the level of RAPA (top) and OVA (bottom) at each timepoint (N=3; p-values calculated by student t-test for each timepoint).
Figure 8F:
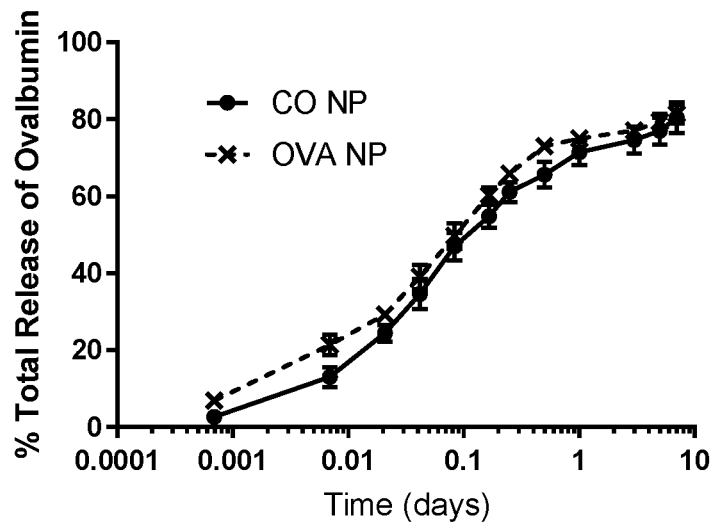

The release rate of RAPA and OVA being different in single veresus. co-encapsulated particles due to steric hindrance caused when two agents are both released from the core of the particle was investigated. No discernable difference of RAPA and OVA release between single-encapsulated RAPA or OVA particles and co-loaded OVA/RAPA particles was detected (FIGS. 8E and 8F).

TABLE 4

Size, zeta potential, loading of the nanoparticles and STP.

| | Blank | OVA | OVA/RAPA | STP |
|---|---|---|---|---|
| Size | 217.4 ± 7.86 | 245.4 ± 1.45 | 206.03 ± 3.13 | 271.3 ± 4.99 |
| Zeta Potential | −26.76 ± 5.99 | −22.43 ± 5.45 | −22.13 ± 5.39 | −17.93 ± 3.82 |
| Antigen Loading (µg/mg NP) | 0 | 28.76 | 22.47 | 28.76 |
| RAPA Loading (µg/mg NP) | 0 | 0 | 8.69 | 8.69 |

Example 3. STP (OVA-RAPA) Suppress IFN-Gamma Producing Cells in Vitro

Materials and Methods

PLGA particles without agent (blank NP), with OVA only (OVA NP), with OVA and RAPA incorporated in the same PLGA particles (OVA/RAPA NP), and STP containing OVA in the core particle and RAPA in the tethered particle, were generated as described in Examples 1 and 2. PLGA particles containing TGF-beta and IL-2 in the same particle were generated by a similar method.

Results

Figure 9A:
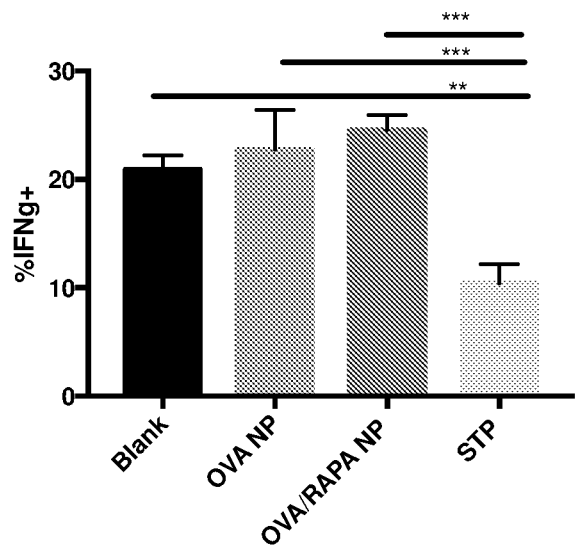
FIGS. 9A and 9B are graphs showing percent IFN-gamma producing (% IFN-g$^+$) CD4+ T cells in vitro when the cells are incubated with Blank NP (PLGA NP only), OVA NP (PLGA NP containing OVA), OVA/RAPA NP (PLGA NP containing OVA and RAPA in the same NP), or STP (containing OVA in the core particle and RAPA in the tethered particle) alone (FIG. 9A), or in the presence of PLGA NP containing TGF-beta and IL-2 in the same NP (TI) (FIG. 9B). Splenocytes from OT-II mice were collected and treated with particles for 3 days. (N=3).
Figure 9B:
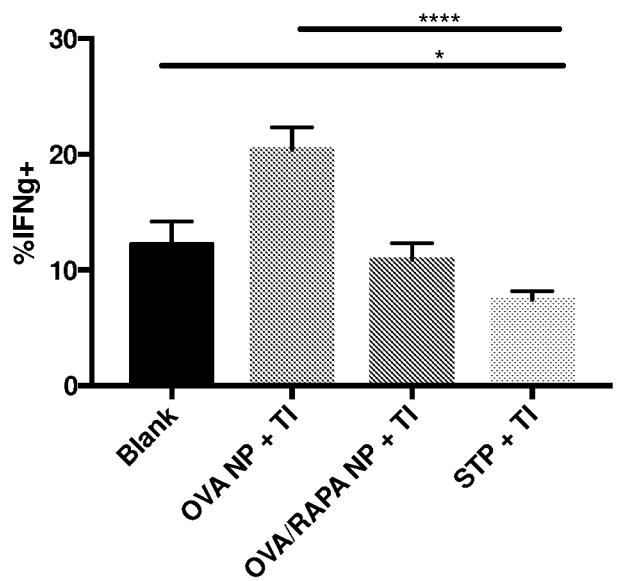

The results are presented in FIGS. 9A and 9B.

FIGS. 9A and 9B are graphs showing percent IFN-gamma producing (% IFN-g$^+$) CD4+ T cells in vitro when the cells are incubated with Blank NP (PLGA NP only), OVA NP (PLGA NP containing OVA), OVA/RAPA NP (PLGA NP containing OVA and RAPA in the same NP), or STP (containing OVA in the core particle and RAPA in the tethered particle) alone (FIG. 9A), or in the presence of PLGA NP containing TGF-beta and IL-2 in the same NP (FIG. 9B).

The tolerogenic effect of STP in vitro was investigated. OT-II splenocytes treated with STP for three days had the highest percentage of Tregs, but the lowest population of IFNg producing cells (FIGS. 9A and 9C), showing that delivery of RAPA and antigen in an effective spatiotemporal configuration can enhance induction of tolerance. Previous literatures implied that induced Tregs are generally polyclonal and not antigen-specific (Adair et al., *Front Immunol*, 8:1117 (2017)), suggesting that STP-generated Tregs in vitro are not antigen-specific. To address the possibility of STP favoring expansion of polyclonal Tregs, the T cell receptor (TCR) of Tregs was investigated. The proportion of Vα2+ Vβ5+ T cells was similar in STP-induced Tregs compared to Tregs in OT-II, showing that STP-induced development of Tregs was not biased exclusively to polyclonal Tregs and also can establish antigen-specific tolerance (FIG. 9D).

Example 4. STP (OVA-RAPA) Enhance Treg Development In Vitro

Materials and Methods

Methods for Studies in Examples 4-9

Mice. All mice were bred at Yale University in accordance with the guidelines of the Institutional Animal Care and Use Committee (IACUC). The following mice breeding pairs of were purchased from Jackson Laboratory: C57BL/6J, CD45.1, OT-II, RAG1$^{-/-}$, and TCR$^{MOG}$. Foxp3 fate mapping mice were generated. All mice were genotyped by suggested primers on Jackson Laboratory. Females of 8-14 weeks of age were used in all experimental procedures unless otherwise stated.

Isolation of cells from harvested animal tissues. Spleens and lymph nodes were dissociated and filtered through a 40-µm strainer. Large intestines (LI) were isolated by incisions, manually inverted to expose the inner lumen and the lamina propia, and washed with DTT and EDTA for 15 mins in 37° C. Supernatant was separated for analysis of intestinal epithelial cells. LIs were then digested by Collagenase Type II (Gibco) and Dispase (Gibco) for 45 mins in 37° C. Digested LIs were filtered through 100-µm and 40-µm strainer, and then stained by antibodies for analysis by flow cytometry. For isolation of the central nervous system (CNS), brain and spinal cord was isolated from mice. Harvested CNS were passed through 40-µm strainer and lymphocytes/neutrophils were collected by Percoll gradient (Sigma). Isolated cells were stained by antibodies and analyzed by flow cytometry.

Flow cytometry and sorting. Harvested cells were spun down and washed with flow cytometry buffer (2% FBS in PBS). Fc receptors of cells were blocked with Fc block (Biolegends) at 1:500 dilution on ice for 10 minutes. After washing, cells were incubated on ice for 10 minutes with fluorophore-labelled antibodies for staining of cell surface markers. All cell surface markers were stained at 1:200 dilution in flow cytometry buffer. Intracellular staining was performed by fixation and permeabilization of cells with the eBioscience Foxp3/Transcription Factor Staining kit at a 1:100 dilution. The following antibodies from BioLegends were used: CD45.1, CD45.2, CD45RB, CD4, TCRβ, NK1.1, ST2, CD103, Valpha2, Vbeta5, CD71, CD44, CD11c, CD11b, F4/80, Ly6G, CD8a, CD205, CD206, IFNg, IL-17A, Helios, Foxp3, RORgt, GATA3, GM-CSF. Stained cells were analyzed on LSRII flow cytometer (BD Biosciences, San Jose, Calif.) and FlowJo software (Tree Star, Ashland, Oreg.). Cell sorting was performed on Aria II cytometer (BD Biosciences) after staining cells with the abovementioned antibodies.

DC and T Cell culture in vitro. Harvested primary splenocytes were cultured in complete medium, which was made in RPMI (Gibco) with 10% FBS (Gibco), 2% Penicillin/Streptomycin (Thermo Fisher Scientific), 1×MEM Non-Essential Amino Acid Solution (Gibco) and 1× pyruvate (Gibco). For co-culture in vitro experiments, isolated DCs were pulsed with indicated nanoparticles for overnight. Nanoparticles were washed off by centrifugation, and DCs were cultured with T cells at 1:5 ratio. TGF-β/IL-2 nanoparticles were added to the co-culture at 100 μg/ml. After 72 hours, cells were washed and prepared for analysis by flow cytometry.

Statistical analysis. Statistical significance was determined by performing unpaired t-test, provided by Prism 7 (Graphpad; La Jolla, Calif.). β-values less than 0.05 were determined significant.

PLGA particles without agent (blank NP), with OVA only (OVA NP), with OVA and RAPA incorporated in the same PLGA particles (OVA/RAPA NP), and STP containing OVA in the core particle and RAPA in the tethered particle, were generated as described in Example 1. PLGA particles containing TGF-beta and IL-2 (TGFb/IL2 NP) in the same particle were generated by a similar method.

The BMDCs pulsed with particles, activated with LPS for 4 hours, washed, co-cultured with OT-II cells. The co-culture was incubated with Blank NP (PLGA NP only), OVA NP (PLGA NP containing OVA), OVA/RAPA NP (PLGA NP containing OVA and RAPA in the same NP), or STP (containing OVA in the core particle and RAPA in the tethered particle) in the presence of PLGA NP containing TGF-beta and IL-2 in the same NP.

The cells were then analyzed by flow cytometry gating on CD4+CD44+CD69+OT-II cells and detecting CD25+ and Foxp3+ cells.

Results

Figure 9C:
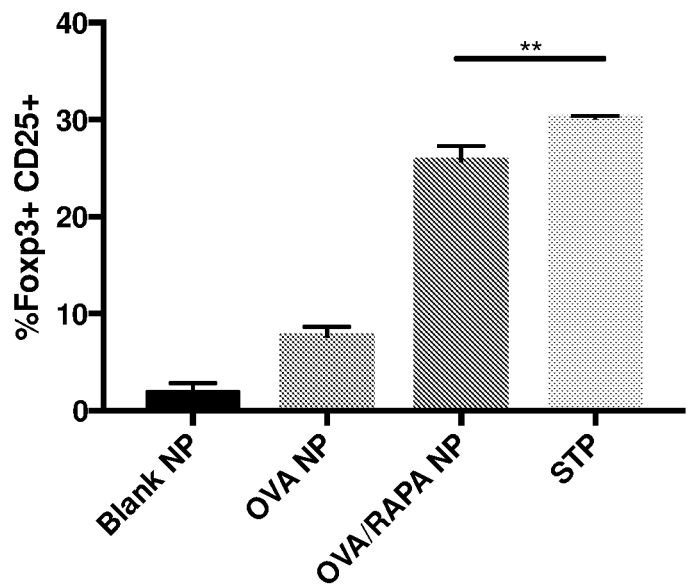
FIG. 9C is a graph showing percent Foxp3 and CD25 expressing cells (gated on CD4 T cells). OT-II splenocytes were harvested and treated with particles, in addition to TGFb (10 ng/ml) and IL-2 (5,000 IU/ml) for 3 days (N=3; p-values were calculated by student t-test).
Figure 9D:
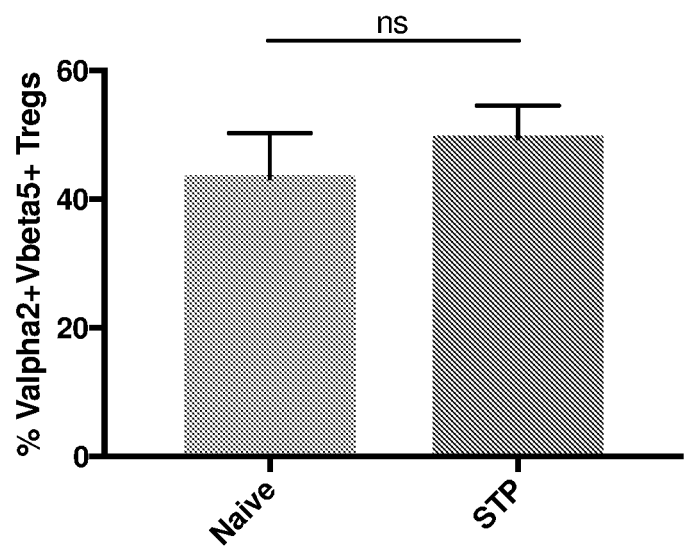
FIG. 9D is a graph showing the percentage of Valpha2 and Vbeta5 TCR expressing cells (gated on CD4+ Tregs). Valpha2 and Vbeta5 TCR positive cells are TCR-specific to OVA, showing that proportion of antigen-specific Tregs has not changed by STP and that Treg expansion is not skewed towards polyclonal Tregs.

The results are presented in FIG. 9C. The percent increase in CD25+Foxp3+T reg cells is shown.

Example 5. STP (OVA-RAPA) Enhance Treg Population In Vivo

Materials and Methods

At day 0, C57BL6/J mice were injected four times with either PLGA NP containing OVA and RAPA in the same particle (OVA/RAPA), or STP (containing OVA in the core particle and RAPA in the tethered particle) at 2 mg.

On day 7, the mice were sacrificed, spleens extracted, and splenocytes co-cultured with naive CD+OT-II cells in the presence of 10 μg OVA and PLGA NP containing TGF-beta/IL-2/Butyrate in the same NP. On day 10, the cells were harvested and analyzed by FACS for the percent of Foxp3+ cells (% Foxp3+) among the CD4+OT-II T cells.

On day 7, the isolated cells were splenocytes incubated with mitomycin C (25 ug/ml), co-cultured with CFSE-stained with CD4 OT-II in 10 μg/ml OVA peptide media, with or without TI.

Results

Figure 11A:
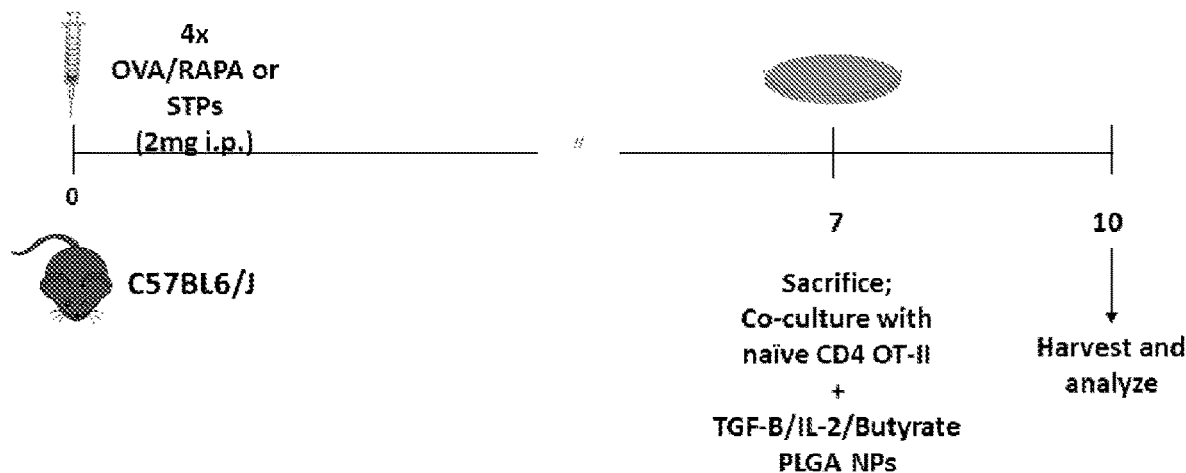
FIG. 11A is a diagram showing the experimental setup used to obtain the data in FIG. 11B. Mice were injected daily with nanoparticles for four days. Treatment was with blank NP (PLGA NP only), OVA NP (PLGA NP containing OVA), OVA/RAPA NP (PLGA NP containing OVA and RAPA in the same NP), or STP (containing OVA in the core particle and RAPA in the tethered particle) Splenocytes were harvested on day 7 and treated with mitomycin C (10 µg/ml). They were then co-cultured with purified CD4 T cells from OT-II mice for three days in the presence of TI NPs (N=4), after which they were analyzed by flow cytometry for Foxp3 expression.
Figure 11B:
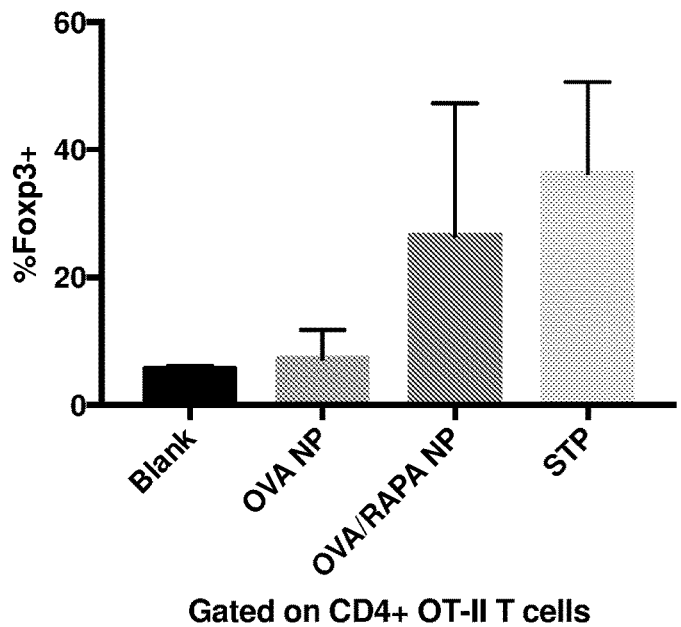

The results from the FACS analysis are shown in FIG. 11B.

Figure 12A:
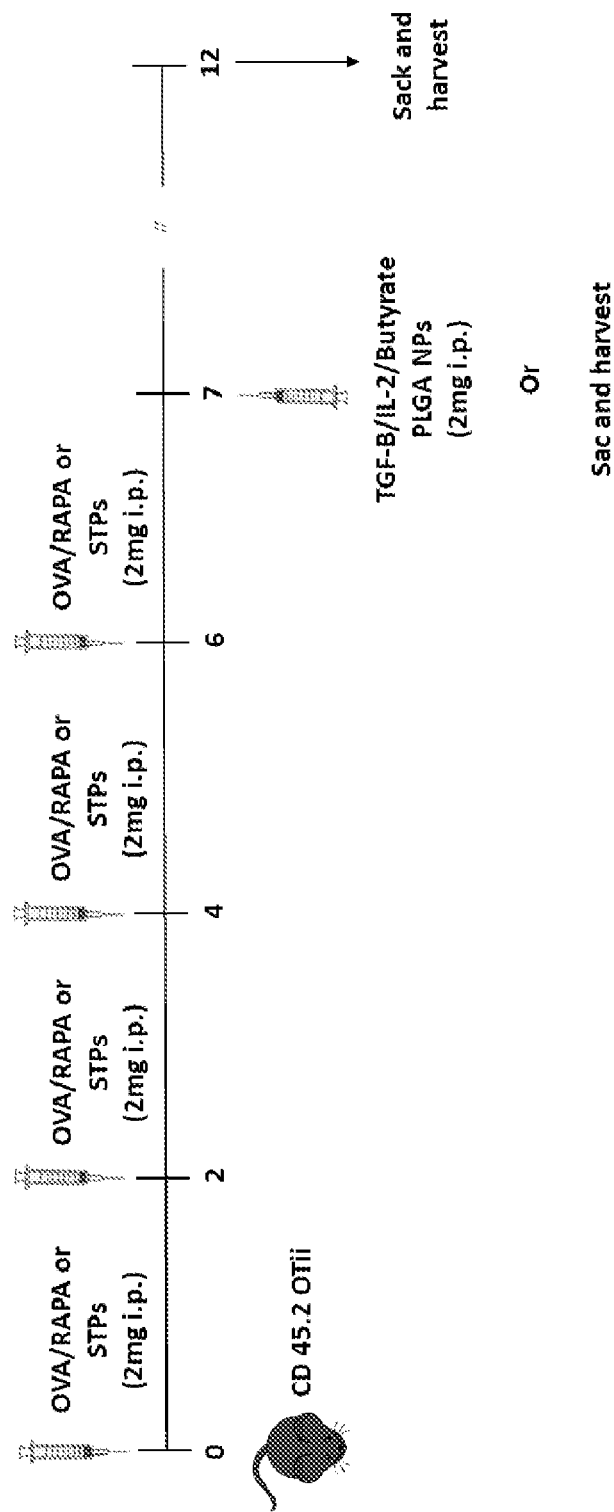
FIG. 12A is a diagram showing the experimental setup used to obtain the data in FIGS. 12B-12G.
Figure 12B:
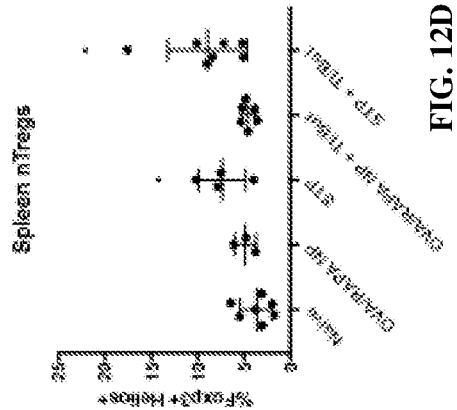
FIGS. 12B-12G are graphs showing the systemic expansion of Tregs in response to STPs in steady state in the spleen (FIGS. 12B-12D) and in the mesenteric lymph nodes (mLN) (FIGS. 12E-12G). The change in total Tregs as a change in percent Foxp3+ cells in the spleen (FIG. 12B) and mLN (FIG. 12E), the change in induced Tregs (iTregs) as a change in percent Foxp3+Helios– cells in the spleen (FIG. 12C) and mLN (FIG. 12F), and the change in natural Tregs (nTregs) as a change in percent Foxp3+Helios+ cells in the spleen (FIG. 12D) and mLN (FIG. 12G), with the different treatments are shown. No change in other T cell subsets and innate cells, specifically in neutrophils, natural killer (NK) cells, GATA3+ cells, and RORgt+ cells in the spleen or mLN was detected.
Figure 12C:
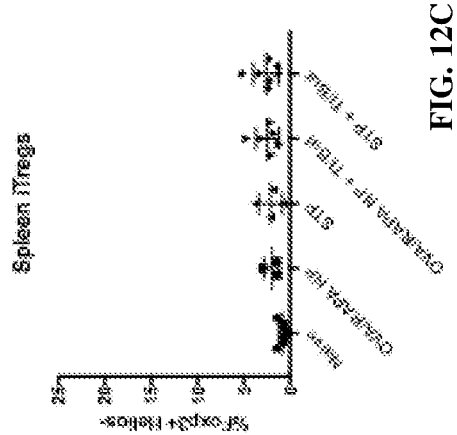
Figure 12D:
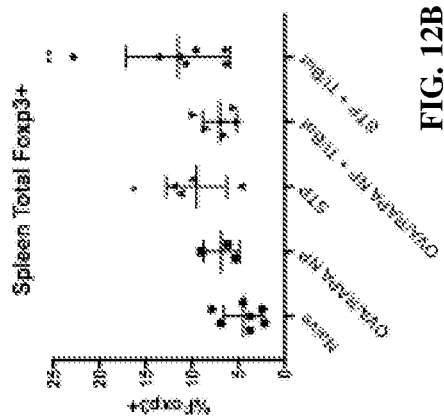

Example 6. Systemic Expansion of CD4+nTreg Population In Vivo in Response to STP in Steady State Materials and Methods FIG. 12A is a diagram showing the experimental setup used to obtain the data in FIGS. 12B-12G. At days 0, 2, 4, and 6 CD45.2 OT-II mice were injected i,p, with either PLGA NP containing OVA and RAPA in the same particle (OVA/RAPA), or STP (containing OVA in the core particle and RAPA in the tethered particle) at 2 mg. On day 7, some of the mice were injected with PLGA NP containing TGF-beta/IL-2/Butyrate in the same NP (at 2 mg intraperitonealy (i.p.)), others were sacrificed and the spleens and lymph nodes were harvested for further analyses. On day 12, the remaining mice were sacrificed and the spleens and lymph nodes were harvested for further analyses.

Results

Figure 12E:
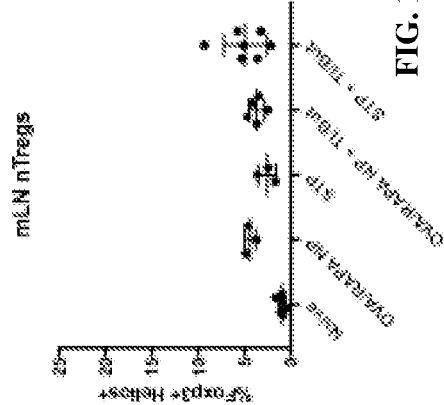
Figure 12F:
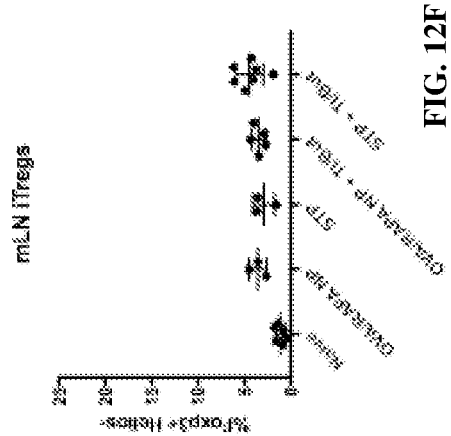
Figure 12G:
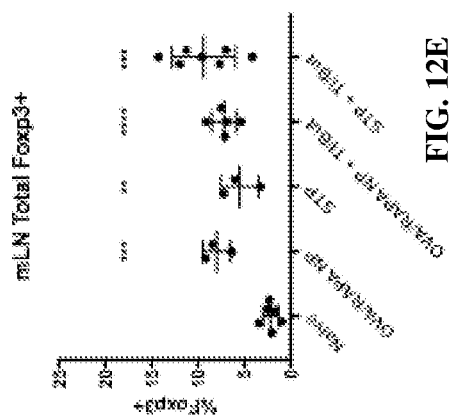

FIGS. 12B-12G demonstrate the systemic expansion of CD4+ nTregs in response to STOs in steady state in the spleen (FIGS. 12B-12D) and in the mesenteric lymph nodes (mLN) (FIGS. 12E-12G). The change in total Tregs as a change in percent Foxp3+ cells in the spleen (FIG. 12B) and mLN (FIG. 12E), the change in induced Tregs (iTregs) as a change in percent Foxp3+Helios− cells in the spleen (FIG. 12C) and mLN (FIG. 12F), and the change in natural Tregs (nTregs) as a change in percent Foxp3+Helios+ cells in the spleen (FIG. 12D) and mLN (FIG. 12G), with the different treatments are shown. No change in other T cell subsets and innate cells, specifically in neutrophils, natural killer (NK) cells, GATA3+ cells, and RORgt+ cells in the spleen or mLN, was detected.

Figure 14A:
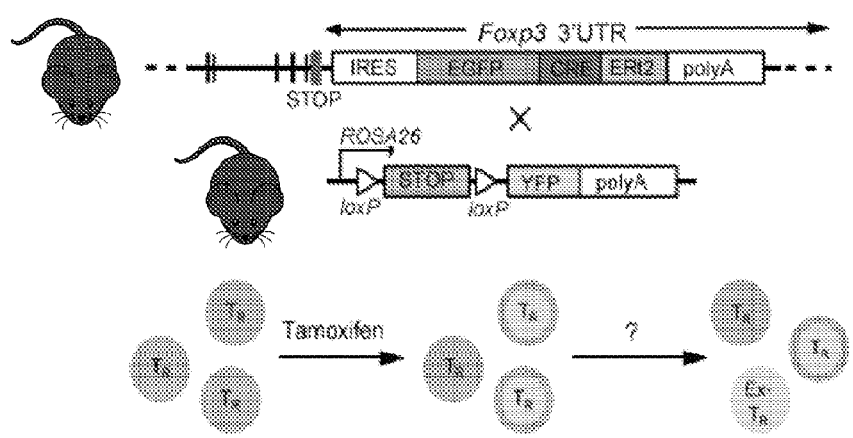
FIG. 14A is a diagram showing the Foxp3 3' UTR locus arrangement of genetically modified mice (details provided in Rubstov et al., Science, 329(5999):1667-1671 (2010)) used in the experimental setup shown in FIG. 14B. A mouse with a triple-transgene cassette (EGFP, CRE, and Ert2) harbored in Foxp3 locus is crossed with another mouse with stop codon flanked by loxP sites upstream of YFP in ROSA26 locus. Progenies are crossed to F2 generation and genotyped homozygous mutants are selected. Upon tamoxifen administration, Tregs (GFP+) express YFP, marking them as pre-existing nTregs in the spleen.

Example 7. Expansion of nTreg Population In Vivo, Instead of Increased Output of Thymic Tregs, in Response to STP Materials and Methods FIG. 14A is a diagram of genetically modified mouse (details provided in Rubstov et al., Science, 329(5999): 1667-1671 (2010)) used in the experimental setup shown in FIG. 14B.

Figure 14B:
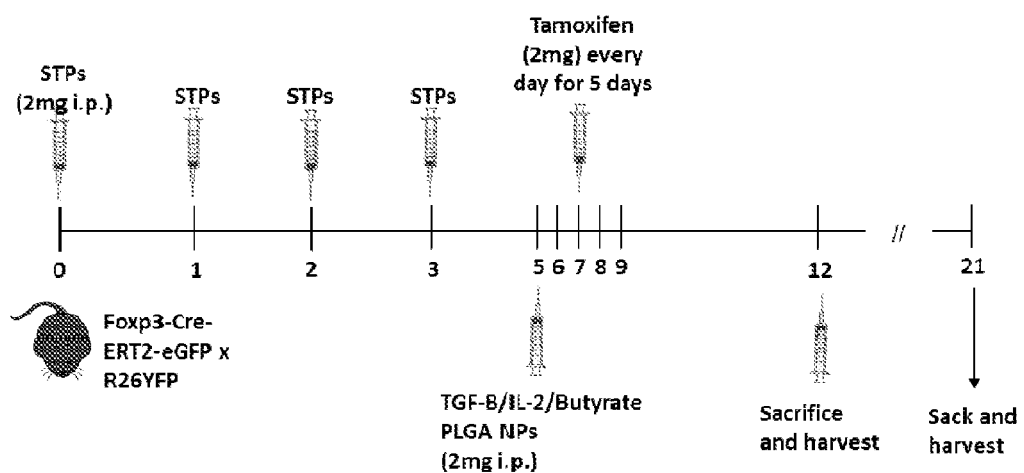
FIG. 14B shows the experimental setup for determining the source of the systemic expansion of nTregs.

FIG. 14B shows the experimental setup for determining whether systemic expansion of nTregs is due to nTreg expansion or to the increased output of thymic Tregs. Foxp3-Cre-ERT2-eGFPxR26YFP mice were injected i.p. at days 0, 1, 2, and 3 with STP (containing OVA in the core particle and RAPA in the tethered particle) at 2 mg. On day 5, some of the mice were injected with PLGA NP containing TGF-beta/IL-2/Butyrate in the same NP (at 2 mg i.p.). On days 5, 6, 7, 8, and 9 the mice received tamoxifen (2 mg) every day, for 5 days. On day 12, some of the mice were sacrificed and the spleens harvested for further analyses. On day 21, the remaining mice were sacrificed and the spleens harvested for further analyses.

Nanoparticle administration and cellular adoptive transfer in mice. All prepared nanoparticles prepared fresh in sterile PBS at 10 mg/ml. Unless indicated otherwise, each mouse received an intraperitoneal injection of 2 mg of particles. Adoptive transfer of cells into RAG$^{-/-}$ mice was done by intravenous injection of $5.0 \times 10^5$ OT-II CD4 T cells or $5.0 \times 10^5$ WT naïve CD4 T cells.

Results

Figure 14C:
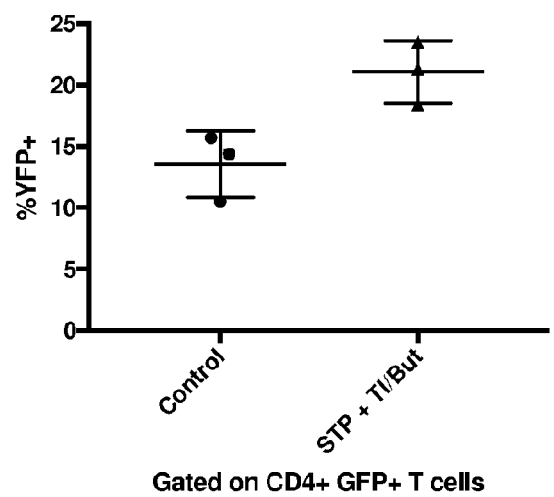
FIGS. 14C, 14D, and 14E are graphs showing the change in Treg population with the different treatments shown in FIG. 14B.
Figure 14D:
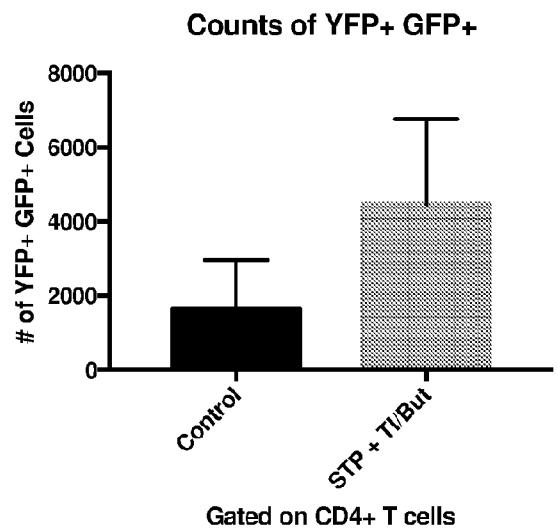
Figure 14E:
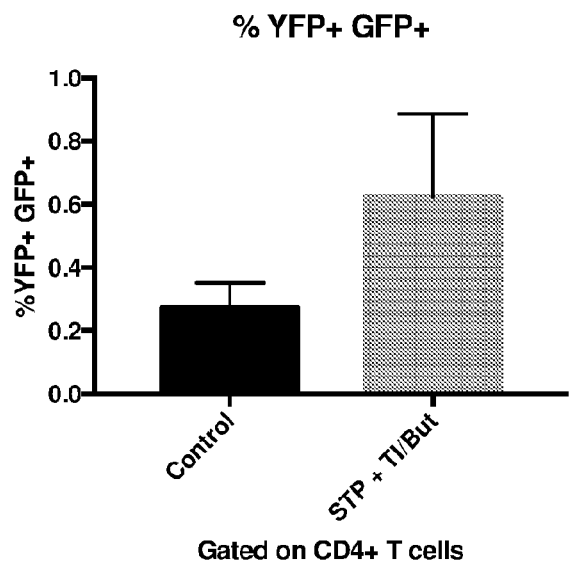

FIG. 14C shows the percent change in YFP+ cells from the CD4+ GFP+ T cells when the animals (genotype shown in FIG. 14A) received control or STP with TGF-beta/IL-2/Butyrate in the same NP (as shown in FIG. 14B), p=0.0248. FIG. 14D shows the change in the number (#) of YFP+ GFP+CD4+ T cells when the animals (genotype shown in FIG. 14A) received control or STP with TGF-beta/EL-2/Butyrate in the same NP (as shown in FIG. 14B), p=0.1365. FIG. 14E shows the change in the percent (%) of YFP+ GFP+CD4+ T cells when the animals (genotype shown in FIG. 14A) received control or STP with TGF-beta/IL-2/Butyrate in the same NP (as shown in FIG. 14B), p=0.0914. More of the YFP+ cells were observed in the GFP+ population, showing that expansion of Tregs is from preexisting nTregs.

Figure 10A:
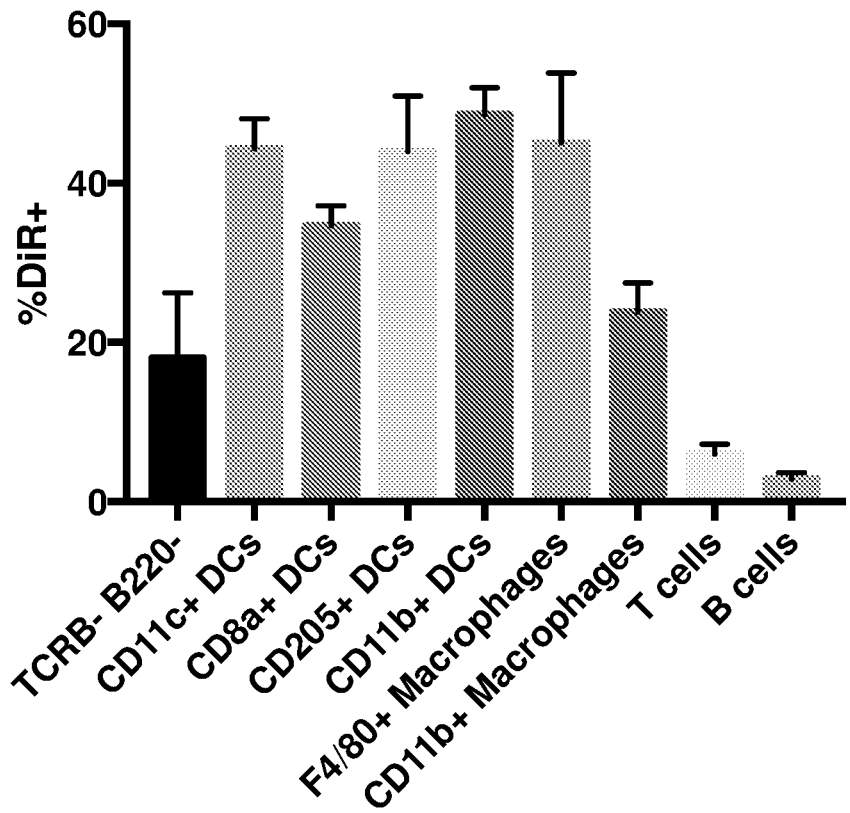
FIG. 10A is a bar graph showing percent (%) DiR positive cells—cellular distribution of splenocytes that take up DiR+ nanoparticles in vivo. DiR+ nanoparticles were injected, and splenocytes were harvested one day after and percentages of cell subsets uptaking DiR nanoparticles are obtained by FACS (N=3).
Figure 10B:
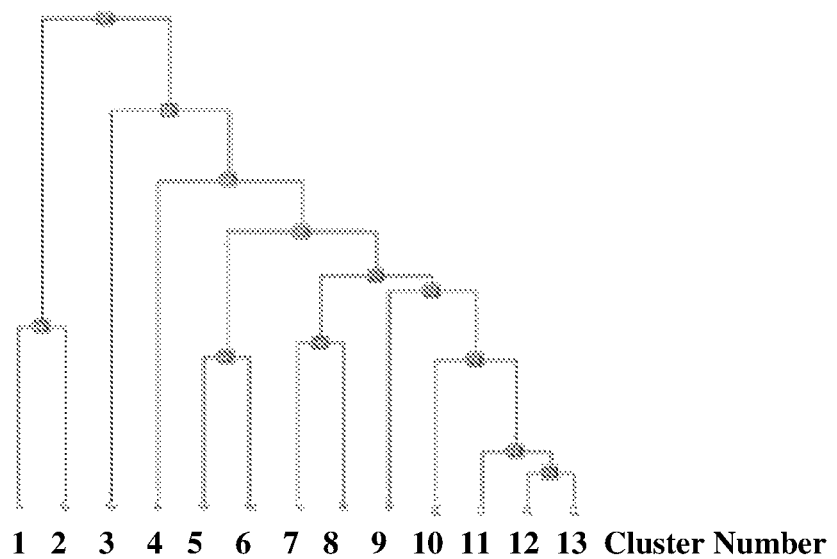
FIG. 10B is a phylogenic tree denoting cell population lineage of each clusters, demonstrating that the clusters can be more loosely grouped according to their transcriptome.
Figure 12H:
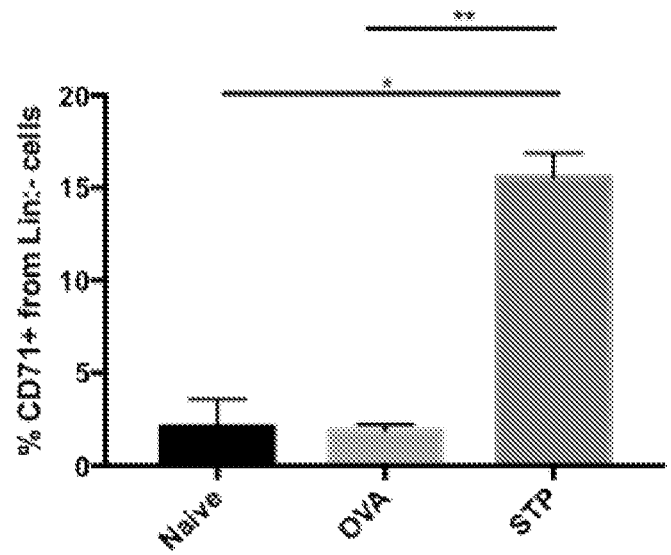
FIG. 12H is a bar graph showing percent (%) CD71+ cells, gated on Lin:– (TCRb–, B220–) (N>3; p-values were determined by student t-test).
Figure 12I:
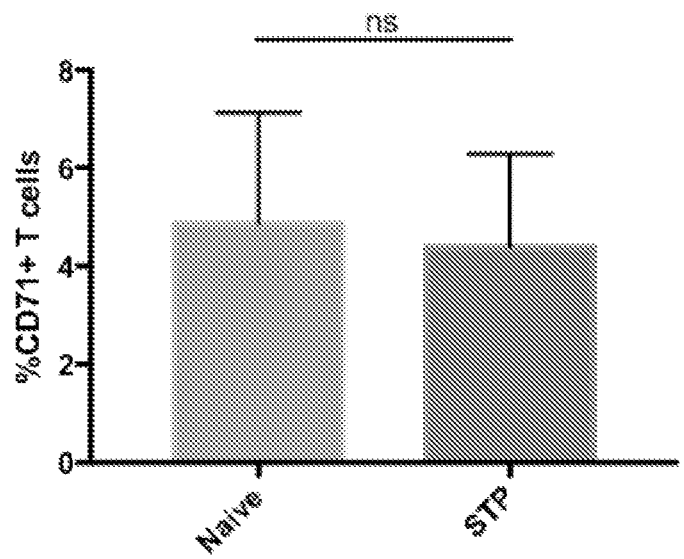
FIG. 12I is a bar graph showing percent (%) CD71+ cells, gated on T cells (N>4; p-values were determined by student t-test). For FIGS. 12H and 12I, the OT-II mice were injected with particles, and splenocytes were harvested and analyzed by FACS.
Figure 13A:
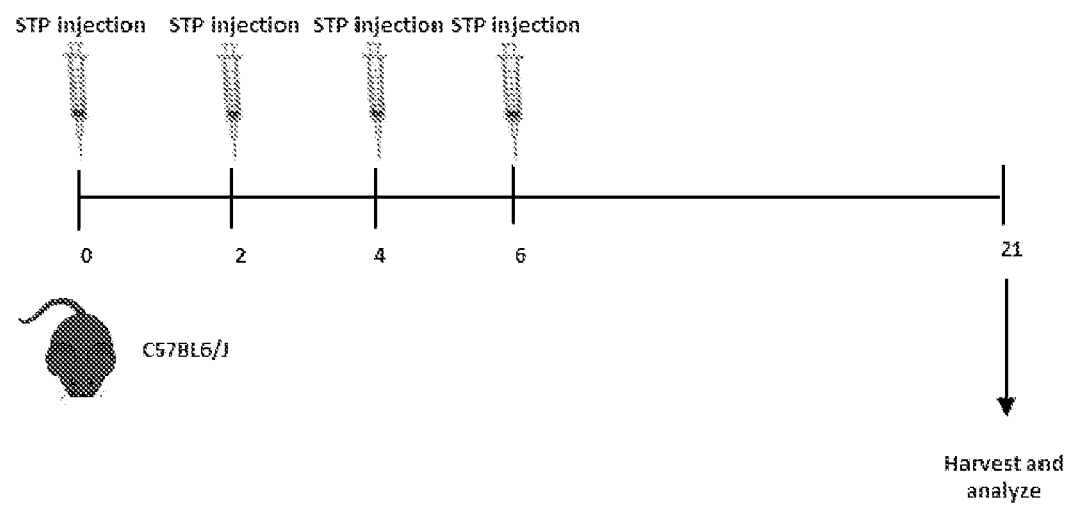
FIG. 13A is a diagram showing the particle injection scheme for STP-induced tolerance in vivo, and representative FACS plots for Helios and Foxp3 expressing cells (gated on CD4 T cells) were analyzed and the results are shown in FIGS. 13B-13G by percentage and in FIG. 13H by counts of (N>3; data was pooled from three or more independent experiments).
Figures 13B, 13C, 13D, 13E, 13F, 13G:
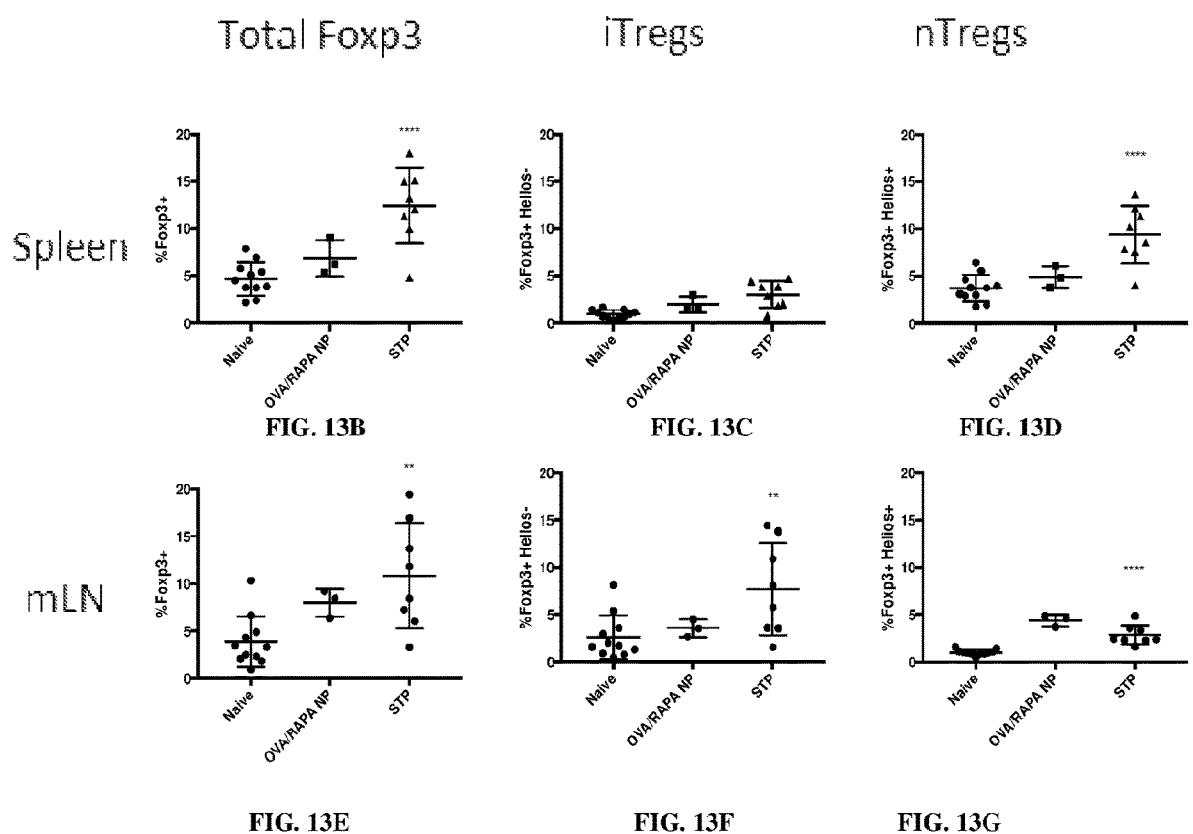
Figure 13H:
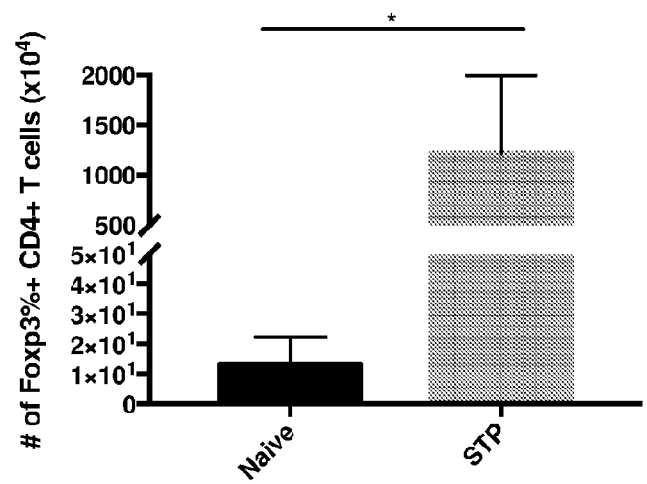

Specifically, STPs were tested for inducing immune tolerance in vivo. As STP and OVA/RAPA deliver RAPA to cells that uptake nanoparticles, inhibition of PI3K-Akt-mTOR pathway by RAPA was tested. It is well-known that RAPA binds to FKBP12 to form a complex that inhibits mTORC1 function, and one of many readouts for proper mTOR inhibition is upregulation of transferrin receptor, CD71. Mice injected with STP indeed demonstrated significantly higher proportion of B220$^-$TCRb$^-$ cells that were CD71 positive, confirming mTOR inhibition by RAPA delivery (FIG. 12H). Interestingly, this effect was not seen in CD4 T cells, showing that there is no systemic shut-down of mTOR by RAPA in CD4 T cells and that RAPA delivery is limited to cells that uptake nanoparticles (FIG. 10A). The results show that there is no systemic leakage of RAPA of STP in vivo, and that RAPA delivery by STP is highly selective to B220$^-$TCRb$^-$ cells.

Splenocytes harvested from STP-injected mice were most potent in generating OT-II Tregs ex vivo (FIG. 11B), showing that STP cellular uptake in vivo induced tolerance and that it was superior to OVA alone nanoparticles. An enhanced Treg expansion in STP compared to OVA/RAPA co-encapsulated nanoparticles was observed (data not shown). STP also significantly increased the proportion of systemic Tregs in the spleen and the mLN (FIGS. 13A and 13B-13G) in vivo, asserting its superiority over co-encapsulated nanoparticles.

Tregs in vivo can be classified into nTregs and iTregs. Several markers have been suggested to differentiate between nTregs and iTregs, but the most canonical marker has been the transcription factor, Helios, which is an Ikaros transcription factor family member. It was found that the increased proportion of Tregs in the spleen in vivo was largely due to the increase in nTregs, not iTregs (FIGS. 13A and 13B-13G). In the mesenteric lymph node (mLN), an increase for both nTregs and iTregs was observed (FIGS. 13A and 13B-13G). While iTregs are infamous for their plasticity and tendency to revert back to inflammatory T cells, such as Th17, nTregs are known to be more resilient to the inflammatory cues and have been shown to retain their fate, largely owing to their epigenetic state. As such, STP's ability to systemically expand nTregs was a highly effective measure to establish stable tolerance in vivo.

Figures 18A, 18B, 18C, 18D:
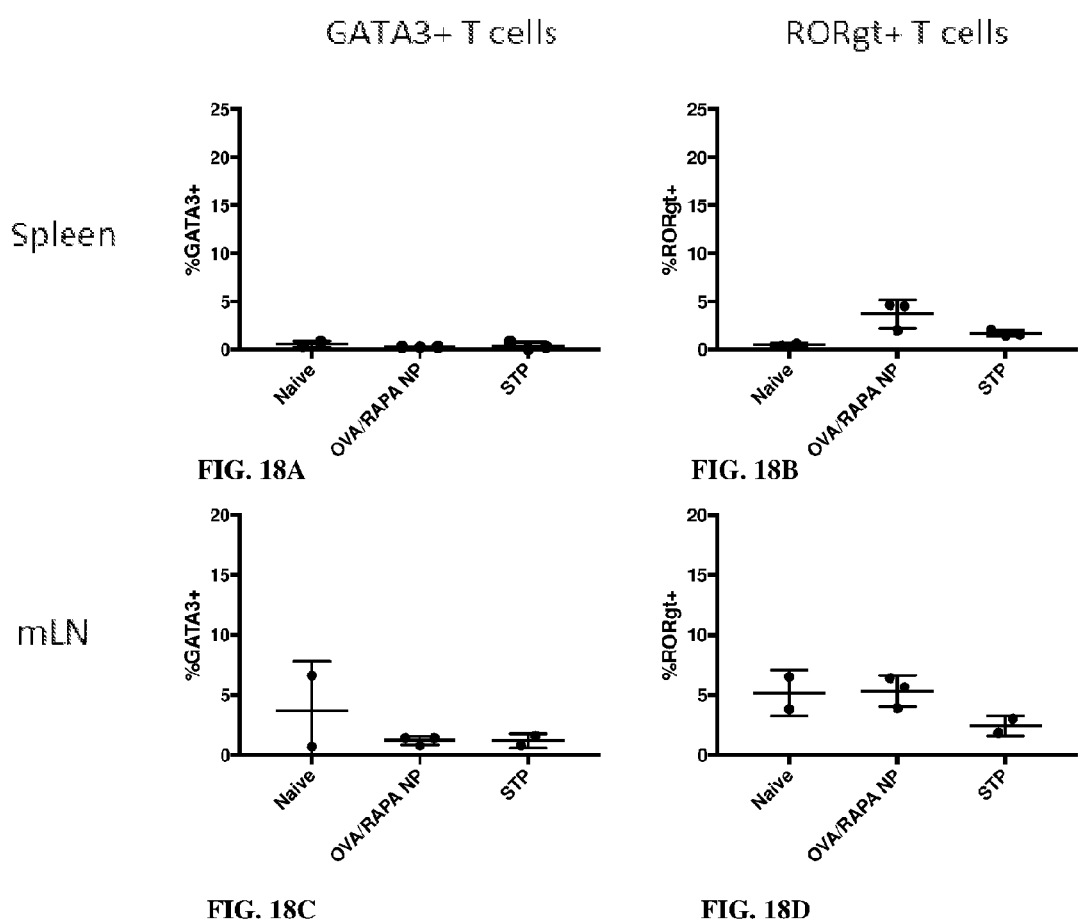
FIGS. 18A-18D are graphs showing percent population of cells from spleen (FIGS. 18A and 18B) and mesenteric lymph nodes (FIGS. 18C and 18D) that are GATA3+ and RORgt+(gated from CD4 T cells) (statistical significance was determined by student t-test). OT-II mice were injected with particles for four times every two days, and cells were harvested on day 14 after the initial injection (FIG. 13A).
Figure 20B:
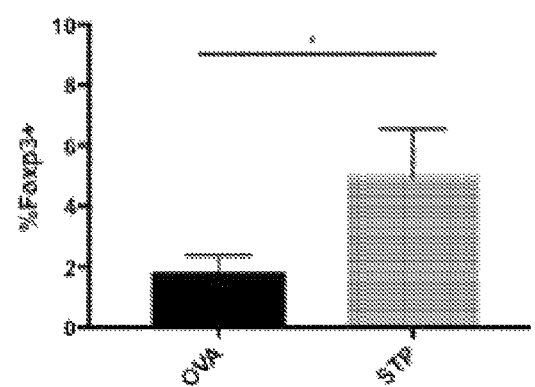
FIG. 20B is a bar graph showing the analysis of representative FACS plots of Foxp3+Helios+ or Foxp3+Helios− splenocytes (gated from CD45.2+CD4+ T cells). Percentage of Foxp3+ cells is shown (N=4; p-values were determined by student t-test).

Some studies have suggested that RAPA-mediated inhibition of mTOR is associated with other CD4 T cell subsets, such as Th2. No significant changes were detected for Th2 cell (GATA3+ T cells, FIGS. 18A and 18C) and Th17 cells (RORgt+ T cells, FIGS. 18B and 18D) in vivo. Slight increase in neutrophils could be detected as a result of STP administration, while proportion of NK cells have significantly decreased (FIGS. 19A-19D). Compared to OVA nanoparticles, STP significantly increased the proportion of Tregs in RAG$^{-/-}$ mice (FIGS. 20A and 20B), suggesting that STP can also expand adoptively transferred CD4 T cells in an immunodeficient environment.

Figure 21:
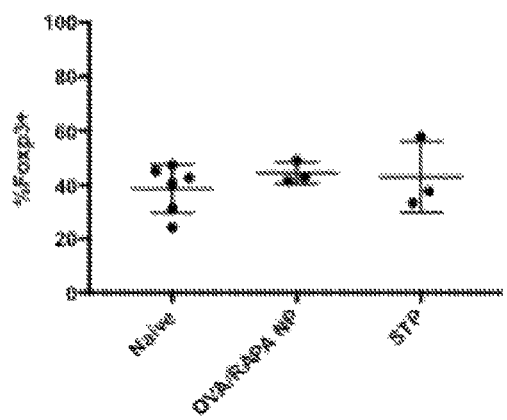
FIG. 21 is a graph showing analysis of FACS data on a population of cells from the lamina propia of large intestine that are Foxp3+Helios+ or Foxp3+Helios− (gated from CD4 T cells) (statistical significance was determined by student t-test). OT-II mice injected with particles as described for FIGS. 18A-18D were sacrificed and harvested cells from the lamina propia were analyzed by FACS. Percentage of Foxp3+ cells is shown.
Figure 22A:
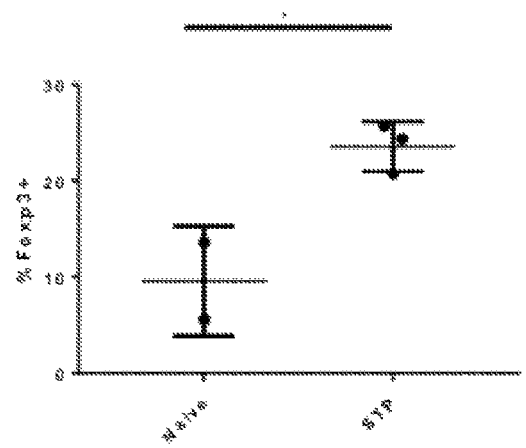
FIG. 22A is a graph showing analysis of FACS plots of Foxp3+Helios+ or Foxp3+Helios− splenocytes from 2D2 mice (MOG$_{35-55}$ TCR specific transgenic mice), gated on CD4 T cells (p-values were determined by student t-test). Percentage of Foxp3+ cells is shown.
Figure 22B:
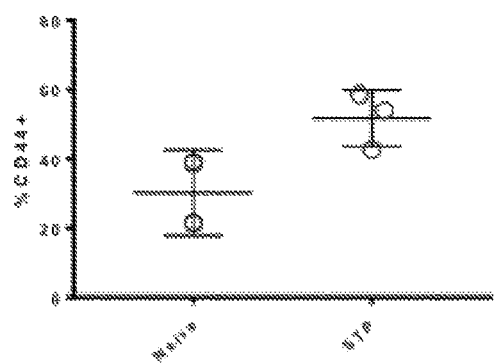
FIGS. 22B-22D are graphs showing CD44+CD4 T cells (FIG. 22B), NK1.1+ cells (FIG. 22C), and RORgt+CD4 T cells (FIG. 22D) from splenocytes of 2D2 mice after injection.
Figure 22C:
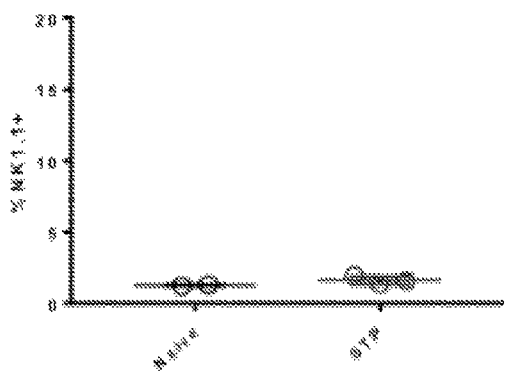
Figure 22D:
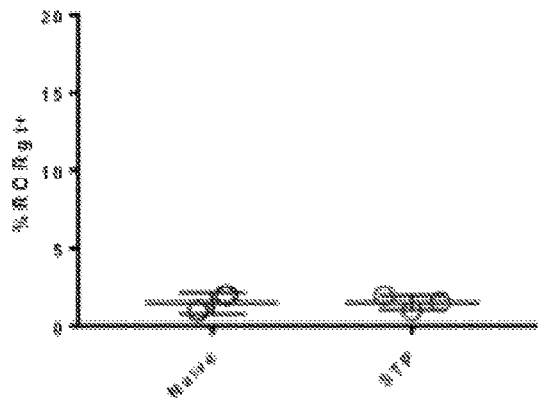
Figure 23A:
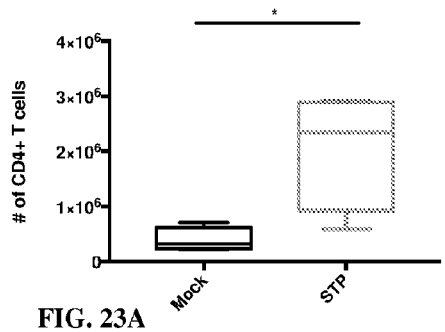
FIGS. 23A-23F are graphs showing the counts of CD4+ T cells, harvested from draining lymph nodes of mice described in FIG. 15B. Draining lymph nodes were harvested and cytokine producing cells were analyzed by FACS through intracellular cytokine staining.
Figure 23B:
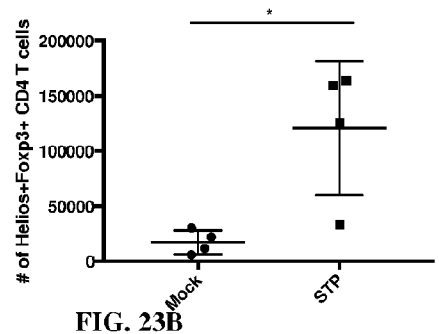
Figure 23C:
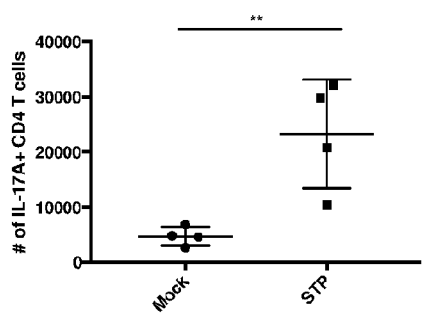
Figure 23D:
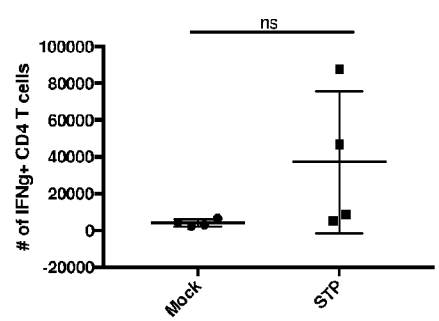
Figure 23E:
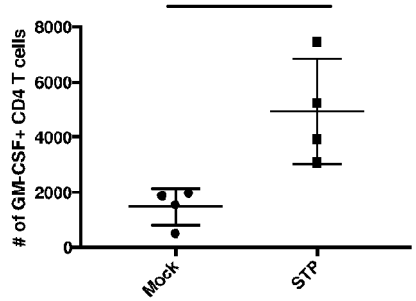
Figure 23F:
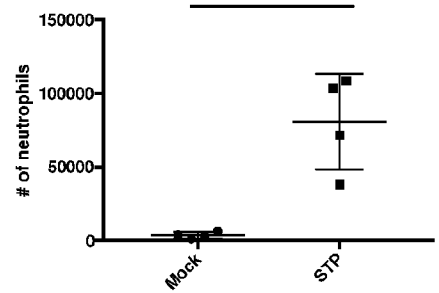
Figure 24A:
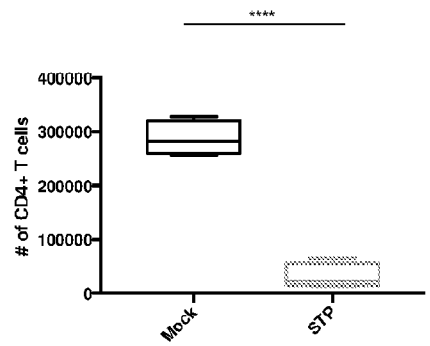
FIGS. 24A-24F are graphs showing counts of inflammatory immune cells and percentages of Tregs from the CNS 14 days post disease induction. Immune cells from brain and spinal cord were isolated from each mice, and were analyzed by FACS.
Figure 24B:
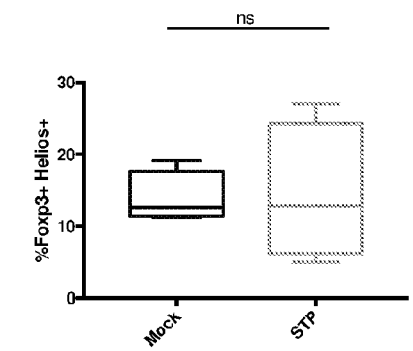
Figure 24C:
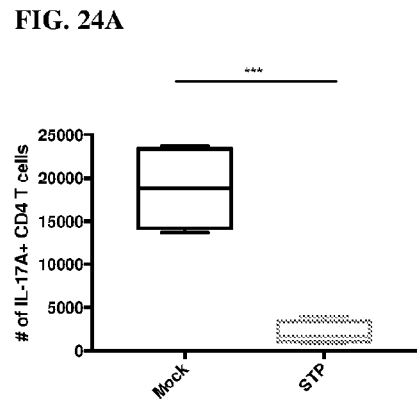
Figure 24D:
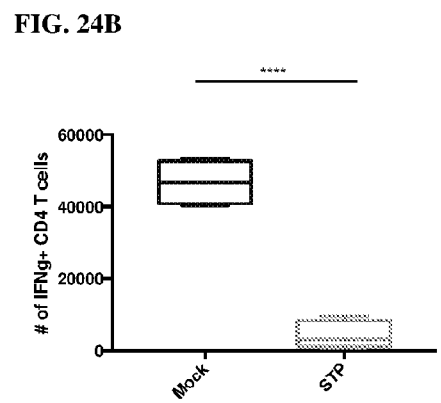
Figure 24E:
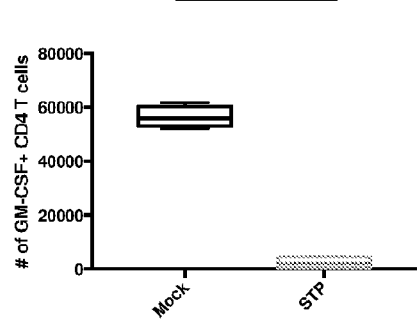
Figure 24F:
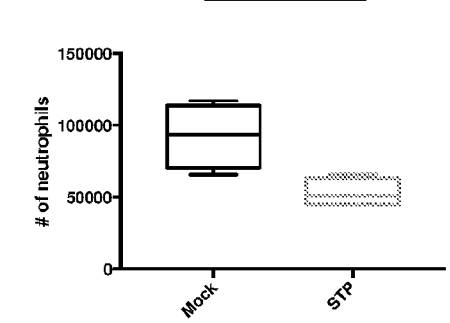
Figure 25A:
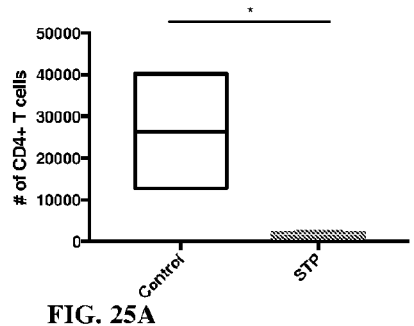
FIGS. 25A-25F are graphs showing counts of inflammatory immune cells and percentages of Tregs from the CNS 28 days post disease induction. Immune cells from brain and spinal cord were isolated from each mice, and were analyzed by FACS.
Figure 25B:
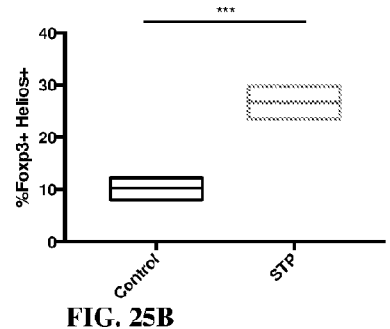
Figure 25C:
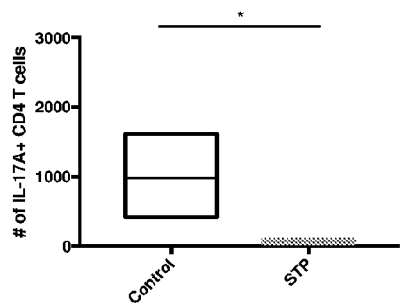
Figure 25D:
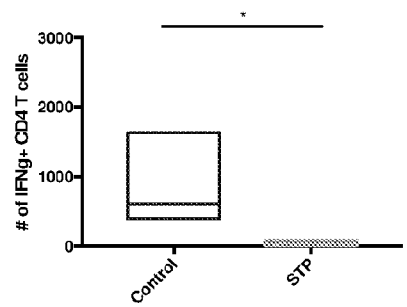
Figure 25E:
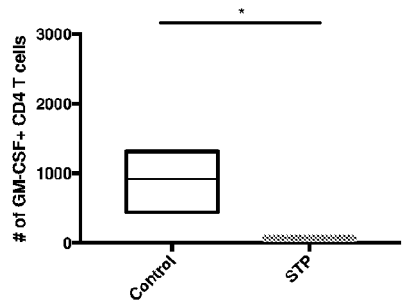
Figure 25F:
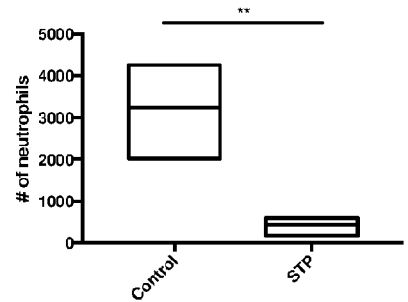

Increase in the Treg population can be attributed to two possibilities: de novo recruitment of Tregs from peripheral tissues or expansion of pre-existing Tregs. Observation of increase in both nTregs and iTregs in mLN, but not spleen, showed the expansion of pre-existing Tregs was the cause of Treg increase. As the gut microbiome is widely known to foster high proportions of varying types of Tregs, the lamina propia of large intestine in mice treated with STP was studied. Surprisingly, no differences in the gut were detected (FIG. 21), showing that there was no noticeable recruitment of Tregs from the large intestine. The expansion of Tregs in vivo through tamoxifen-induced YFP labeling of Foxp3$^+$ cells was tracked as previously described (Rubtsov et al., Science, 329:1667-1671 (2010)). In STP-treated mice, the increase of GFP expression was attributed by increase in YFP expression, showing that the increase of Tregs by STP was due to pre-existing Tregs (YFP$^+$GFP$^+$ CD4$^+$ T cells). Altogether, the results showed that STP preferentially expanded pre-existing Tregs to the greatest extent in vivo, accentuating the importance of sequential and spatial delivery of RAPA and OVA.

Example 8. Prophylactic Treatment of EAE Disease Model with STP

In summary, the earlier delivery of RAPA relative to OVA results in DC and antigen-specific T cell tolerance (FIGS. 6A-6C). Longer exposure to free RAPA decreases DC surface markers, such as CD80, CD86, PD-L1, and MHC II, while free OVA did not. However, when DCs were treated with both free RAPA and free OVA, DCs treated with free RAPA prior to free OVA (free RAPA$_E$/OVA$_L$) resulted in significantly decreased expression of DC surface markers overall. DCs treated with free RAPA and free OVA for 72 hours manifested a similar phenotype to DCs treated with free RAPA and free OVA for 24 hours, emphasizing that the sequence of RAPA and OVA delivery was the main cause of the decreased surface marker expression, not the exposure duration of free RAPA. More pronounced effect of sequential delivery was observed when RAPA and OVA were encapsulated in PLGA nanoparticles, increasing the population of PD-L1$^{hi}$ tolerogenic DCs. Nanoparticle RAPA$_E$/OVA$_L$ DCs were also able to increase the induction of Tregs in vitro and ex vivo. Tregs induced by RAPA and OVA nanoparticles were highly suppressive in an antigen-specific manner.

An advantage of nanoparticle delivery of RAPA and OVA, was particularly attributed to the increase of PD-L1 expression when DCs were treated with RAPA nanoparticles. Therefore, fine tuning of RAPA and OVA kinetics by nanoparticles has a high potential for modulation of the immune system and can be further adjusted for any desired immunotherapy.

Figure 15A:
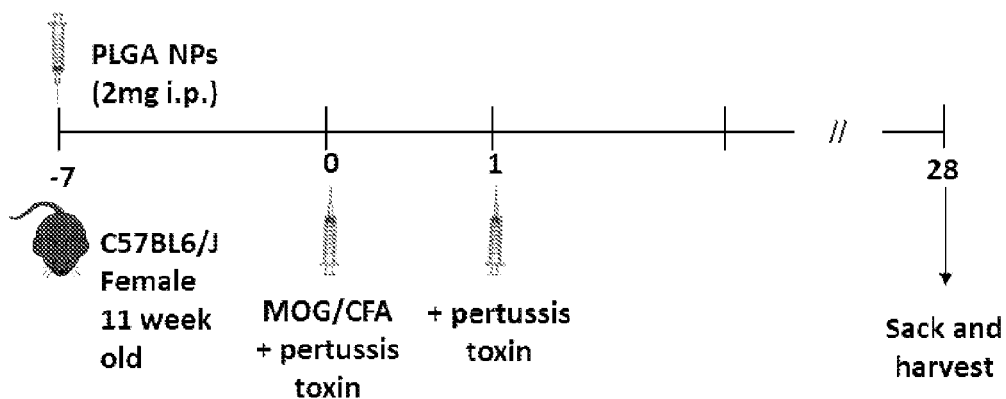
FIG. 15A is a diagram showing the experimental setup used to obtain the data in FIGS. 15B and 15C.

As the temporal effect of RAPA and OVA nanoparticles are apparent both in vitro and in vivo in induction of Tregs, exploiting the timing of RAPA and OVA delivery can be used to develop Tregs for treatment of autoimmune diseases in subjects, as demonstrated below Materials and Methods FIG. 15A is a diagram showing the experimental setup used to obtain the data in FIGS. 15B and 15C. The animal models for prophylactic EAE disease studies were established as described in "EAE induction by Active Immunization in C57BL6 Mice" manual, version 2017-01 (EK-2110, Hooke Laboratories, Inc.). A day −7, C57BL6 female mice of 11 weeks old received by i.p. injection: Mock injection (line 1), PLGA NPs containing RAPA (line 2), MOG$_{35-55}$ (MOG, line 3), MOG$_{35-55}$ and RAPA (MOG/RAPA, line 4), or STP (containing MOG$_{35-55}$ in the core particle and RAPA in the tethered particle, STP, line 5) at 2 mg. On day 0, the mice received MOG$_{35-55}$, complete Freund's adjuvant (CFA), and pertussis toxin. On day 1, the mice received pertussis toxin. On day 28, the mice were weighed, EAE disease score determined, and the mice sacrificed with brain and spinal cord (collectively, the CNS) taken for further analyses. The CNS tissue was analyzed for the total lymphocyte population and for detecting T cell subsets.

Results

Figure 15B:
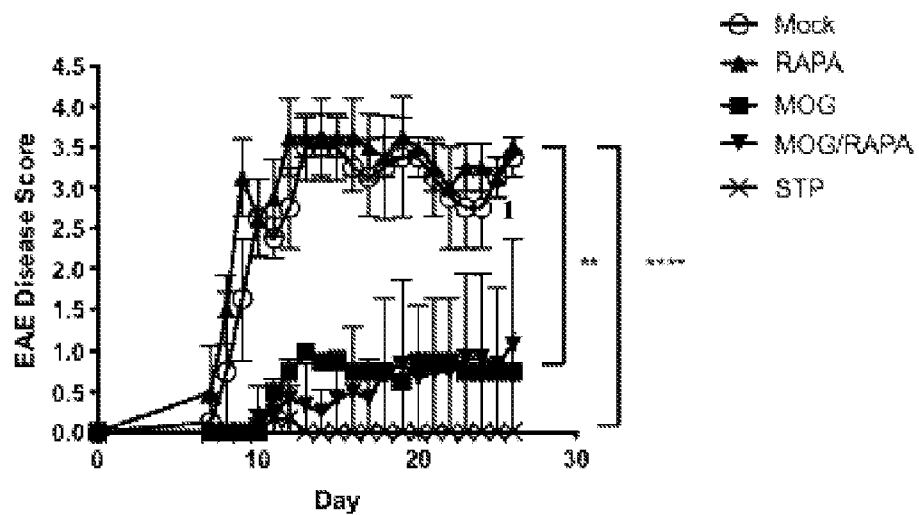
FIG. 15B is a graph showing the change in EAE Disease Score over time (days) in mice prophylactically treated with Mock injection, PLGA NPs containing RAPA, $MOG_{35-55}$ (MOG), $MOG_{35-55}$ and RAPA (MOG/RAPA), or STP (containing $MOG_{35-55}$ in the core particle and RAPA in the tethered particle, STP), at 2 mg.

FIG. 15B is a graph showing the change in EAE Disease Score over time (days) in mice that prophylactically received Mock injection (line 1), PLGA NPs containing RAPA (line 2), $MOG_{35-55}$ (MOG, line 3), $MOG_{35-55}$ and RAPA (MOG/RAPA, line 4), or STP (containing $MOG_{35-55}$ in the core particle and RAPA in the tethered particle, STP, line 5), at 2 mg. FIG. 15C is a graph showing the change in mass (g) over time (days) for mice that prophylactically received Mock injection (line 1), PLGA NPs containing RAPA (line 2), $MOG_{35-55}$ (MOG, line 3), $MOG_{35-55}$ and RAPA (MOG/RAPA, line 4), or STP (containing $MOG_{35-55}$ in the core particle and RAPA in the tethered particle, STP, line 5), at 2 mg. The results show that the combined treatment, with immunomodulator first then antigen, is highly effective in inducing tolerance.

Example 9. Therapeutic Treatment of EAE Disease Model with STP

Materials and Methods

Figure 16A:
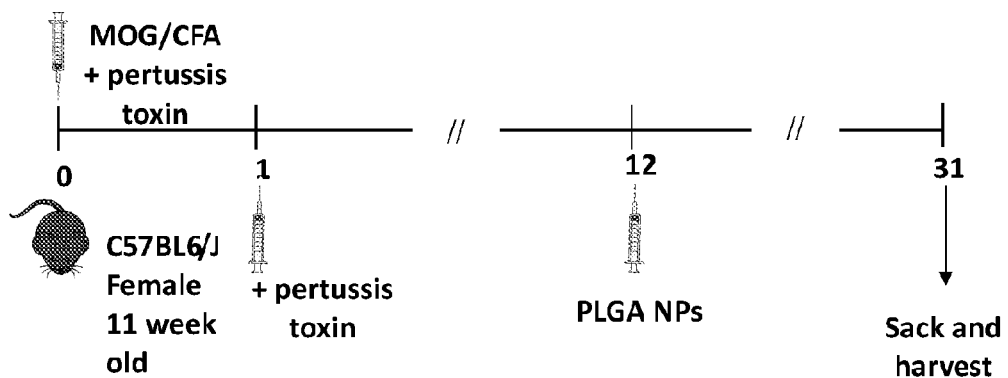
FIG. 16A is a diagram showing the experimental setup used to obtain the data in FIGS. 16B and 16C.
Figure 16B:
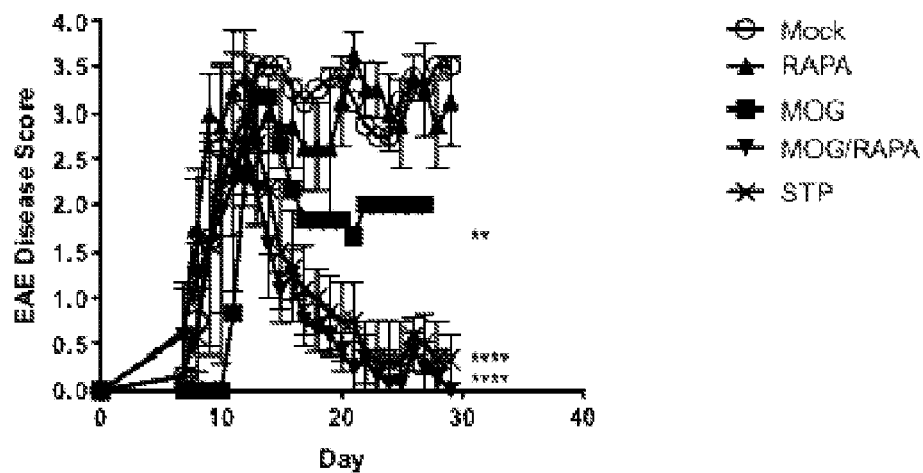
FIG. 16B is a graph showing the change in EAE Disease Score over time (days) in mice therapeutically treated with Mock injection, PLGA NPs containing RAPA, $MOG_{35-55}$ (MOG), $MOG_{35-55}$ and RAPA (MOG/RAPA), or STP (containing $MOG_{35-55}$ in the core particle and RAPA in the tethered particle, STP), at 2 mg. EAE disease score of mice treated with higher dose of particles (2 mg) at the peak of disease (day 13). Statistical significance is determined by comparison of each group's corresponding day to Mock by student t-test. (N=5).
Figure 16C:
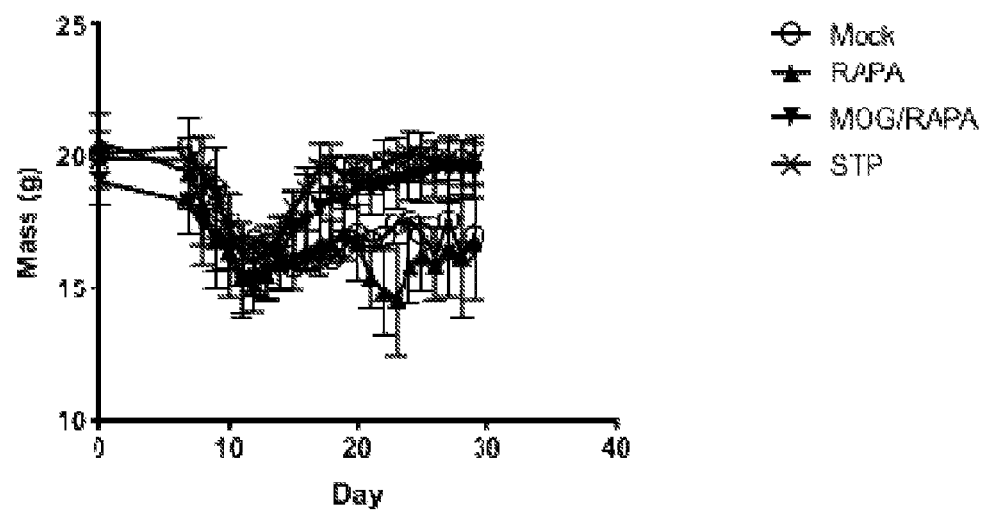
FIG. 16C is a graph showing the change in mass (g) over time (days) for mice that therapeutically received Mock injection, PLGA NPs containing RAPA, $MOG_{35-55}$ and RAPA (MOG/RAPA, or STP (containing $MOG_{35-55}$ in the core particle and RAPA in the tethered particle, STP), at 2 mg.
Figure 17A:
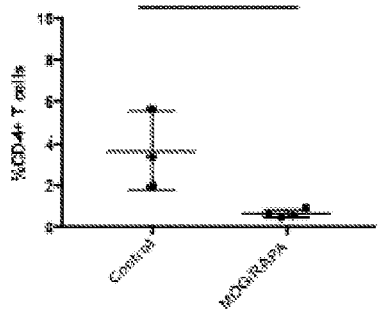
FIGS. 17A-17F are graphs showing the change in CD4+ T cell populations (FIGS. 17A-17C), pathogenic cytokine producing CD4+ T cells (FIGS. 17D and 17E), and neutrophil cell populations (FIG. 17F) in the CNS of mice prophylactically treated with i.p. injected $MOG_{35-55}$/RAPA NP when compared to those in the CNS of control mice treated with mock i.p. injection. The data show that $MOG_{35-55}$/RAPA NP expand Tregs (FIGS. 17B and 17C), while the overall CD4+ T cell population in the CNS is reduced (FIG. 17A), suppress pathogenic cytokine producing cells (FIGS. 17D and 17E), and neutrophil trafficking (FIG. 17F) when compared to those in the CNS of control mice.
Figure 17D:
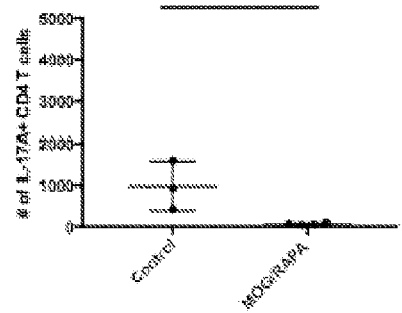
Figure 17B:
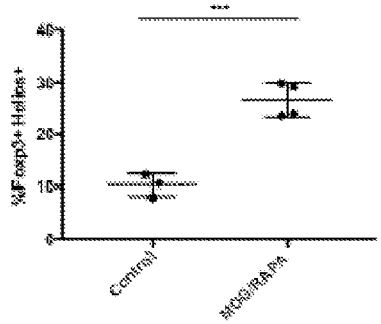
Figure 17E:
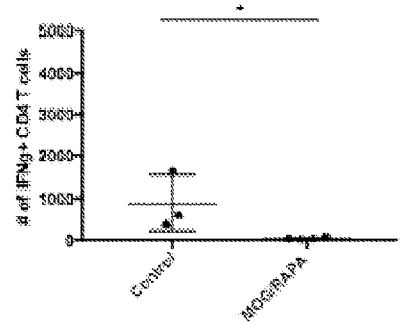
Figure 17C:
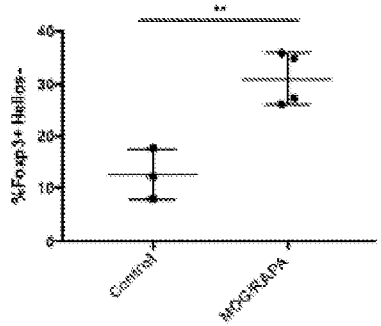
Figure 17F:
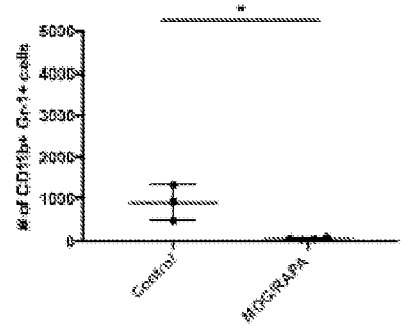

FIG. 16A is a diagram showing the experimental setup used to obtain the data in FIGS. 16B and 16C. The animal models for therapeutic EAE disease studies were established as described in "EAE Induction by Active Immunization in C57BL6 Mice" manual, version 2017-01 (EK-2110, Hooke Laboratories, Inc.). A day 0, C57BL6 female mice of 11 weeks old received by i.p. injection $MOG_{35-55}$, complete Freund's adjuvant (CFA), and pertussis toxin. On day 1, the mice received pertussis toxin. On day 12, the mice received by i.p. injection: Mock injection (line 1), PLGA NPs containing RAPA (line 2), $MOG_{35-55}$ (MOG, line 3), $MOG_{35-55}$ and RAPA (MOG/RAPA, line 4), or STP (containing $MOG_{35-55}$ in the core particle and RAPA in the tethered particle, STP, line 5) at 2 mg. On day 31, the mice were weighed, EAE disease score determined, and the mice sacrificed with brain and spinal cord (collectively, the CNS) taken for further analyses. The CNS tissue was analyzed for the total lymphocyte population and for detecting T cell subsets.

Results

FIG. 16B is a graph showing the change in EAE Disease Score over time (days) in mice that therapeutically received Mock injection (line 1), PLGA NPs containing RAPA (line 2), $MOG_{35-55}$ (MOG, line 3), $MOG_{35-55}$ and RAPA (MOG/RAPA, line 4), or STP (containing $MOG_{35-55}$ in the core particle and RAPA in the tethered particle, STP, line 5), at 2 mg. FIG. 16C is a graph showing the change in mass (g) over time (days) for mice that therapeutically received Mock injection (line 1), PLGA NPs containing RAPA (line 2), $MOG_{35-55}$ and RAPA (MOG/RAPA, line 4), or STP (containing $MOG_{35-55}$ in the core particle and RAPA in the tethered particle, STP, line 5), at 2 mg.

FIGS. 17A-17F are graphs showing the change in CD4+ T cell populations (FIGS. 17A-17C), pathogenic cytokine producing CD4+ T cells (FIGS. 17D and 17E), and neutrophil cell populations (FIG. 17F) in the CNS of mice prophylactically treated with i.p. injected $MOG_{35-55}$/RAPA NP over those in the CNS of control mice treated with mock i.p. injection. The data show that $MOG_{35-55}$/RAPA NP expand Tregs (FIGS. 17B and 17C), while the overall CD4+ T cell population in the CNS is reduced (FIG. 17A), suppresses pathogenic cytokine producing cells (FIGS. 17D and 17E), and neutrophil trafficking (FIG. 17F) over those in the CNS of control mice.

Experimental autoimmune encephalomyelitis (EAE) is an autoimmune disease characterized by inflammatory demyelination of the CNS. It has been well-established that pathogenicity of Th17 cells is the primary cause of the autoimmunity in EAE and that restoration of Th17/Treg axis is imperative for the reversal of the disease. As antigen-specific Tregs are crucial for restoration from EAE, the effect of STP in prevention and treatment of EAE was investigated. It is demonstrated that STP platform was applicable to different antigens, including myelin oligodendrocyte glycoprotein residues 35-55 ($MOG_{35-55}$), in 2D2 transgenic mice, which have transgenic T cells specific for $MOG_{35-55}$ (FIGS. 22A-22D). As expected with OVA STP, an increase in Foxp3+ population and activated CD44+ T cells was detected, while showing no changes in NK cells and RORgt+CD4 T cells (FIGS. 22A-22D). Induction of tolerance with a different antigen in 2D2 mice strongly emphasized the potential of STP for prevention and treatment of EAE, as $MOG_{35-55}$ is the primary antigen for pathogenesis of EAE.

Figure 15C:
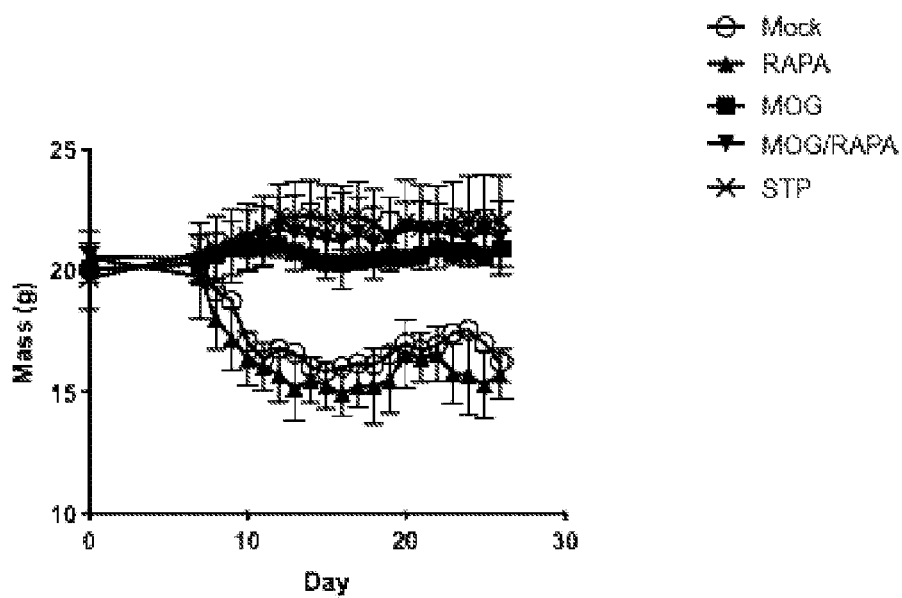
FIG. 15C is a graph showing the change in mass (g) over time (days) for mice that prophylactically received Mock injection, PLGA NPs containing RAPA, $MOG_{35-55}$ (MOG), $MOG_{35-55}$ and RAPA (MOG/RAPA), or STP (containing $MOG_{35-55}$ in the core particle and RAPA in the tethered particle, STP), at 2 mg. Error bars represent standard deviation between each group (N>5) (statistical significance determined by student t-test). Particles were injected one week before induction of disease. Mice were monitored and scored daily until 28 days post disease induction. (N>8; p-values were determined by student t-test on day 28).

Administration of MOG, MOG/RAPA, and STP, but not RAPA nanoparticles, prevented the onset of EAE and disease mediated weight loss (FIGS. 15B, 15C, and 16B). More strikingly, STP showed superiority to MOG/RAPA and MOG nanoparticles, completely preventing EAE even after day 10 (FIG. 15B). Compared to the untreated group, mice treated with STP showed significantly less infiltration of immune cells and the degree of demyelination in the spinal cord sections. In the CNS, fewer counts of overall CD4 T cells, inflammatory cytokine producing CD4 T cells (IL-17A$^+$, IFNg$^+$, and GM-CSF$^+$), and neutrophils were detected, showing that systemic STP administration was able to block lymphocyte trafficking to the CNS in both acute (14 days post disease induction) and chronic (28 days post disease induction) stages of EAE (FIGS. 24A-24F and 25A-25F). However, similar proportions of Tregs in day 14 and increased proportion of Tregs in day 28 (FIGS. 24A-24F and 25A-25F) was detected, showing that the decrease in T cells is biased towards inflammatory CD4 T cells and neutrophils. Interestingly, there was an overall increase of CD4 T cells in the draining lymph node (dLN) (FIGS. 23A-23F), showing that the mechanism of EAE prevention could be through blockade of infiltration of immune cells to the CNS.

Figure 26:
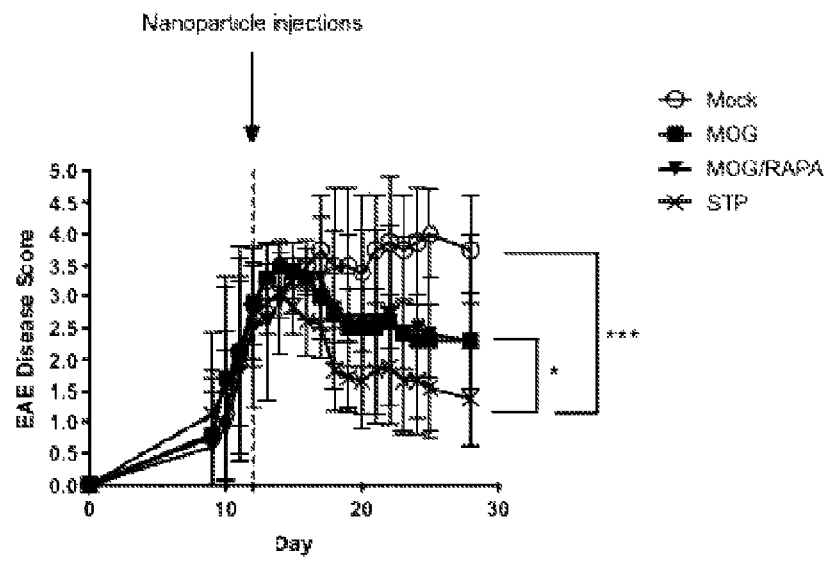
FIG. 26 is a graph showing EAE disease score of mice with therapeutic treatment of nanoparticles (200 μg of particles per mouse). Treatments were: Mock, NPs with MOG, NPs with MOG and RAPA (MOG/RAPA), and STP. Particles were injected at the peak of disease (day 12) and scores were monitored until day 30. (N>8; p-values were determined by student t-test on day 28).

In addition to prevention of EAE incidence, STP also greatly reduced the severity of the disease when it was administered at the peak of disease (FIGS. 16B and 26). While MOG/RAPA and MOG nanoparticles had some effect in ameliorating the disease, STP outperformed both groups at low concentrations of particles (FIG. 26). Consistent with prophylactic data, RAPA nanoparticles had no effect in treatment of EAE (FIG. 16B).

Example 10. Single-Cell RNAseq Reveals Immediate Development of Alternatively Activated Macrophages (M2) and Upregulation of Antigen Presentation Genes by STP Materials and Methods Sample preparation for single-cell RNAseq. Isolated splenocytes were sorted into three distinct populations: macrophages (BCR220−, TCRβ−, MHCII+, F4/80+), DCs (BCR220−, TCRO−, MHCII+, CD11c+), and T cells (BCR220−, F4/80−, CD11c−, TCRs+). Within each group, the total of 3,000 cells (1:1:1 ratio of macrophages, DCs, and T cells) were sent to Yale Center for Genome Analysis for 10× chromium single-cell RNA sequencing.

Construction of 10× Genomic Single Cell 3' RNA-Seq libraries and sequencing. Prepared single cell suspensions were mixed in RT Master Mix, loaded on the Single Cell a Chip and partitioned with a pool of about 750,000 barcoded gel beads to form nanoliter-scale Gel Beads-In-Emulsions (GEMs). Upon dissolution of the Gel Beads in a GEM, the primers with the unique cell barcodes are released and mixed with cell lysate and Master Mix. Incubation of the GEMs then produces barcoded, full-length cDNA from poly-adenylated mRNA. Silane magnetic beads are used to remove leftover biochemical reagents and primers from the post GEM reaction mixture. Full-length, barcoded cDNA is then amplified by PCR to generate sufficient mass for library construction. Enzymatic Fragmentation and Size Selection are then used to optimize the cDNA amplicon size prior to library construction, which includes end Repair, A-tailing, adaptor Ligation, and sample indexing PCR to produce Illumina-ready sequencing libraries. The final libraries contain the P5 and P7 primers used in Illumina bridge amplification. A 16 bp 10× Barcode and 10 bp UMI are encoded in Read 1, while Read 2 is used to sequence the cDNA fragment. In addition to performing standard analysis steps such as demultiplexing, alignment, and gene counting, the Cell Ranger™ analysis pipelines perform secondary analysis and visualization to generate expression data with single-cell resolution.

scRNAseq data analysis. For all scRNAseq data analysis, the standardized protocol provided by Satija Lab (New York Genome Center™), Seurat R package v3.0, was followed (https://satijalab.org/seurat). More specifically, processed raw data obtained by YCGA were inputted to Seurat v3.0 and quality control test was performed. Cells with outlier number of read counts were excluded. Next, the data was log transformed and normalized by the total expression. Principal component analysis (PCA) was performed for linear dimensionality reduction and significant PCs were determined based on the jackstraw analysis from Seurat. Statistically significant PCs were selected as input for t-distributed Stochastic Neighbor Embedding (tSNE) in order to visualize clustering of samples. Canonical markers that were used to identify each cluster were obtained through comparison of cells in a given cluster to the cells in all other clusters using likelihood ratio test, and markers with lowest corrected p-value were ranked by significance. Detection of statistically significant differentially expressed genes in each cluster was completed through comparison of gene expression between samples in a pairwise manner.

Pathway analysis. Significantly differentially expressed genes in cluster 5 and cluster 6 were used as input for Ingenuity Pathway Analysis (IPA, April 2018, Qiagen) or g:Profiler (https://biit.cs.ut.ee/gprofiler/index.cgi) testing for canonical KEGG pathway enrichment. A one-tailed Fisher's exact test was performed to test the probability of the overlap between our input gene set and a given reference gene set by chance events. The Benjamini-Hochberg (B-H) method was applied to correct for multiple comparisons.

Results

The mechanism of STP-mediated tolerance in vivo was investigated. As nanoparticles and STP are preferentially uptaken through endocytosis due to their particle-like design, systemic, cellular distribution of STP in vivo would be heavily localized in antigen presenting cells. Macrophages and dendritic cells exhibited highest uptake of nanoparticles, while T and B lymphocytes did not (FIG. 10A). In the spleen, several class subsets of DCs exist, such as $CD8a^+$ (lymphoid) DCs and $CD11b^+$ (myeloid) DCs. No significant differences between subsets of DCs and macrophages for nanoparticle uptake were detected (FIG. 10A). As such, the immediate cellular effect of particles would be best found in antigen presenting cells.

Figure 27:
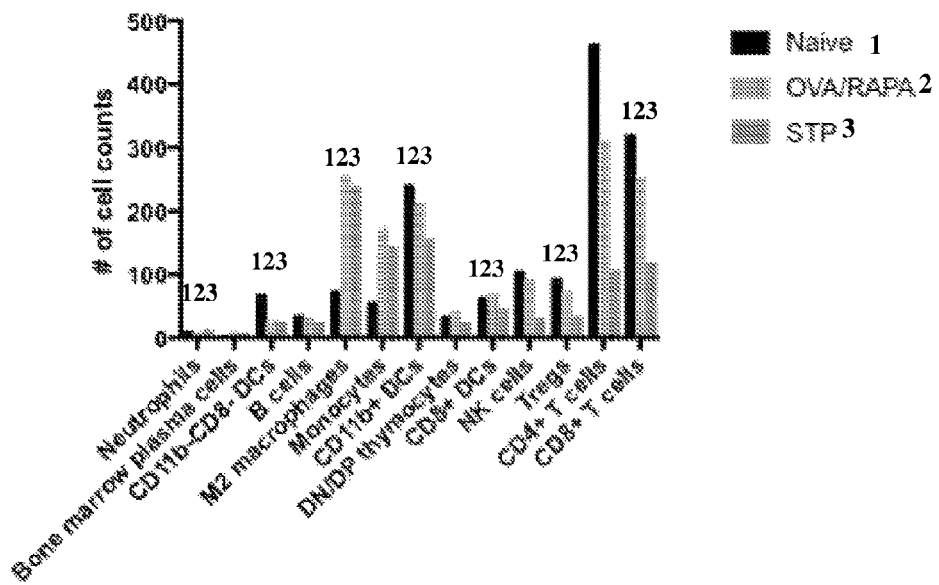
FIG. 27 is a bar graph representing number of cells found in each sample for three groups: Naive (1), OVA/RAPA (2), and STP (3) from the single-cell RNAseq analysis. Labels 123 are shown for every other cell type, but the order of groups 123 applies to all the cell types shown.

In order to further elucidate changes in cellular and genetic level, single-cell RNA sequencing on mice that have been treated with OVA/RAPA nanoparticles and STP was performed. Splenocytes were harvested a day after the final STP injection. The noise of the samples and analysis was minimal, as they exhibited the expected number of genes, barcodes, and mitochondrial genes (data not shown). Principal component analysis revealed that the cellular population could be divided into thirteen distinct clusters, which were each assigned as cell types based on its transcriptome (Table 5). Overlay of samples reveal a striking difference in spatial distribution in control group vs. STP, especially in M2 macrophages and monocytes (cluster 5 and 6) (data not shown). The number of cells found in M2 macrophages and monocyte cluster was significantly higher in STP compared to the control (FIG. 27).

TABLE 5

Thirteen distinct clusters assigned as cell types based on its transcriptome.

| Cluster # | Cell Type |
|---|---|
| 1 | Neutrophils |
| 2 | Bone marrow plasma cells |
| 3 | CD11b-CD8- DCs |
| 4 | B cells |
| 5 | M2 macrophages |
| 6 | Monocytes |
| 7 | CD11b+ DCs |
| 8 | DN/DP thymocytes |
| 9 | CD8+ DCs |
| 10 | NK cells |
| 11 | Tregs |
| 12 | CD4+ T cells |
| 13 | CD8+ T cells |

Differentially expressed genes of M2 macrophages and monocyte clusters between samples was investigated. Expectedly, a huge upregulation of genes involved in antigen presentation and proteasome (Table 6, showing differences in spatial distribution per samples in clusters 5 and 6) was detected. The results show that STP injected particles lead to enhancement of M2 macrophages and transcriptional changes in antigen presentation immediately after STP injection, showing again that expansion of M2 macrophages could be a bridge to STP-induced tolerance in vivo.

TABLE 6

Top-ranked pathways of cluster 5 and 6 for Control vs.
STP based on KEGG pathway analysis via g:profiler
(https://biit.cs.ut.ee/gprofiler/index.cgi) or IPA.

| Cluster 5 | | Cluster 6 | |
| --- | --- | --- | --- |
| Biological pathways (KEGG) | Corrected p-value | Biological pathways (KEGG) | Corrected p-value |
| Antigen processing and presentation | 2.44e−10 | Antigen processing and presentation | 3.83e−26 |
| Proteasome | 9.18e−08 | Allograft rejection | 5.31e−13 |
| Intestinal immune network for IgA production | 1.03e−04 | Graft vs. Host Disease Signaling | 6.42e−13 |
| Graft vs. Host Disease Signaling | 4.67e−04 | Autoimmune Thyroid Disease Signaling | 7.48e−13 |
| Helper T cell differentiation | 3.61e−03 | OX40 Signaling Pathway | 8.46e−13 |

At least 30 upregulated genes in STP compared to Ctrl were selected and analyzed for biological pathways.

Example 11. Importance of M2 Macrophage in Treg Expansion and Tolerance by STP Materials and Methods Depletion of Macrophage and PD-L1. Clodronate liposomes (ClodronateLiposomes, Liposoma B.V.) were injected (i.p.) (200 µL per mice) for depletion of macrophages. PD-L1 neutralizing antibody (InVivoMab; 10F.9G2, Bio X Cell, West Lebanon, N.H., USA) was injected (i.p.) 200 µg per mouse triweekly for PD-L1 depletion.

Results

Given that the number of M2 macrophages had greatly increased in early stage of STP-treated mice, the importance of M2 macrophages in induction of tolerance at a later timepoint was investigated where the expansion of Tregs was detected. F4/80+ macrophages were robustly depleted through administration of clodronate liposomes. Representative FACS plots were generated demonstrating percentage of cells that expressed F4/80 after clodronate injections (gated on Lin:−). OT-II mice were injected with clodronate (200 µL) once at day 0. Splenocytes were harvested at each timepoint and cells were analyzed by FACS. FACS plots not shown. The percentage of cells expressing F4/80 reduced from 6.87% in control sample, to 0.42% for clodrosome Day 2 sample, to 0.84% for clodrosome Day 4 sample, to 0.74% for clodrosome Day 7 sample.

Figure 28A:
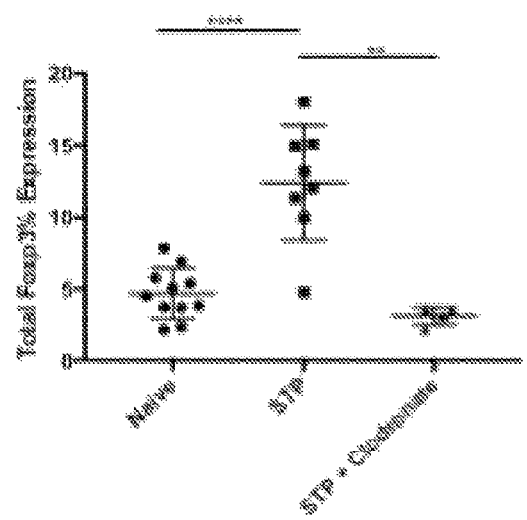
FIG. 28A is a graph showing percentage of Foxp3 expressing cells (gated on CD4 T cells). OT-II mice, with or without depletion of macrophages by clodronate liposomes, were injected with STP, and splenocytes were harvested and analyzed by FACS (N>4, p-values were determined by student t-test).
Figure 28B:
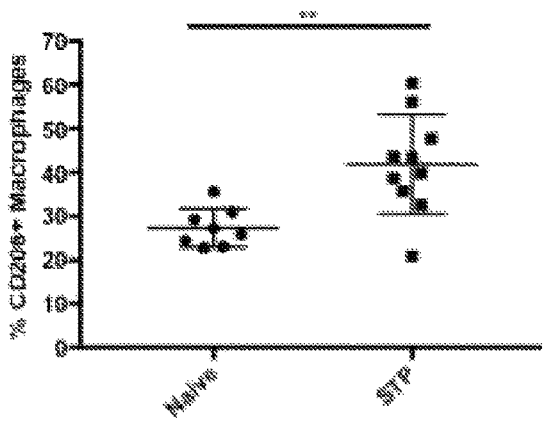
FIG. 28B is a graph showing percentage of CD206 expressing cells (gated on Lin:−, CD11c−, CD11b+, F4/80+ cells). Nanoparticles were injected into OT-II mice as described in FIG. 13A, and the percentage of M2 macrophages (CD206+ macrophages) analyzed (N>8, p-values were determined by student t-test).

Depletion of macrophages inhibited STP's ability to expand Tregs (FIG. 28A), showing that macrophages were essential in STP uptake and inducing tolerance. M2 macrophage increase in STP-treated mice was also confirmed by flow cytometry (FIG. 28B), showing that there was a selective increase of M2 in the M1/M2 axis. As such, complementary to results from single-cell RNA sequencing, the results emphasized the importance of tolerogenic M2 by STP as a mechanism of expansion of Tregs and tolerance.

CD8a+ DCs are well-known for immunogenicity and cross presentation. Several studies have shown that CD8a+ DCs are responsible for establishment of cross-tolerance, particularly to tissue-associated antigens. To investigate if CD8a+ DCs had also increased in STP-treated mice, the ratio of CD11b+ DCs to CD8a+ DCs in the spleen was compared. The ratio of 33D1+ DCs (CD11b+ DCs) to XCR1+ DCs (CD8a+ DCs) had significantly decreased in STP-treated mice (FIG. 29), showing that cross-tolerance associated CD8a+ DCs were also recruited to the spleen, consistent to increase in M2 macrophage.

Figure 29:
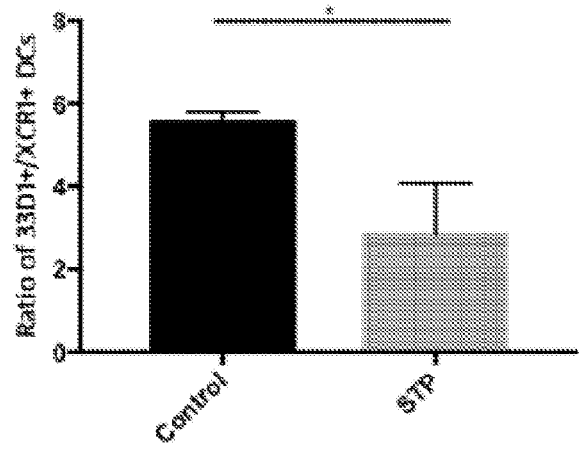
FIG. 29 is a bar graph showing the ratio of 33D1+ DCs to XCR1+ DCs (N=3; p-value was determined by student t-test) from representative FACS plot showing XCR1 expressing DCs (CD8a+ DCs) and 33D1 expressing DCs (CD11b+ DCs) (gated on Lin:−, CD11c+ MHCII+ cells). Splenocytes from mice that have been injected with STP (as described in FIG. 13A) were harvested and analyzed by FACS.

Specifically, STPs increased the ratio of CD8a+ DCs to CD11b+ DCs in the spleen. Representative FACS plot showed XCR1 expressing DCs (CD8a+ DCs) and 33D1 expressing DCs (CD11b+ DCs) (gated on Lin:−, CD11c+ MHCII+ cells) were 6.25%: 35.8%, respectively, in controls and 11.6%: 24.0% with STP treatment. Splenocytes from mice that have been injected with STP (as described in FIGS. 13B-13G) were harvested and analyzed by FACS. FIG. 29 shows the ratio of 33D1+ DCs to XCR1+ DCs (N=3; p-value was determined by student t-test).

Example 12. STP Induces Tolerance Through Upregulation of PD-L1

Materials and Methods

Using FACS analysis, the cells were analyzed by detecting Foxp3 expressing cells (gated on CD4 T cells). OT-II mice with or without depletion of macrophages by clodronate liposomes were injected with STP, and splenocytes were harvested and analyzed by FACS (N>4). CD206 expressing cells were also analyzed (gated on Lin:−, CD11c−, CD11b+, F4/80+ cells). Nanoparticles were injected in OT-II mice as described for FIGS. 13B-13G, and the percentage of M2 macrophages (CD206+ macrophages) was analyzed (N>8). PD-L1 expressing M2 cells from mice were analyzed as described for 206 expressing cells (N>8). Cells from spleen or mLN of OT-II mice with or without depletion of PD-L1 were analyzed. Splenocytes or cells from mesenteric lymph node were harvested after treatment of STP with or without PD-L1 neutralizing antibody (N>4). p-values were determined by student t-test.

Results

Figure 28C:
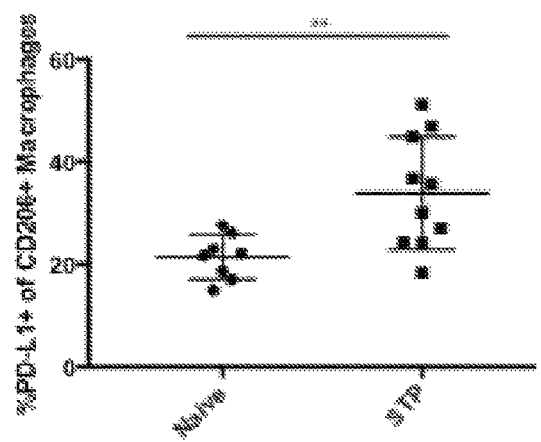
FIG. 28C is a graph showing the percentage of PD-L1 expressing M2 cells from mice as described in FIG. 28B (N>8, p-values were determined by student t-test).
Figure 28D:
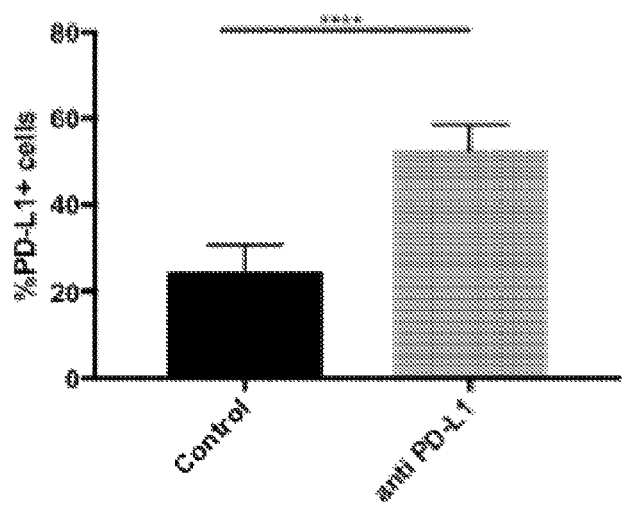
FIG. 28D is a bar graph showing PD-L1 expression of mice injected with control or PD-L1 neutralizing antibody. Harvested splenocytes from mice treated with control or PD-L1 antibody and PD-L1 expression was analyzed by FACS. (N=5; p-value was determined by student t-test).
Figures 28E, 28F:
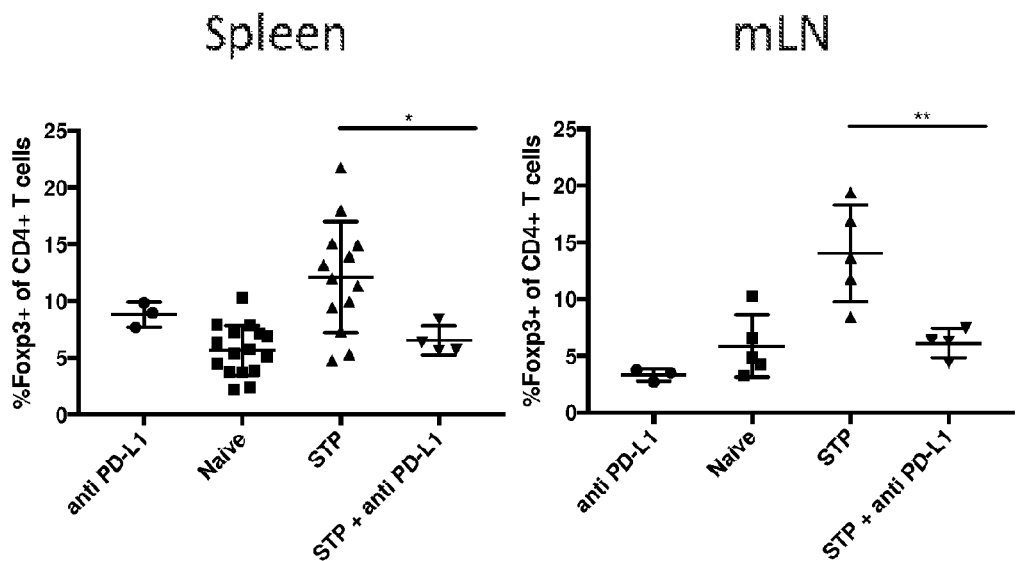
FIGS. 28E and 28F are graphs showing analysis of representative FACS plots of OT-II mice with or without depletion of PD-L1. Splenocytes or cells from mesenteric lymph node were harvested after treatment of STP with or without PD-L1 neutralizing antibody (N>4, p-values were determined by student t-test).

The molecular mechanism of STP-induced tolerance in vivo was investigated. Amongst several tolerogenic markers on APCs, PD-L1 is a well-known co-inhibitory surface and its role in development of Tregs and immune suppression has been well-established. As PD-L1 is also known to be upregulated on tolerance-associated M2 macrophages, the role of PD-L1 as a molecular mechanism of action of STP was explored. STP significantly increased the level of PD-L1 on M2 (FIG. 28C), suggesting that PD-L1 upregulation on M2 is a mechanism of tolerance by STP. To confirm the dependence of PD-L1 of STP, broadly neutralizing antibody (anti PD-L1) was used to decrease the level of PD-L1 expression in vivo, as shown in FIG. 28D. In both spleen and mLN, anti PD-L1 treated mice failed to expand Tregs even with STP administration (FIGS. 28E and 28F). Altogether, PD-L1 expression on M2 macrophages by STP was essential for expansion of Tregs and immune tolerance in vivo.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A composition comprising a population of multi-agent particles for
    spatial and/or temporal antigen-specific immunomodulation in a subject, the multi-agent particles comprising
    (a) core particles comprising polyhydroxy acid polymers and antigen,
    (b) biotin-PEG-β-cyclodextrin complexes tethered to the core particles, and
    (c) tethered particles comprising the immunomodulatory agent rapamycin.

2. The composition of claim 1, wherein the multi-agent particles are targeted by size, composition, or a targeting moiety to specific cells.

3. The composition of claim 1, wherein the tethered particles comprise a PAMAM dendrimer.

4. The composition of claim 1, wherein the tethered particles are formed of rapamycin.

5. The composition of claim 2, wherein the multi-agent particles comprise a targeting moiety attached to the core particle.

6. The composition of claim 1, wherein the multi-agent particles have an average particle size between 10 nm and 1000 nm.

7. The composition of claim 1, wherein the tethered particles have an average particle size between 0.1 nm and 200 nm.

8. The composition of claim 1, wherein the antigen is selected from the group consisting of a degenerative disease antigen, an atopic disease antigen, an autoimmune disease or self antigen, an alloantigen, a xenoantigen, an allergen, an addictive substance, a metabolic disease enzyme or an enzymatic product, a drug, an anti-drug antibody, and a vector antigen.

9. The composition of claim 1, wherein the antigen is encapsulated in, conjugated to, or covalently or non-covalently attached to the core particle.

10. The composition of claim 5, comprising a targeting moiety to an antigen presenting cell.

11. The composition of claim 10, wherein the antigen presenting cell-targeting moiety is selected from the group consisting of a monocyte targeting moiety, macrophage targeting moiety, dendritic cell targeting moiety, B-cell targeting moiety, Langerhans cell targeting moiety, and microglia targeting moiety.

12. The composition of claim 1, comprising a pharmaceutically acceptable excipient.

13. The composition of claim 1, wherein the particles release the antigen and the rapamycin in an amount and timing of release effective to induce immune tolerance to the antigen in the subject.

14. A method of treating a subject comprising administering to a subject in need thereof
    a composition comprising a population of multi-agent particles for spatial and/or temporal antigen-specific immunomodulation in a subject, the multi-agent particles comprising
    (a) core particles comprising polyhydroxy acid polymers and antigen,
    (b) biotin-PEG-β-cyclodextrin complex tethered to the core particle, and
    (c) tethered particles comprising the immunomodulatory agent rapamycin.

15. The method of claim 14, wherein the antigen is derived from an infectious disease, proliferative disease, degenerative disease, or neurodegenerative disease.

16. The method of claim 14, wherein the subject has an autoimmune disease, allergy, graft-versus-host disease, or drug reaction.

17. A method of enhancing immunomodulation comprising
    administering a composition comprising a population of multi-agent particles for spatial and/or temporal antigen-specific immunomodulation in a subject, the multi-agent particles comprising
    (a) core particles comprising polyhydroxy acid polymers and antigen,
    (b) biotin-PEG-β-cyclodextrin complex tethered to the core particle, and
    (c) tethered particles comprising the immunomodulatory agent rapamycin,
    wherein the multi-agent particles sequentially release to the same dendritic cells one or more antigens and immunomodulatory agent,
    wherein the rapamycin is released first, then the antigen to which tolerance is to be induced.

18. The method of claim 17, wherein the antigen is a food, insect or other allergen, degenerative disease antigen, atopic disease antigen, metabolic disease enzyme, drug, or self antigen to which tolerance is to be induced.

19. The composition of claim 6, wherein the average particle size of the multi-agent particle is between 60 nm and 400 nm.

20. The composition of claim 1, wherein the average particle size of the multi-agent particles is between 200 nm and 250 nm.

* * * * *